United States Patent
Shapiro et al.

(10) Patent No.: US 11,604,236 B2
(45) Date of Patent: Mar. 14, 2023

(54) OPTIMAL METHODS TO FEEDBACK CONTROL AND ESTIMATE MAGNETIC FIELDS TO ENABLE A NEURAL DETECTION SYSTEM TO MEASURE MAGNETIC FIELDS FROM THE BRAIN

(71) Applicant: HI LLC, Los Angeles, CA (US)

(72) Inventors: Benjamin Shapiro, Culver City, CA (US); Ricardo Jimenez-Martinez, Culver City, CA (US); Julian Kates-Harbeck, Marina Del Rey, CA (US)

(73) Assignee: HI LLC, Los Angeles, CA (US)

( * ) Notice: Subject to any disclaimer, the term of this patent is extended or adjusted under 35 U.S.C. 154(b) by 302 days.

(21) Appl. No.: 17/160,195

(22) Filed: Jan. 27, 2021

(65) Prior Publication Data

US 2021/0247471 A1 Aug. 12, 2021

Related U.S. Application Data

(60) Provisional application No. 63/035,680, filed on Jun. 5, 2020, provisional application No. 62/975,727, filed on Feb. 12, 2020.

(51) Int. Cl.
*G01R 33/26* (2006.01)
*A61B 5/00* (2006.01)
*A61B 5/245* (2021.01)

(52) U.S. Cl.
CPC .............. *G01R 33/26* (2013.01); *A61B 5/245* (2021.01); *A61B 5/4064* (2013.01)

(58) Field of Classification Search
CPC .... G01R 33/26; G01R 33/02; G01R 33/0017; G01R 33/022; G01R 33/035; G01R 33/24;

(Continued)

(56) References Cited

U.S. PATENT DOCUMENTS 3,173,082 A 3/1965 Bell et al.
3,257,608 A 6/1966 Bell et al.
(Continued)

FOREIGN PATENT DOCUMENTS

EP 2738627 A3 6/2014
EP 2380029 B1 10/2015
(Continued)

OTHER PUBLICATIONS

Kiwoong Kim, Samo Begus, Hui Xia, Seung-Kyun lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014. pdf.

(Continued)

*Primary Examiner* — Carolyn A Pehlke
(74) *Attorney, Agent, or Firm* — Michael J. Bolan; Vista IP Law Group, LLP

(57) ABSTRACT

An active shield magnetometry system comprises at least one magnetic field actuator configured for generating an actuated magnetic field that at least partially cancels an outside magnetic field, thereby yielding a total residual magnetic field. The active shield magnetometry system further comprises a plurality of magnetometers respectively configured for measuring the total residual magnetic field and outputting a plurality of total residual magnetic field measurements. The active shield magnetometry system further comprises at least one feedback control loop comprising at least one optimal linear controller configured for controlling the actuated magnetic field at least partially based on at least one of the plurality of total residual magnetic field measurements respectively output by at least one of the plurality of magnetometers.

28 Claims, 10 Drawing Sheets

(58) Field of Classification Search
CPC ............ G01R 33/0035; G01R 33/0354; G01R 33/0358; G01R 33/0206; G01R 33/0094; G01R 33/0076; G01R 33/00; G01R 33/025; G01R 33/028; A61B 5/245; A61B 2562/0223; A61B 5/00; A61B 5/0042; A61B 5/242; A61B 5/4064; A61B 5/6803; A61B 5/0522; A61B 5/24; A61B 5/243; A61B 5/05

See application file for complete search history.

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keena et al. |
| 6,472,869 B1 | 10/2002 | Upschulte et al. |
| 6,665,553 B2 | 12/2003 | Kandori et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okanden et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,256 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Komack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Komack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,088,535 B1 | 10/2018 | Shah |
| 10,162,016 B2 | 12/2018 | Gabrys et al. |
| 10,371,764 B2 | 8/2019 | Morales et al. |
| 10,772,561 B2 | 9/2020 | Donaldson |
| 2004/0232912 A1 | 11/2004 | Tsukmamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2009/0318773 A1 | 12/2009 | Jung |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parasa et al. |
| 2017/0261564 A1 | 9/2017 | Gabrys et al. |
| 2017/0332933 A1 | 11/2017 | Krishnaswamy |
| 2017/0343617 A1 | 11/2017 | Manickman et al. |
| 2017/0343695 A1 | 11/2017 | Stetson et al. |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe |
| 2018/0313913 A1 | 11/2018 | DeNatale et al. |
| 2019/0391213 A1 | 12/2019 | Alford |
| 2020/0025844 A1 | 1/2020 | Alford et al. |
| 2020/0057115 A1 | 2/2020 | Jimenez-Martinez et al. |
| 2020/0057116 A1 | 2/2020 | Zorzos et al. |
| 2020/0072916 A1 | 3/2020 | Alford et al. |
| 2020/0088811 A1 | 3/2020 | Mohsen |

FOREIGN PATENT DOCUMENTS

| | | |
|---|---|---|
| EP | 3037836 B1 | 9/2017 |
| WO | 2005081794 | 9/2005 |
| WO | 2014031985 | 2/2014 |
| WO | 2017095998 | 6/2017 |

OTHER PUBLICATIONS

Sheng, Dong & R. Perry, Abigail & Krzyzewski, Sean & Geller, Shawn & Kitching, John & Knappe, Svenja. (2017). A microfabricated optically-pumped magnatic gradiometer. Applied Physics Letters. 110. 10.1063/1.4974349.

(56) References Cited

OTHER PUBLICATIONS

Sheng, Dehong & Li, S & Dural, Nezih & Romalis, Michael. (2013). Subfemtotesla Scalar Atomic Magoetometoy Using Multi-pass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J. 2012. In situ triaxial magnetic field compensation for the spin-exchange-relaxation-free atomic magnetometer. Review of Scientific Instruments, 83(10), p. 103104.

Joan Lee, Hyun & Shim, Jeong & Moon, Han Seb & Kim, Kiwoong. (2014). Flat-response spin-exchange relaxation free atomic magnetometer under negative feedback. Optics Express. 22. 10.1364/OE.22.019887.

Griffith, Clark & Jimenez-Martinez, Ricardo & Shah, Vishal & Knappe, SvenJa & Kitching, John. (2009). Miniature atomic magnetometer integrated with flux concentrators. Applied Physics Letters—Appl Phys Lett. 94. 10.105311.2885711.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.3056152.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports. 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jiménez-Martinez, Dong Sheng, John LeBlanc, Lutz Trahms, Tilmann Sander, John Kitching, and Svenja Knappe, "Magnetic field imaging with microfabricated optically-pumped magnetometers," Opt Express 25, 7849-7858 (2017).

Slocum et al., Self-Calibrating Vector Magnetometer for Space, https:l/esto.nasa.gov/conferences/estc-2002/Papers/B3P4(Slocum).pdf.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

R.E. Slocum & L.J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically pumped magnetometer. Applied Optics. 56. 5927. 10.1364/A0.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

Larry J. Ryan, Robert E. Slocum, and Robert B. Steves, Miniature Vector Laser Magnetometer Measurements of Earth's Field, May 10, 2004, 4 pgs.

Lorenz, V.O., Dai, X., Green, H., Asnicar, T.R., & Cundiff, S.T. (2008). High-density, high temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zoloterev, Max. (2016). Magnetic shielding and exoticspin-dependent interactions. Physical Review D. 94. 10.1103/PhysRevD.94.082005.

Huang, Haichao, et al. "Single-beam three axis atomic magnetometer." Applied Physics Letters 109.6 (2016): 062404. (Year:2016).

Scott Jeffrey Seltzer: "Developments in Alkali-Metal Atomic Magnetometry", Nov. 2008 (Nov. 1, 2008 ), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Okada, Y.C., Lahteenmäki, A. and Xu, C., "Experimental analysis of distortion of magnetoencephalography signals by the skull." Clinical neurophysiology 110 (2), 230-238 (1999).

Robinson, J.T., Pohlmeyer, E., Gather, M.C., Kemere, C., Kitching, J.E., Malliaras, G.G., Marblestone, A., Shepard, K.L., Stieglitz, T. and Xie, C., "Developing Next-Generation Brain Sensing Technologies—A Review." IEEE sensors journal, 19(22), 10163-10175 (2019).

Shah, V., Knappe, S., Schwindt, P.D. and Kitching, J., "Subpicotesla atomic magnetometry with a microfabricated vapour cell." Nature Photon 1, 649-652 (2007).

Kitching, J., "Chip-scale atomic devices." Applied Physics Reviews, 5(3), 031302 (2018).

Hill, R.M., Boto, E., Rea, M., Holmes, N., Leggett, J., Coles, L.A., Papastavrou, M., Everton, S.K., Hunt, B.A.E., Sims, D. and Osborne J., "Multi-channel whole-head OPM-MEG: helmet design and a comparison with a conventional system." Neuroimage 219, 116995 (2020).

Griffith, W.C., Knappe, S. and Kitching, J., "Femtotesla atomic magnetometry in a microfabricated vapor cell." Optics express 18, (26), 27167-27172 (2010).

Boto, E., Holmes, N., Leggett, J., Roberts, G., Shah, V., Meyer, S.S., Muñoz, L.D., Mullinger, K.J., Tierney, T.M., Bestmann, S. and Barnes, G.R., "Moving magnetoencephalography towards real-world applications with awearable system." Nature, 555(7698), 657-661 (2018).

Sander, T.H., Preusser, J., Mhaskar, R., Kitching, J., Trahms, L., and Knappe, S., "Magnetoencephalography with a chip-scale atomic magnetometer." Biomedical Optics Express 3, (5), 981-990 (2012).

Borna, A, Carter, T.R., Colombo, A.P., Jau, Y.Y., McKay, J., Weisend, M., Taulu, S., Stephen, J.M., and Schwindt, P.D., "Non-invasive functional-brain-imaging with an OPM-based magnetoencephalography system." Plos one 15 (1), (2020).

Kitching, J., Knappe, S., Gerginov, V., Shah, V., Schwindt, P.D., Lindseth, B., Donley E.A., "Chip-scale atomic devices: precision atomic instruments based on MEMS." In Frequency Standards And Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Dupont-Roc, J., Haroche, S. & Cohen-Tannoudji, C., "Detection of very weak magnetic fields (10-9 gauss) by Rb zero-field level crossing resonances", Phys. Lett. A 28, 638-639 (1969).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Kominis, I.K., Komack, T.W., Allred, J.C. and Romalis, M.V., "A subfemtotesla multichannel atomic magnetometer." Nature, 422(6932), 596-599 (2003).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

(56) References Cited

OTHER PUBLICATIONS

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment." NeuroImage, 199, 408-417 (2019).
Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).
De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).
Mellinger, J., Schalk, G., Braun, C., Preissl, H., Rosenstiel, W., Birbaumer, N. and Kübler, A., "An MEG-based brain—computer interface (BCI)." Neuroimage, 36(3), 581-593 (2007).
Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).
Lightfoot, G., "Summary of the N1-P2 cortical auditory evoked potential to estimate the auditory threshold in adults". Seminars in hearing, 37(1), 1 (2016).
Virtanen, J., Ahveninen, J., Ilmoniemi, R. J., Näätänen, R., & Pekkonen, E., "Replicability of MEG and EEG measures of the auditory N1/N1m-response." Electroencephalography and Clinical Neurophysiology/Evoked Potentials Section, 108(3), 291-298 (1998).
Gascoyne, L., Furlong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).
Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multichannel magnetoencephalography." NeuroImage, 199, 598-608 (2019).
Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).
Iivanainen, J., Stenroos, M. and Parkkonen, L., "Measuring MEG closer to the brain: Performance of on-scalp sensor arrays." NeuroImage 147, 542-553 (2017).
Allred, J, C., Lyman, R. N., Komack, T. W., & Romalis, M. V. (2002). High-sensitivity atomic magnetometer unaffected by spin-exchange relaxation. Physical review letters, 89(13), 130801.
Balabas et al. Polarized alkali vapor with minute-long transverse spin-relaxation time, Phys. Rev. Lett. 105, 070801—Published Aug. 12, 2010.
Barbieri, F., Trauchessec, V. Caruso, L. Trejo-Rosillo, J. Telenczuk, B. Paul E., . . . & Ouanounou, G. (2016). Local recording of biological magnetic fields using Giant Magneto Resistance-based micro-probes. Scientific reports, 6, 39330.
Dmitry Budker and Michael Romalis, "Optical Magnetometry," Nature Physics, 2008, https://arxiv.org/abs/physics/0611246v1.
Anthony P. Colombo, Tony R. Carter, Amir Barna, Yuan-Yu Jau, Cort N. Johnson, Amber L. Dagel, and Peter D. D. Schwindt, "Four-channel optically pumped atomic magnetometer for magnetoencephalography," Opt Express 24, 15403-15416(2016).
Dang, H.B. & Maloof, AC. & Romalis, Michael. (2009). Ultra-high sensitivity magnetic field and magnetization measurements with an atomic magnetometer. Applied Physics Letters. 97.10.1063/1.3491215.
Donley, E.A. & Hodby, E & Hollberg, L & Kitching, J. (2007). Demonstration of high-performance compact magnetic shields for chip-scale atomic devices. The Review of scientific instruments. 78.083102.
Hamalainen, Matti & Ritta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2.413-497.
Hunter, D. and Piccolomo, S. and Pritchard, J. D. and Brockie, N. L. and Dyer, T. E. and Riis, E. (2018) Free-induction-decay magnetometer based on a microfabricated Cs vapor cell. Physical Review Applied (1 O).ISSN 2331-7019.
Jimenez-Martinez, R., Griffth, W.C., Wang, Y.J., Knappe, S., Kitching, J., Smith, K, & Prouty, M.D. (2010). Sensitivity comparison of Mix and frequency-modulated bell-bloom Cs magnetometers in a microfabricated cell. IEEE Transactions on Instrumentation and Measurement, 59(2), 372-378.
Knappe, Svenja & Sander, Tilmann & Trahms, Lutz. (2012). Optically-Pumped Magnetometers for MEG. Magnetoencephalography: From Signals to Dynamic Cortical Networks. 993-999. 10.10071978-3-642-33045-2_ 49.
Korth, H., K. Strohbehn, F. Tejada, A.G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.
Lenz, J. and Edelstein, S., 2006. Magnetic sensors and their applications. IEEE Sensors journal, 6(3), pp. 631-649.
Li, S & Vachaspati, Pranjal & Sheng, Dehong & Dural, Nezih & Romalis, Michael. (2011 ). Optical rotation in excess of 100 rad generated by Rb vapor in a multipass cell. Phys. Rev. A. 84. 10.1103/PhysRevA.84.061403.
Maze, J. R., Stanwix, P. I., Hodges, J. S., Hong, S., Taylor, J.M., Cappellaro, P., . . . & Yacoby, A. (2008). Nanoscale magnetic sensing with an individual electronicspin in diamond. Nature, 455(7213), 644.
J. Seltzer, S & Romalis, Michael. (2010). High-temperature alkali vapor cells with antirelaxation surface coatings. Journal of Applied Physics. 106. 114905-114905. 10.1063/1.3236649.
Seltzer, s. J., and Romalis, M.V., "Unshielded three-axis vector operation of a spin-exchange-relaxation-free atomic magnetometer." Applied physics letters 85.20 (2004): 4804-4806.
Matti S. Hämäläinen, "Magnetoencephalography: A Tool For Functional Brain Imaging", Brain Topography, vol. 5. No. 2. 1992; 8 pages.
Martin W. Hess and Peter Benner, "Fast Evaluation of Time-Harmonic Maxwell's Equations Using the Reduced Basis Method", IEEE Transactions On Microwave Theory and Techniques, vol. 61, No. 6. Jun. 2013; 10 pages.
Dipankar Sarkar and N. J. Halas, "General vector basis function solution of Maxwell's equations", Physical Review E, vol. 56, No. I. Jul. 1997; 11 pages.
M. Ortner, A. Nehorai, and H. Preissl, "A spatial point process model for solving the MEG inverse problem", Washington University in St. Louis, St. Louis, Missouri, USA, University of Arkansas for Medical Sciences, Little Rock, Arkansas, USA, University of Tuebingen, Tuebingen, Germany; Elsevier; International Congress Series I300 (2007) 253-256; 4 pages.
Non-Final Office Action for U.S. Appl. No. 17/160,179 dated Dec. 5, 2022 38 pages.
Amendment and Response for U.S. Appl. No. 17/160,179, filed Jan. 3, 2023 26 pages.
Restriction Requirement for U.S. Appl. No. 17/160,152 dated Dec. 5, 2022 8 pages.
Response to Election/Restriction Requirement filed for U.S. Appl. No. 17/160,152 dated Dec. 14, 2022 1 page.

OPTIMAL METHODS TO FEEDBACK CONTROL AND ESTIMATE MAGNETIC FIELDS TO ENABLE A NEURAL DETECTION SYSTEM TO MEASURE MAGNETIC FIELDS FROM THE BRAIN

RELATED APPLICATION DATA

Pursuant to 35 U.S.C. § 119(e), this application claims the benefit of U.S. Provisional Patent Application 62/975,727, filed Feb. 12, 2020, and U.S. Provisional Patent Application 63/035,680, filed Jun. 5, 2020, which are expressly incorporated herein by reference.

FIELD OF THE INVENTION

The present inventions relate to methods and systems for non-invasive measurements from the human body, and in particular, methods and systems related to detecting physiological activity from the human brain, animal brain, and/or peripheral nerves.

BACKGROUND OF THE INVENTION

Measuring neural activity in the brain is useful for medical diagnostics, neuromodulation therapies, neuroengineering, and brain-computer interfacing. Conventional methods for measuring neural activity in the brain include X-Ray Computed Tomography (CT) scans, positron emission tomography (PET), functional magnetic resonance imaging (fMRI), or other methods that are large, expensive, require dedicated rooms in hospitals and clinics, and are not wearable or convenient to use.

In contrast to these techniques, one promising technique for measuring neural activity in the brain is magnetoencephalography (MEG), which is capable of non-invasively detecting neural activity in the brain without potentially harmful ionizing radiation, and without use of heavy or large equipment. Thus, MEG-based neural activity measurement systems can be scaled to wearable or portable form factors, which is especially important in brain-computer interface (BCI) applications that require subjects to interact freely within their environment. MEG operates under the principle that time-varying electrical current within activated neurons inherently generate magnetic signals in the form of a magnetic field that can be detected by very sensitive magnetometers located around the head.

Measuring the small magnetic fields emanating from the brain, and doing so non-invasively (without surgically penetrating the skin and bone of the head) and doing so with high spatial and temporal resolution, is difficult. The magnetic fields produced by the brain are small, and they are smaller still by the time they propagate out past the skull and the skin surface of the head. In comparison, the magnetic field emitted from various outside magnetic sources in the environment, including from global sources, such as the Earth's magnetic field, and from localized sources, such as electrical outlets and sockets, electrical wires or connections in the wall, and everyday electrical equipment in a home, office, or laboratory setting, far exceed the strength of the magnetic signals generated in the brain by many orders of magnitude, and has a distribution in space and time that is not known a-priori. Hence, it is a difficult challenge to extract the small desired signal from the brain, and to discriminate it from much larger unwanted magnetic field signals from the rest of the user's natural environment.

One type of system that can be used for MEG is a Superconductive Quantum Interference Device (SQUID), which is sensitive enough to measure magnetic fields as small as $5 \times 10^{-18}$ Tesla, which can be compared to magnetic fields resulting from physiological processes in animals, which may be in the range of $10^{-9}$ to $10^{-6}$ Tesla. However, SQUIDs rely on superconducting loops, and thus require cryogenic cooling, which may make it prohibitively costly and too large to be incorporated into a wearable or portable form factor. Thus, neural activity measurement systems that utilize SQUIDs may not be appropriate for BCI applications.

Optically pumped magnetometers (OPMs) have emerged as a viable and wearable alternative to cryogenic, superconducting, SQUID-based MEG systems, and have an advantage of obviating the need for cryogenic cooling, and as a result, may be flexibly placed on any part of the body, including around the head, which is especially important for BCI applications. Because cryogenic cooling is not required, OPMs may be placed within millimeters of the scalp, thereby enabling measurement of a larger signal from the brain (brain signals dissipate with distance), especially for sources of magnetic signals at shallow depths beneath the skull, as well as providing consistency across different head shapes and sizes.

OPMs optically pump a sample (usually a vapor formed of one of the alkali metals (e.g., rubidium, cesium, or potassium) due to their simple atomic structure, low melting point, and ease of pumping with readily available lasers) with circularly polarized light at a precisely defined frequency, thereby transferring polarized light to the vapor, and producing a large macroscopic polarization in the vapor in the direction of the light (i.e., the alkali metal atoms in the vapor will all have spins that are oriented in the direction of the light) that induces a magnetically sensitive state in the vapor. Once this magnetically sensitive state is established, polarized light is no longer transferred to the vapor, but instead, passes transparently through the vapor. In the presence of an ambient magnetic field, the spin orientation (or precession) of the alkali metal atoms in the optically pumped vapor will uniformly change, thereby disrupting the magnetically sensitive state, which is then subsequently reestablished by the transfer of the polarized light to the vapor. Because the transmission of light through the vapor varies as the spin precession of the alkali metal atoms in the vapor (and thus the magnetically sensitive state) changes in response to changes in the ambient magnetic field, the transmission of light (either the pumping light or a separate probe light) through the vapor represents a magnetic field-dependent signal (i.e., a MEG signal) that may be detected, thereby providing a measure of magnitude changes in the magnetic field.

To maintain the magnetically sensitive state of the vapor, it is important that spin relaxation due to spin exchange collisions be suppressed. In low magnetic fields (<10 nT), spin relaxation due to spin exchange collisions can be suppressed greatly, and thus, some OPMs are operated as zero-field magnetometers or Spin Exchange Relaxation Free (SERF) OPMs (referred to as "SERF OPMs"), thereby allowing for very high magnetometer sensitivities. Furthermore, because OPM measurements can be quite sensitive to low-frequency noise, the polarization of the vapor may be modulated to move the MEG signal away from the low-frequency end of the spectrum. SERF OPMs typically amplitude modulate the vapor polarization using magnetic coils that generate oscillating magnetic fields that vary at a frequency (e.g., 2000 Hz) much greater than the relaxation rate of the vapor (approximately 100 Hz). The amplitude modulated MEG signal can then be demodulated using lock-in detection to recover the MEG signal.

Although SERF OPMs allow for very high magnetometer sensitivities, they have a small dynamic range and bandwidth compared to SQUIDs, and can thus only operate in small magnetic fields (tens of nT, and often lower, to stay in the linear range of the OPMs). This becomes problematic when attempting to detect a very weak neural activity-induced magnetic field from the brain against an outside magnetic field.

For example, referring to FIG. 1, the magnitude of the magnetic field generated by a human brain (i.e., the MEG signal) may range from below 5 fT to just below 1 pT, while the magnitude of the outside magnetic field, including the Earth's magnetic field, may range from just above 5 µT to 100 µT. It should be appreciated that Earth's magnetic field covers a large range as it depends on the position of the Earth, as well as the materials of the surrounding environment where the magnetic field is measured. There are also magnetic fields from electrical power lines, everyday electric objects (microwaves, fridges, cell phones), and their interaction with magnetizable objects (metal chair legs, tables, metal posts, wall rebar, etc.). In the United States these magnetic fields appear at 60 Hz and its harmonics (120 Hz, 180 Hz, etc.) and can range in amplitude from about 500 nT to below 10 nT. In Europe electrical power is at 50 Hz, with harmonics at 100 Hz, 150 Hz, etc., and similar magnitudes.

The approximate operating range of a SERF OPM (i.e., the range in which the metallic alkali vapor resonates) extends from below 1 fT up to 200 nT. Outside of this range, the metallic alkali vapor in the OPM loses sensitivity to magnetic fields. In contrast, the approximate operating range of a less sensitive sensor, such as a flux gate magnetometer, extends from around 100 fT to close to 100 µT. Thus, in contrast to flux gate magnetometers, the limited dynamic range of a SERF OPM presents a challenge in measuring signals having a high dynamic range, e.g., approximately $2 \times 10^{10}$, which corresponds to the ratio of the lower range magnitude of the MEG signal (approximately 5 fT) to the higher range magnitude of the outside magnetic field (approximately 100 µT).

Thus, to take advantage of SERF OPMs for MEG, the outside magnetic field must be suppressed to near-zero. Otherwise, the SERF OPM cannot operate. One conventional technique for suppressing the outside magnetic field involves using large, immobile, and expensive magnetically shielded rooms to passively isolate the SERF OPMs from the sources of the outside magnetic field, effectively reducing the dynamic range requirements of the SERF OPMs used to measure the weak MEG signals.

These shielded rooms, however, are generally not viable for the consumer market, especially with regard to BCI applications, where it desirable that the MEG-based neural activity measurement system be incorporated into a wearable or portable form factor. Thus, for BCI applications, SERF OPMs must be capable of operating in the ambient background magnetic field of the native environment, including the Earth's magnetic field and other local sources of magnetic fields.

Another technique for suppressing the outside magnetic field without using magnetically shielded rooms involves incorporating a direct broadband feedback control system to actively null the outside magnetic field at the SERF OPM. In this case, the system actuators attempt to cancel the entire bandwidth of the outside magnetic field by applying a noise-cancelling, broadband, magnetic field to the sensors. However, such feedback control for OPM systems has not been implemented in a wearable system.

There, thus, remains a need to provide means for more effectively suppressing an outside magnetic field in a wearable neural detection system.

SUMMARY OF THE INVENTION

In accordance with a first aspect of the present inventions, an active shield magnetometry system comprises at least one magnetic field actuator configured for generating an actuated magnetic field that at least partially cancels an outside magnetic field, thereby yielding a total residual magnetic field. The active shield magnetometry system further comprises a plurality of magnetometers respectively configured for measuring the total residual magnetic field and outputting a plurality of total residual magnetic field measurements. The active shield magnetometry system further comprises at least one feedback control loop comprising at least one optimal linear controller (e.g., one of a linear quadratic regulator (LQR) controller, an H2 controller, and an Hinfinity controller) configured for controlling the actuated magnetic field at least partially based on at least one of the plurality of total residual magnetic field measurements respectively output by at least one of the plurality of magnetometers.

In one embodiment, the active shield magnetometry system comprises a processor containing the feedback control loop(s). In another embodiment, each of the optimal linear controller(s) is configured for controlling the actuated magnetic field in a manner that suppresses the total residual magnetic field at least one of the plurality of magnetometers. In this embodiment, each of the optimal linear controller(s) is configured for controlling the actuated magnetic field in a manner that minimizes a performance metric that includes a magnitude of the suppressed total residual magnetic field at the magnetometer(s) and a magnitude of the control effort of the optimal linear controller(s). The total performance metric may further include a magnitude of a time-integral of the suppressed total residual magnetic field at the magnetometer(s).

In still another embodiment, the plurality of magnetometers comprises a plurality of coarse magnetometers (e.g., flux gate magnetometers) respectively configured for coarsely measuring the total residual magnetic field and outputting a plurality of coarse total residual magnetic field measurements, and a plurality of fine magnetometers (e.g., optically pumped magnetometers (OPMs)) respectively configured for finely measuring the total residual magnetic field and outputting a plurality of fine total residual magnetic field measurements. The feedback control loop(s) may comprise a coarse feedback control loop, such that the optimal linear controller(s) is configured for coarsely controlling the actuated magnetic field at least partially based on at least one of the plurality of coarse total residual magnetic field measurement(s) respectively output by at least one of the plurality of coarse magnetometers. The feedback control loop(s) comprises a fine feedback control loop, such that the optimal linear controller is configured for finely controlling the actuated magnetic field at least partially based on at least one of the plurality of fine total residual magnetic field measurements respectively output by at least one of the plurality of fine magnetometers.

In one specific implementation of this embodiment, the plurality of coarse feedback control loops are configured for coarsely controlling the actuated magnetic field respectively in a manner that suppresses the total residual magnetic field at the fine magnetometer(s) to a baseline level, such that the fine magnetometer(s) comes in-range, and the plurality of fine feedback control loops are configured finely controlling the actuated magnetic field in a manner that further suppresses the total residual magnetic field at the fine magnetometer(s) to a lower level. The coarse feedback control loop may be further configured for estimating the total residual magnetic field at at least one of the plurality of fine magnetometers based on the plurality of coarse total residual magnetic field measurements, in which case, the optimal linear controller of the coarse feedback control loop may be configured for coarsely controlling the actuated magnetic field at least partially based on the estimated total residual magnetic field at the fine magnetometer(s).

In yet another embodiment, the magnetic field actuator(s) is configured for generating an actuated magnetic field at a plurality of distinct frequencies (e.g., a frequency in the range of 0 Hz-5 Hz and at a plurality of harmonic frequencies, such as 60 Hz harmonic frequencies) that at least partially cancels an outside magnetic field at the plurality of distinct frequencies, thereby yielding the total residual magnetic field, the feedback control loop(s) comprises a plurality of feedback control loops, and the optimal linear controller(s) comprises a plurality of optimal linear controllers configured for controlling the actuated magnetic field respectively at the plurality of distinct frequencies at least partially based on at least one of the plurality of total residual magnetic field measurements respectively output by the magnetometer(s).

In yet another embodiment, the active shield magnetometry system further comprises a signal acquisition unit configured for being worn on a head of a user. The signal acquisition unit comprises a support structure, the magnetic field actuator(s) affixed to the support structure, and the plurality of magnetometers affixed to the support structure. The signal acquisition unit is configured for deriving at least one magnetoencephalography (MEG) signal respectively from at least one of the plurality of total residual magnetic field measurements. The active shield magnetometry system further comprises a signal processing unit configured for determining an existence of neural activity in the brain of the user based on the at least one MEG signal.

In accordance with a second aspect of the present inventions, an active shield magnetometry method comprises generating an actuated magnetic field that at least partially cancels an outside magnetic field, thereby yielding a total residual magnetic field at a plurality of measurement locations, measuring the total residual magnetic field at the plurality of measurement locations and outputting a plurality of total residual magnetic field measurements, and controlling the actuated magnetic field with at least one optimal linear controller (e.g., one of a linear quadratic regulator (LQR) controller, an H2 controller, and an Hinfinity controller) at least partially based on at least one of the plurality of total residual magnetic field measurements.

In one method, the actuated magnetic field is controlled in a manner that suppresses the total residual magnetic field at at least one of the plurality of measurement locations to a baseline level, such that the accuracy of at least of the plurality of total residual magnetic field measurements at the one measurement location(s) increases. The actuated magnetic field may be further controlled with the optimal linear controller in a manner that minimizes a performance metric that includes a magnitude of the suppressed total residual magnetic field at the measurement location(s) and a magnitude of the control effort of the optimal linear controller(s). The total performance metric may further include a magnitude of the time-integral of the suppressed total residual magnetic field at the measurement location(s).

In another method, measuring the total residual magnetic field and outputting a plurality of total residual magnetic field measurements comprises coarsely measuring the total residual magnetic field at a plurality of coarse measurement locations and outputting a plurality of coarse total residual magnetic field measurements, and finely measuring the total residual magnetic field at a plurality of fine measurement locations and outputting a plurality of fine total residual magnetic field measurements. Controlling the actuated magnetic field with the optimal linear controller(s) at least partially based on at least one of the plurality of total residual magnetic field measurements comprises coarsely controlling the actuated magnetic field with the optimal linear controller(s) at least partially based on at least one of the plurality of coarse total residual magnetic field measurements, and finely controlling the actuated magnetic field with the optimal linear controller(s) at least partially based on at least one of the plurality of fine total residual magnetic field measurements.

In one specific implementation of this method, the actuated magnetic field may be coarsely controlled in a manner that suppresses the total residual magnetic field at at least one of the fine measurement locations to a baseline level, and the actuated magnetic field may be finely controlled in a manner that further suppresses the total residual magnetic field at the fine measurement location(s) to a lower level. Another specific implementation of this method may further comprise estimating the total residual magnetic field at the fine measurement location(s) based on the plurality of coarse total residual magnetic field measurements, and coarsely controlling the actuated magnetic field with the optimal linear controller(s) at least partially based on the estimated total residual magnetic field at the fine measurement location(s).

In still another method, the actuated magnetic field may be generated at a plurality of distinct frequencies (e.g., a frequency in the range of 0 Hz-5 Hz and at a plurality of harmonic frequencies, such as 60 Hz harmonic frequencies) that at least partially cancels an outside magnetic field at the plurality of distinct frequencies, thereby yielding the total residual magnetic field, the optimal linear controller(s) may comprise a plurality of optimal linear controllers, and the actuated magnetic field may be controlled with the plurality of optimal linear controllers respectively at the plurality of distinct frequencies at least partially based on at least one of the plurality of total residual magnetic field measurements.

Yet another method further comprises deriving a plurality of magnetoencephalography (MEG) signals respectively from the plurality of total residual magnetic field measurements, and determining an existence of neural activity in the brain of a user based on the plurality of MEG signals.

In accordance with a third aspect of the present inventions, a system for optimizing an active shield magnetometry system comprising a plurality of magnetometers, and a plurality of magnetic field actuators, and a plurality of optimal linear controllers is provided. The system comprises a noise generator configured for outputting noise representing magnetic noise (e.g., white noise), and an outside magnetic field model configured for, in response to an input of the noise, outputting an outside magnetic field vector containing outside magnetic field strengths representing strengths of an outside magnetic field respectively at the plurality of magnetometers. In one embodiment, the outside magnetic field model is weighted at a plurality of distinct frequencies (e.g., a frequency in the range of 0 Hz-5 Hz and/or a plurality of harmonic frequencies, such as 60 Hz harmonic frequencies).

The system further comprises a magnetometer model configured for, in response to an input of a total residual magnetic field vector containing total residual magnetic field strengths representing strengths of a total residual magnetic field respectively at the plurality of magnetometers, outputting a measured total residual magnetic field vector containing measured total residual magnetic field strengths representing strengths of the total residual magnetic field respectively measured by the plurality of magnetometers. The system further comprises an actuated magnetic field model configured for, in response to an input of an actuation control vector containing actuation control strengths representing strengths of actuation control signals respectively generated by the plurality of optimal linear controllers, outputting an actuated magnetic field vector containing actuated magnetic field strengths representing strengths of the actuated magnetic field generated by the plurality of magnetic field actuators respectively at the plurality of magnetometers.

The system further comprises a first magnetic field summation function configured for, in response to an input of the outside magnetic field vector and an input of the actuated magnetic field vector, outputting the total residual magnetic field vector. The system further comprises an optimal linear control model configured for, in response to the measured total residual magnetic field vector, outputting the actuation control vector. The system further comprises weighted metric model configured for, in response to an input of the total residual magnetic field vector and an input of the actuation control vector, outputting a total performance metric vector containing weighted performance metric strengths respectively defining performances of the optimal linear control model. In one embodiment, the total performance metric vector may comprise weighted total residual magnetic field strengths and weighted actuation control strengths. In another embodiment, the total performance metric vector is frequency weighted.

In one embodiment, each of the outside magnetic field model, the magnetometer model, the actuated magnetic field model, and the optimal linear control model comprises a matrix of functions (e.g., matrix transfer functions or matrices of state-space differential equations).

The system further comprises an optimizer configured for modifying the optimal linear control model in a manner that minimizes the total performance metric vector, e.g., by using a linear optimization technique selected from one or more of a linear quadratic regulator (LQR) optimization technique, H2 optimization technique, and Hinfinity optimization technique.

In one embodiment, the plurality of magnetometers comprises a plurality of coarse magnetometers and a plurality of fine magnetometers. The weighted metric model is configured for, in response to an input of the actuation control vector and the input of only total residual magnetic field strengths in the total residual magnetic field vector representing strengths of the total residual magnetic field respectively at the plurality of fine magnetometers, outputting the total performance metric vector. The actuated magnetic field model is configured for, in response to the input of the actuation control vector, outputting the actuated magnetic field vector containing only actuated magnetic field strengths representing the actuated magnetic field generated by the plurality of magnetic field actuators respectively at the plurality of fine magnetometers.

In this embodiment, the system may further a magnetic field selection function configured for, in response to an input of the total residual magnetic field vector, outputting a fine total residual magnetic field vector containing fine total residual magnetic field strengths representing the total residual magnetic field respectively at the plurality of fine magnetometers, such that the total residual magnetic field vector input into the weighted metric model is the fine total residual magnetic field vector. In this embodiment, the system may further comprise a magnetic field integration function configured for, in response to the fine total residual magnetic field vector, outputting a time-integrated total residual magnetic field vector containing time-integrated total residual magnetic field strengths representing a time-integrated total residual magnetic field respectively at the plurality of fine magnetometers. The weighted metric model may be configured for, in response to the input of the total residual magnetic field vector, the input of the actuation control vector, and an input of the time-integrated total residual magnetic field vector, outputting the total performance metric vector.

In another embodiment, the system further comprises a magnetic field estimation function configured for, in response to an input of the measured total residual magnetic field vector, outputting an estimated total residual magnetic field vector containing at least one estimated total residual magnetic field strength representing at least one strength of at least one estimate of the total residual magnetic field at at least one of the plurality of fine magnetometers. In this embodiment, the optimal linear control model is configured for, in response to an input of the estimated total residual magnetic field vector, outputting the actuation control vector. In this embodiment, the plurality of magnetometers may comprise a plurality of coarse magnetometers and a plurality of fine magnetometers, and the magnetic field estimation function may be configured for determining if each of the measured total residual magnetic field strengths representing strengths of the total residual magnetic field respectively measured by the plurality of fine magnetometers is in-range, and in response to the input of the measured total residual magnetic field vector containing only measured total residual magnetic field strengths representing strengths of the total residual magnetic field respectively measured by the plurality of coarse magnetometers and strengths of the total residual magnetic field respectively measured by the plurality of fine magnetometers that are determined to be in-range, outputting the estimated total residual magnetic field vector.

In still another embodiment, the system further comprises a pre-magnetometer noise model configured for, in response to an input of the noise, outputting a pre-magnetometer noise vector containing pre-magnetometer noise strengths representing strengths of pre-magnetometer noise at the plurality of magnetometers, and a second magnetic field summation function configured for, in response to an input of the total residual magnetic field vector and an input of the pre-magnetometer noise vector, outputting a noisy total residual magnetic field vector containing noisy total residual magnetic field strengths representing strengths of a noisy total residual magnetic field respectively at the plurality of magnetometers with pre-magnetometer noise. The magnetometer model is configured for, in response to an input of the noisy total residual magnetic field vector, outputting the measured total residual magnetic field vector. The system further comprises a post-magnetometer noise filter function configured for, in response to an input of the noise, outputting a post-magnetometer noise vector containing post-magnetometer noise strengths representing strengths of post-magnetometer noise at the plurality of magnetometers, and a third magnetic field summation function configured for, in response to an input of the measured total residual magnetic field vector and an input of the post-magnetometer noise vector, outputting a noisy measured total residual magnetic field vector containing noisy measured total residual magnetic field representing strengths of the noisy total residual magnetic field respectively measured by the plurality of magnetometers with post-magnetometer noise. The optimal linear control model are configured for, in response to the noisy measured total residual magnetic field vector, outputting the actuation control vector.

In this embodiment, the system may further comprise a pre-actuator noise model configured for, in response to an input of the noise, outputting a pre-actuator noise vector containing pre-actuator noise strengths representing strengths of pre-actuator noise at the plurality of magnetic field actuators, and a fourth magnetic field summation function configured for, in response to an input of the actuation control vector and an input of the pre-actuator noise vector, outputting a noisy actuation control vector containing noisy actuation control strengths representing strengths of the actuation control signals respectively output by the plurality of optimal linear controllers with pre-actuator noise. The actuated magnetic field model is configured for, in response to an input of the noisy actuation control vector, outputting the actuated magnetic field vector. The system may further comprise a post-actuator noise model configured for, in response to an input of the noise, outputting a post-actuator noise vector containing post-actuator noise strengths representing strengths of the post-actuator noise at the plurality of magnetic field actuators, and a fifth magnetic field summation function configured for, in response to an input of the actuated magnetic field vector and an input of the post-actuator noise vector, outputting a noisy actuated magnetic field vector containing noisy actuated magnetic field strengths representing strengths of a noisy actuated magnetic field at the plurality of magnetometers with post-actuator noise. The first magnetic field summation function is configured for, in response to the input of the outside magnetic field vector and an input of the noisy actuated magnetic field vector, outputting the total residual magnetic field vector.

In yet another embodiment, the actuated magnetic field model comprises a magnetic field actuator model configured for, in response to the input of the actuation control vector, outputting an actuation vector containing actuation strengths representing actuation strengths of the magnetic field actuators, and a matrix of influence configured for, in response to an input of the actuation vector, outputting the actuated magnetic field vector.

In accordance with a fourth aspect of the present inventions, a method of optimizing an active shield magnetometry system comprising a plurality of magnetometers, a plurality of magnetic field actuators, and a plurality of optimal linear controllers is provided.

The method comprises generating a dynamic map of the active shield magnetometry system. The dynamic map includes an outside magnetic field model of an outside magnetic field, a magnetometer model of the plurality of magnetometers, an actuated magnetic field model of an actuated magnetic field generated by the plurality of magnetic field actuators, a first magnetic field summation function, an optimal linear control model of the plurality of optimal linear controllers, and a weighted metric model. In one embodiment, each of the outside magnetic field model, the magnetometer model, the actuated magnetic field model, and the optimal linear control model comprises a matrix of functions (e.g., matrix transfer functions or matrices of state-space differential equations).

The method further comprises generating noise representing strengths of magnetic noise (e.g., white noise), and inputting the noise into the outside magnetic field model, thereby yielding an outside magnetic field vector containing outside magnetic field strengths representing strengths of the outside magnetic field respectively at the plurality of magnetometers. In one method, the outside magnetic field model is weighted at a plurality of distinct frequencies (e.g., a frequency in the range of 0 Hz-5 Hz and/or a plurality of harmonic frequencies, such as 60 Hz harmonic frequencies).

The method further comprises inputting a total residual magnetic field vector, containing total residual magnetic field strengths representing strengths of a total residual magnetic field respectively at the plurality of magnetometers, into the magnetometer model, thereby yielding a measured total residual magnetic field vector containing measured total residual magnetic field strengths representing strengths of the total residual magnetic field respectively measured by the plurality of magnetometers.

The method further comprises inputting an actuation control vector, containing actuation control strengths representing actuation control signals respectively generated by the plurality of optimal linear controllers, into the actuated magnetic field model, thereby yielding an actuated magnetic field vector containing actuated magnetic field strengths representing strengths of the actuated magnetic field generated by the plurality of magnetic field actuators respectively at the plurality of magnetometers. The method further comprises inputting the outside magnetic field vector and the actuated magnetic field vector into the first magnetic field summation function, thereby yielding the total residual magnetic field vector. The method further comprises outputting the actuation control vector from the optimal linear control model in response to the output of the measured total residual magnetic field vector by the magnetometer model.

The method further comprises inputting the total residual magnetic field vector and the actuation control vector into the weighted metric model, thereby yielding a total performance metric vector containing weighted performance metric strengths respectively defining performances of the plurality of optimal linear control model. In one embodiment, the total performance metric vector comprises weighted total residual magnetic field strengths and weighted actuation control strengths. In another embodiment, the total performance metric vector is frequency weighted.

The method further comprises modifying the optimal linear control model in a manner that minimizes the total performance metric vector. In one embodiment, the optimal linear control model is modified in accordance with a linear optimization technique selected from one or more of a linear quadratic regulator (LQR) optimization technique, H2 optimization technique, and Hinfinity optimization technique.

In one method, plurality of magnetometers comprises a plurality of coarse magnetometers and a plurality of fine magnetometers. Inputting the total residual magnetic field vector into the weighted metric model comprises inputting only total residual magnetic field strengths in the total residual magnetic field vector, representing strengths of the total residual magnetic field respectively at the plurality of fine magnetometers, into the weighted metric model, and the actuated magnetic field vector output by the actuated magnetic field model contains only actuated magnetic field strengths representing the actuated magnetic field generated by the plurality of magnetic field actuators respectively at the plurality of fine magnetometers.

In this method, the dynamic map may further include a magnetic field selection function, in which case, the method may further comprise inputting the total residual magnetic field vector into the magnetic field selection function, thereby yielding a fine total residual magnetic field vector containing fine total residual magnetic field strengths representing the total residual magnetic field respectively at the plurality of fine magnetometers. The total residual magnetic field vector input into the weighted metric model is the fine total residual magnetic field vector. The dynamic map may further include a magnetic field integration function, in which case, the method may further comprise inputting the fine total residual magnetic field vector into the magnetic field integration function, thereby yielding a time-integrated total residual magnetic field vector containing time-integrated total residual magnetic field strengths representing a time-integrated total residual magnetic field respectively at the plurality of fine magnetometers, and inputting the time-integrated total residual magnetic field vector, along with the total residual magnetic field vector and the actuation control vector, into the weighted metric model, thereby yielding the total performance metric vector.

In another method, the dynamic map further includes a magnetic field estimation function, in which case, the method further comprises inputting the measured total residual magnetic field vector into the magnetic field estimation function, thereby yielding an estimated total residual magnetic field vector containing at least one estimated total residual magnetic field strength representing at least one strength of at least one estimate of the total residual magnetic field at at least one of the plurality of fine magnetometers, and inputting the estimated total residual magnetic field vector into the optimal linear control model, thereby yielding the actuation control vector. This method may further comprise determining if each of the measured total residual magnetic field strengths representing strengths of the total residual magnetic field respectively measured by the plurality of fine magnetometers is out-of-range. The estimated total residual magnetic field vector may be derived from the measured total residual magnetic field vector containing only measured total residual magnetic field strengths representing strengths of the total residual magnetic field respectively measured by the plurality of coarse magnetometers and strengths of the total residual magnetic field respectively measured by the plurality of fine magnetometers that are determined to be in-range.

In still another method, the dynamic map further comprises a pre-magnetometer noise model of pre-magnetometer noise at the plurality of magnetometers, a second summation function, a post-magnetometer noise model of post-magnetometer noise at the plurality of magnetometers, and a third summation function. The method further comprises inputting the noise into the pre-magnetometer noise model, thereby yielding a pre-magnetometer noise vector containing pre-magnetometer noise strengths representing strengths of the pre-magnetometer noise at the plurality of magnetometers, and inputting the total residual magnetic field vector and the pre-magnetometer noise vector into the second summation function, thereby yielding a noisy total residual magnetic field vector containing noisy total residual magnetic field strengths representing strengths of a noisy total residual magnetic field respectively at the plurality of magnetometers with pre-magnetometer noise. Inputting the total residual magnetic field vector into the magnetometer model comprises inputting the noisy total residual magnetic field vector into the magnetometer model, thereby yielding the measured total residual magnetic field vector. The method further comprises inputting the noise into the post-magnetometer noise model, thereby yielding a post-magnetometer noise vector containing post-magnetometer noise strengths representing strengths of the post-magnetometer noise at the plurality of magnetometers, and inputting the measured total residual magnetic field vector and the post-magnetometer noise vector into the third summation function, thereby yielding a noisy measured total residual magnetic field vector containing noisy measured total residual magnetic field representing strengths of the noisy total residual magnetic field respectively measured by the plurality of magnetometers with post-magnetometer noise. The actuation control vector is output from the optimal linear control model in response to the noisy measured total residual magnetic field vector.

In this method, the dynamic map may further comprise a pre-actuator noise model of pre-actuator noise at the plurality of magnetic field actuators, a fourth summation function, a post-actuator noise model of post-actuator noise at the plurality of magnetic field actuators, and a fifth summation function. The method may further comprise inputting the noise into the pre-actuator noise model, thereby yielding a pre-actuator noise vector containing pre-actuator noise strengths representing strengths of the pre-actuator noise at the plurality of magnetic field actuators, and inputting the actuation control vector and the pre-actuator noise vector into the fourth summation function, thereby yielding a noisy actuation control vector containing noisy actuation control strengths representing strengths of the actuation control signals respectively output by the plurality of optimal linear controllers with pre-actuator noise. This method further comprises inputting the actuation control vector into the actuator model comprises inputting the noisy actuation control vector into the actuator model, thereby yielding the actuated magnetic field vector, inputting the noise into the post-actuator noise model, thereby yielding a post-actuator noise vector containing post-actuator noise strengths representing strengths of the post-actuator noise at the plurality of magnetic field actuators, and inputting the actuated magnetic field vector and the post-actuator noise vector into the fifth summation function, thereby yielding a noisy actuated magnetic field vector containing noisy actuated magnetic field strengths representing strengths of a noisy actuated magnetic field at the plurality of magnetometers with post-actuator noise. The outside magnetic field vector and the noisy actuated magnetic field vector are summed, thereby yielding the total residual magnetic field vector.

In yet another method, the actuated magnetic field model of the dynamic map comprises a magnetic field actuator model and a matrix of influence. The method comprises inputting the actuation control vector into the magnetic field actuator model, thereby yielding an actuation vector containing actuation strengths representing actuation strengths of the magnetic field actuators, and inputting the actuation vector into the matrix of influence, thereby yielding the actuated magnetic field vector.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the present inventions and are not therefore to be considered limiting of its scope, the present inventions will be described and explained with additional specificity and detail through the use of the accompanying drawings in which.

DETAILED DESCRIPTION OF THE EMBODIMENTS

Significantly, the neural activity measurement systems (and variations thereof) described herein are configured for non-invasively acquiring magnetoencephalography (MEG) signals from a brain of a user while effectively suppressing an outside magnetic field without the use of magnetically shielded rooms, and identifying and localizing the neural activity within the cortical structures of the brain of the user based on the acquired magnetoencephalography (MEG) signals.

The neural activity measurement system described herein may take the form of a brain computer interface (BCI) (also known as a neural-controlled interface (NCI), mind-machine interface (MMI), direct neural interface (DNI), or brain-machine interface (BMI)), which converts the neural activity information into commands that are output to an external device or devices for carrying out desired actions that replace, restore, enhance, supplement, or improve natural central nervous system (CNS) output, and thereby changes the ongoing interactions between the CNS of a user and an external or internal environment.

Figure 1:
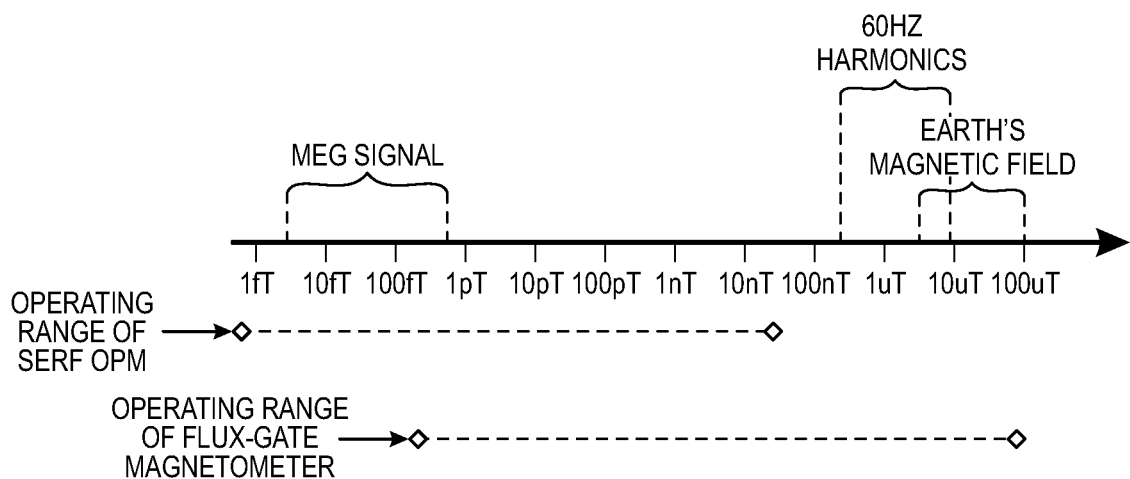
FIG. 1 is a diagram of illustrating dynamic ranges of a magnetoencephalography (MEG) signal and a typical outside magnetic field, and the operating ranges of a Spin Exchange Relaxation Free (SERF) optically-pumped magnetometer (OPM) and flux gate magnetometer, plotted on a magnetic spectrum.
Figure 2:
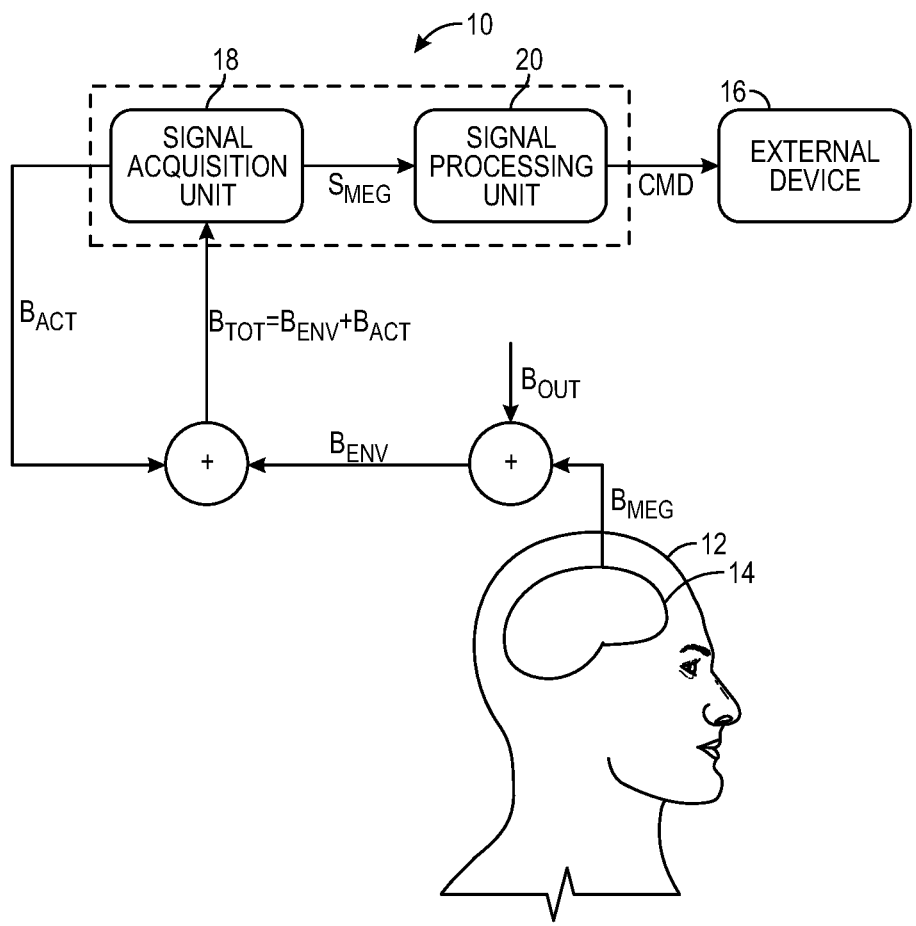
FIG. 2 is a block diagram of a neural activity measurement system constructed in accordance with one embodiment of the present inventions, particularly shown in the context of a brain computer interface (BCI)

For example, as illustrated in FIG. 2, one embodiment of a neural activity measurement system 10 constructed in accordance with the present inventions will be described. The neural activity measurement system 10 is configured for measuring neural activity in the brain 14 of a user 12, generating commands CMD in response to the measured neural activity information, and sending the commands CMD to an external device 16 in the context of a BCI.

To this end, the neural activity measurement system 10 generally comprises a signal acquisition unit 18 configured for at least partially cancelling a relatively strong outside magnetic field $B_{OUT}$ within an environmental magnetic field $B_{ENV}$ that also includes a relatively weak MEG magnetic field $B_{MEG}$ induced by electrical current (indicative of neural activity) in a brain 14 of a user 12. That is, $B_{TOT}=B_{ENV}+B_{ACT}=B_{OUT}+B_{MEG}+B_{ACT}$ The outside magnetic field $B_{OUT}$ may emanate from global sources (e.g., the Earth's magnetic field), and from localized sources, including, but not limited to, from electromagnetic radiation emanating from electrical outlets and sockets, electrical wires or connections in the wall, and everyday electrical equipment (microwave ovens, televisions, refrigerators, environmental systems (air conditioning, etc.) in a home, office, or laboratory setting, as well as from cell phones, biomagnetics unrelated to neural signals (such as facial muscles, magnetic fields produced by the heart or nerves firing), everyday objects encountered inside (metal and magnetic objects, including steel supports, rebar, studs, utility boxes, etc.,) and outside spaces, such as cell phone towers, power lines, transformers, and moving vehicles (e.g., cars, trains, bikes, electric bikes and scooters, electric cars, etc.), user motion/rotation/translation in a background field (earth field), user clothing and eyeglasses, personal electronics (e.g., laptop computers, watches, phones, smart rings, etc.), active implantable medical devices (pacemakers), augmented reality/virtual reality, sound systems (that use magnets), etc.

To this end, the neural activity measurement system 10 generally comprises a signal acquisition unit 18 configured for at least partially cancelling a relatively strong outside magnetic field $B_{OUT}$ within an environmental magnetic field $B_{ENV}$ that also includes a relatively weak MEG magnetic field $B_{MEG}$ induced by electrical current (indicative of neural activity) in a brain 14 of a user 12. The signal acquisition unit 18 is further configured for detecting the total residual magnetic field $B_{TOT}$ as feedback to cancel the outside magnetic field $B_{OUT}$. The signal acquisition unit 18 is also configured for extracting and outputting a clean (i.e., reduced-noise) electrical MEG signals $S_{MEG}$ of the MEG magnetic field $B_{MEG}$ from the total residual magnetic field $B_{TOT}$.

The signal acquisition unit 18 may utilize any suitable technique for acquiring the MEG magnetic field $B_{MEG}$, including, but not limited to the techniques described in U.S. Patent Application Ser. No. 16/428,871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418,500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(s)," (now U.S. Pat. No. 10,627,460), U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Application Ser. No. 62/858,636, entitled "Integrated Magnetometer Arrays for Magnetoencephalography (MEG) Detection Systems and Methods," U.S. Provisional Application Ser. No. 62/836,421, entitled "Systems and Methods for Suppression of Non-Neural Interferences in Magnetoencephalography (MEG) Measurements," U.S. Provisional Application Ser. No. 62/842,818 entitled "Active Shield Arrays for Magnetoencephalography (MEG)," U.S. Provisional Application Ser. No. 62/926,032 entitled "Systems and Methods for Multiplexed or Interleaved Operation of Magnetometers," U.S. Provisional Application Ser. No. 62/896,929 entitled "Systems and Methods having an Optical Magnetometer Array with Beam Splitters," and U.S. Provisional Application Ser. No. 62/960,548 entitled "Methods and Systems for Fast Field Zeroing for Magnetoencephalography (MEG)," which are all expressly incorporated herein by reference.

The neural activity measurement system 10 further comprises a signal processing unit 20 configured for processing the electrical MEG signal $S_{MEG}$ to identify and localize neural activity within the cortex of the brain 14 of the user 12, and issuing the commands CMD to the external device 16 in response to the identified and localized neural activity in the brain 14 of the user 12.

It should be appreciated that, although the neural activity measurement system 10 is described herein in the context of a BCI, the present inventions should not be so limited, and may be applied to any system used for any application (including, but not limited to, medical, entertainment, neuromodulation stimulation, lie detection devices, alarm, educational, etc.), where it is desirable to perform measurements on a magnetic field induced by any physiological process in a person that would benefit from cancelling the outside magnetic field $B_{OUT}$. For example, instead of deriving neural activity information from MEG signals, magnetic fields induced by electrical heart activity can be measured to determine heart activity information of a person.

Furthermore, it should also be appreciated that, although the use of the signal acquisition unit lends itself well to neural activity measurement systems, the signal acquisition unit 18 may find use in other applications, such as, e.g., other types of biomedical sensing, vehicle navigation, mineral exploration, non-destructive testing, detection of underground devices, asteroid mining, space exploration, etc. Thus, signal acquisition unit 18 can be adapted to measure neural signals generated from non-brain anatomical structures, as well as other types of biological signals and non-biological signals.

Figure 3:
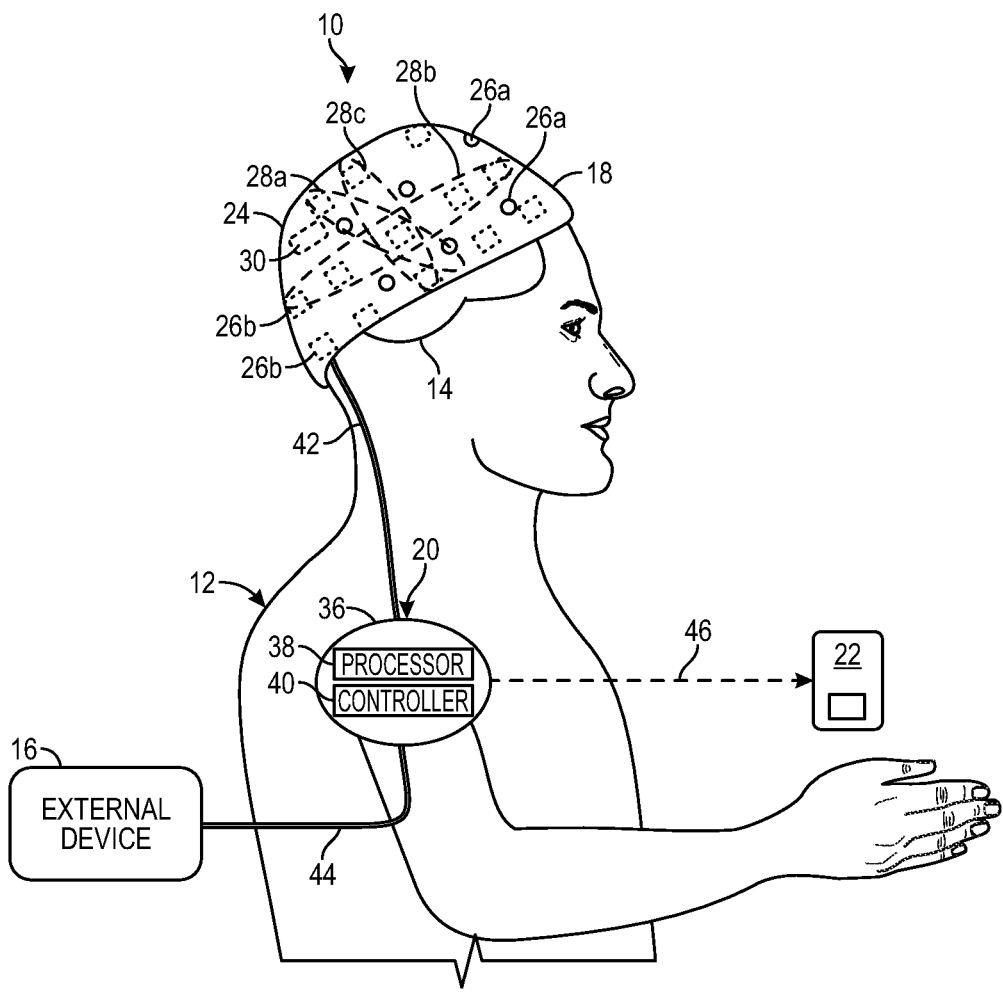
FIG. 3 is a side view of a physical implementation of the BCI of FIG. 2.

Referring now to FIG. 3, an exemplary physical implementation of the neural activity measurement system 10 will be described.

As shown, the signal acquisition unit 18 is configured for being applied to the user 12, and in this case, worn on the head of the user 12. The signal acquisition unit 18 comprises a support structure 24, a plurality of magnetometers 26 (divided between a plurality of coarse magnetometers 26a and a plurality of fine magnetometers 26b) distributed about the support structure 24, a set of magnetic field actuators 28 in proximity to the fine magnetometers 26b, and a processor 30 electrically coupled between the magnetometers 26 and the set of actuators 28.

The support structure 24 may be shaped, e.g., have a banana, headband, cap, helmet, beanie, other hat shape, or other shape adjustable and conformable to the user's head, such that at least some of the magnetometers 26 are in close proximity, preferably in contact, with the outer skin of the head, and in this case, the scalp of the user 12. The support structure 24 may be made out of any suitable cloth, soft polymer, plastic, hard shell, and/or any other suitable material as may serve a particular implementation. An adhesive, strap, or belt (not shown) can be used to secure the support structure 24 to the head of the user 12.

Each of the magnetometers 26 is configured for detecting a spatial component of the total residual magnetic field $B_{TOT}$, and outputting a corresponding electrical signal representative of the spatial component of the total residual magnetic field $B_{TOT}$. In the illustrated embodiment, the plurality of coarse magnetometers 26a is distributed on the outside of the support structure 24 for detecting the respective spatial components of the total residual magnetic field $B_{TOT}$ mainly from outside of the support structure 24, whereas the plurality of fine magnetometers 26b is distributed on the inside of the support structure 24 for detecting the respective spatial components of the total residual magnetic field $B_{TOT}$ mainly from inside the support structure 24 (i.e. they are closer to the brain 14 of the user 12).

Each of the coarse magnetometers 26a has a relatively low sensitivity, but high dynamic sensitivity range, to magnetic fields, whereas each of the fine magnetometers 26b has a relatively high sensitivity, but low dynamic sensitivity range. The signal acquisition unit 18 may have any suitable number of magnetometers 26. For example, the signal acquisition unit 18 may have twelve coarse magnetometers 26a and twenty-five fine magnetometers 26b, although one of ordinary skill in the art would understand that signal acquisition unit 18 may have any suitable number of coarse magnetometers 26a and magnetometers 26b, including more coarse magnetometers 26a then fine magnetometers 26b. In alternative embodiments of the signal acquisition unit 18, the plurality of magnetometers 26 may only comprise a plurality of fine magnetometers 26b distributed on the inside of the support structure 24.

In the illustrated embodiment, each coarse magnetometer 26a takes the form of a flux gate magnetometer, which has a relatively low sensitivity (e.g., on the order of 100 fT), and thus, may not be capable of measuring weak magnetic fields generated by neural activity in the brain 14 of the user 12. However, a flux gate magnetometer has a relatively high dynamic sensitivity range (in the range of 100 fT to close to 100 µT), and thus, may operate in a large outside magnetic field $B_{OUT}$. Although each of the coarse magnetometers 26a are described as taking the form of a flux gate magnetometer, other types of coarse magnetometers can be used, including, but not limited to, anisotropic magnetoresistance (AMR) sensors, tunnel magnetoresistance (TMR) sensors, Hall-effect sensors, nitrogen vacancy sensors, or any other magnetometer that can operate in a linear range over the amplitude range of a typical outside magnetic field $B_{OUT}$. As will be described in further detail below, each of the coarse magnetometers 26a is specifically designed to facilitate the calibration of its offset and gain using novel pre-calibration and dynamic calibration techniques.

In the illustrated embodiment, each fine magnetometer 26b takes the form of a Spin Exchange Relaxation Free (SERF) Optically Pumped Magnetometer (OPM). Although a SERF OPM has a relatively small dynamic range (e.g., in the range of 1 ft to 200 nT), it has a relatively high sensitivity (on the order of 1 fT) to magnetic fields compared to flux gate magnetometers. Further details of SERF OPMs are described in U.S. Provisional Application Ser. No. 62/975, 693, entitled "Nested and Parallel Feedback Control Loops For Ultra-Fine Measurements of Magnetic Fields From the Brain Using a Wearable MEG System", which is expressly incorporated herein by reference.

In the illustrated embodiment, each of the coarse magnetometers 26a and fine magnetometers 26b are vector magnetometers that are capable of detecting the total residual magnetic field $B_{TOT}$ in three dimensions (x, y, and z). For example, each of the coarse magnetometers 26a may include a triad of the scalar magnetometers, as described in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", and each of the fine magnetometer 26b may be vector magnetometers, as described in U.S. patent application Ser. No. 16/752,393, entitled "Neural Feedback Loop Filters for Enhanced Dynamic Range Magnetoencephalography (MEG) Systems and Methods," which are expressly incorporated herein by reference.

The clean (i.e., reduced-noise) electrical MEG signals $S_{MEG}$ that are representative of the spatial components of the MEG magnetic field $B_{MEG}$, and that will be processed by the signal processing unit 20 for determining and localizing neural activity in the brain 14 of the user 12, will be respectively derived from the electrical signals output by the respective fine magnetometers 26b, and in some cases, from the electrical signals output by the coarse magnetometers 26a; whereas the characteristics (namely amplitude and phase) of the actuated magnetic field $B_{ACT}$ will be derived from the electrical signals output by the respective coarse magnetometers 26a and/or the electrical signals output by at least some of the respective fine magnetometers 26b.

The set of magnetic field actuators 28 is configured for generating the actuated magnetic field $B_{ACT}$ to at least partially cancel the outside magnetic field $B_{OUT}$ in the vicinity of the plurality of fine magnetometers 26b. The set of magnetic field actuators 28 may, e.g., comprise at least one coil and at least one driver that drives the coil(s) with electrical current at a defined amperage, voltage, or some other variable, and at a defined frequency, thereby setting the actuation strengths of the magnetic field actuators 28. In the illustrated embodiment, the set of magnetic field actuators 28 comprises a triad of uniform magnetic field actuators 28a-28c for respectively generating x-, y-, and z-components of the actuated magnetic field $B_{ACT}$ to cancel the outside magnetic field $B_{OUT}$ in all three dimensions. In an optional embodiment, the set of magnetic field actuators 28 may also comprise six gradient magnetic field actuators (not shown) for generating first-order x-, y-, and z-gradient components of the actuated magnetic field $B_{ACT}$. One of ordinary skill in the art would appreciate that the set of field actuators 28 may include any suitable and type of magnetic field actuators capable of cancelling the outside magnetic field $B_{OUT}$ at the magnetometers 26.

The processor 30 is electrically coupled between the magnetometers 26 and magnetic field actuators 28 via electrical wires (not shown), and is configured for processing the electrical signals respectively output by the coarse magnetometers 26a (and in some cases the electrical signals output by the fine magnetometers 26b) in response to the detection of the spatial components of the total residual magnetic field $B_{TOT}$, determining the characteristics of the actuated magnetic field $B_{ACT}$ required to cancel the outside magnetic field $B_{OUT}$ in the total residual magnetic field $B_{TOT}$, and generating actuation control signals based on this determination that are output to the set of magnetic field actuators 28. Further details discussing novel techniques for cancelling the outside magnetic field $B_{OUT}$ in the total residual magnetic field $B_{TOT}$ are described in U.S. Provisional Application Ser. No. 62/975,693, entitled "Nested and Parallel Feedback Control Loops For Ultra-Fine Measurements of Magnetic Fields From the Brain Using a Wearable MEG System".

To minimize the size, weight, and cost of the signal acquisition unit 18, the functions of the processor 30 are preferably performed digitally (e.g., in firmware, such as a programmable logic device (e.g., a field programmable gate array (FPGA), or an ASIC (application specific integrated circuit) device, or in a micro-processor)), in which case, one or more analog-to-digital converters (not shown) can be employed between the magnetometers 26 and the processor 30, and one or more digital-to-analog converters (not shown) can be employed between the magnetic field actuators 28 and the processor 30. However, it should be appreciated that, in alternative embodiments, the functions of the processor 30 may be at least partially performed in an analog fashion.

It should be noted that, although the signal acquisition unit 18 is illustrated in FIG. 3 as having a single set of magnetic field actuators 28 and a single processor 30, the signal acquisition unit 18 may comprise more than one set of magnetic field actuators 28 and more than one processor 30. In this case, each set of magnetic field actuators 28 and each corresponding processor 30 may be associated with a subset of magnetometers 26. In one embodiment, the fine magnetometers 26b, set(s) of magnetic field actuators 28, and processor(s) 30 may be fabricated as integrated module(s). For example, each integrated module may comprise a rectangular substrate containing a subset or all of the fine magnetometers 26b, a set of the magnetic field actuators 28 incorporated into the rectangular substrate, such that coils of the magnetic field actuators 28 respectively wrap around the orthogonal dimensions of the rectangular substrate, and the processor 30 affixed to the surface of the rectangular substrate between the coils.

The signal processing unit 20 is configured for being applied to the user 12, and in this case, worn remotely from the head of the user 12, e.g., worn on the neck, shoulders, chest, or arm) of the user 12. The signal processing unit 20 comprises a housing 36 containing its own processor 38 and a controller 40. The processor 38 is configured for identifying and localizing neural activity within the cortex of the brain 14 of the user 12, and the controller 40 is configured for issuing commands CMD to an external device 16 in response to the identified and localized neural activity in the brain 14 of the user 12, as well as controlling the high-level operational functions of the signal acquisition unit 18. The signal processing unit 20 may additionally include a power supply (which if head-worn, may take the form of a rechargeable or non-chargeable battery), a control panel with input/output functions, a display, and memory. Alternatively, power may be provided to the signal processing unit 20 wirelessly (e.g., by induction).

In the illustrated embodiment, the neural activity measurement system 10 further comprises a wired connection 42 (e.g., electrical wires) for providing power from the signal processing unit 20 to the signal acquisition unit 18 and communicating between the signal processing unit 20 and the signal acquisition unit 18. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the signal acquisition unit 18 and/or communicating between the signal processing unit 20 and the signal acquisition unit 18.

In the illustrated embodiment, the neural activity measurement system 10 further comprises a wired connection 44 (e.g., electrical wires) for providing power from the signal processing unit 20 to the external device 16 and communicating between the signal processing unit 20 and the external device 16. Alternatively, the neural activity measurement system 10 may use a non-wired connection (e.g., wireless radio frequency (RF) signals (e.g., Bluetooth, Wifi, cellular, etc.) or optical links (e.g., fiber optic or infrared (IR)) for providing power from the signal processing unit 20 to the external device 16 and/or communicating between the signal processing unit 20 and the external device 16.

The neural activity measurement system 10 may optionally comprise a remote processor 22 (e.g., a Smartphone, tablet computer, or the like) in communication with the signal processing unit 20 coupled via a wired connection (e.g., electrical wires) or a non-wired connection (e.g., wireless radio frequency (RF) signals (e.g., Bluetooth, Wifi, cellular, etc.) or optical links (e.g., fiber optic or infrared (IR)) 46. The remote processor 22 may store data from previous sessions, and include a display screen.

It should be appreciated that at least a portion of the signal acquisition and magnetic field cancellation functionality of the processor 30 in the signal acquisition unit 18 may be implemented in the signal processing unit 20, and/or at least a portion of the neural activity determination and localization functionality of the signal processing unit 20 may be implemented in the signal acquisition unit 18. In the preferred embodiment, the functionalities of the processor 30 in the signal acquisition unit 18, as well as the processor 38 and a controller 40 in the signal processing unit 20, may be implemented using one or more suitable computing devices or digital processors, including, but not limited to, a microcontroller, microprocessor, digital signal processor, graphical processing unit, central processing unit, application specific integrated circuit (ASIC), field programmable gate array (FPGA), and/or programmable logic unit (PLU). Such computing device(s) or digital processors may be associated with non-transitory computer- or processor-readable medium that stores executable logic or instructions and/or data or information, which when executed, perform the functions of these components. The non-transitory computer- or processor-readable medium may be formed as one or more registers, for example of a microprocessor, FPGA, or ASIC, or can be a type of computer-readable media, namely computer-readable storage media, which may include, but is not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

It is desirable to optimize the performance of the signal acquisition unit 18, not only to achieve optimal cancellation of the outside magnetic field $B_{OUT}$ at the magnetometers 26, but also to minimize power consumption of the signal acquisition unit 18. However, the fundamental physics of magnetometry and the complexity of magnetic field signal propagation from the outside world and from the brain present challenges to optimizing the performance of the signal acquisition unit 18.

Existing optimal control design methods (e.g., proportional integral derivative) are not optimal for magnetometry, including wearable MEG systems to detect signals from the brain, since they are limited in performance with regard to canceling the outside magnetic field under typical conditions in everyday environments, such as in a home, office, or laboratory, and thus, do not provide sufficient performance to enable a wearable MEG system to properly measure signals from the brain. Although it is known to use optimal linear control (e.g., linear quadratic regulators (LQR), H2, Hinfinity, etc.) to optimize the performance of various systems, there is no known linear optical feedback control for a wearable MEG system for detecting signals from the brain. This is due, in large part, to the unique challenges for developing optimal control algorithms for the wearable MEG system, since the feedback control must be able to cancel a large magnetic field in the outside world to enable the fine magnetometers to measure the small magnetic field emanating from the brain of the user, while maintaining the MEG system in a compact and wearable form. Furthermore, due to the fundamental physics of magnetometry, and the complexity of magnetic field signal propagation from the outside world and the brain, optical linear control cannot be applied to a wearable MEG system in a straightforward manner.

Thus, while existing optimal control design methods may be expected to at least marginally increase the performance of the signal acquisition unit 18, without modification, they are insufficient for optimizing the performance of the signal acquisition unit 18 in a manner that allows the signal acquisition unit 18 to robustly acquire MEG signals $S_{MEG}$ in a typical environment.

Figure 4:
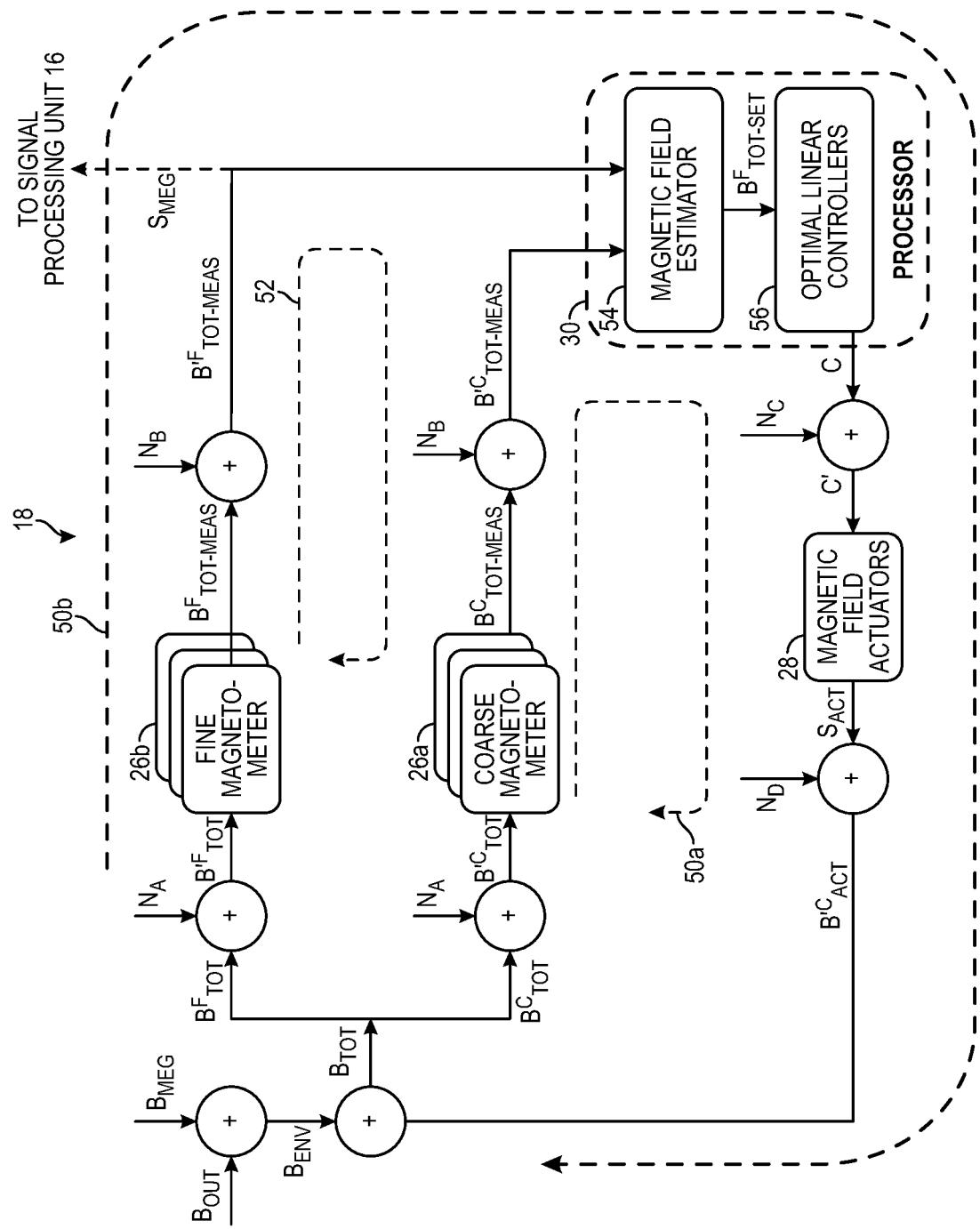
FIG. 4 is a block diagram of one exemplary embodiment of a signal acquisition unit used by the neural activity measurement system of FIG. 2.

Referring now to FIG. 4, the signal acquisition unit 18 employs an optimal linear feedback control loop 50 to optimally reject unwanted noise signals, such as the outside magnetic field $B_{OUT}$, as well as to reject unwanted noise generated by the signal acquisition unit 18 at the magnetometers 26 and magnetic field actuators 28 (including pre-magnetometer noise $N_A$ (e.g., electromagnetic noise caused by the electronics in the magnetometers 26), post-magnetometer noise $N_B$ (e.g., thermal noise in wires), pre-actuator noise $N_C$ (e.g., thermal noise in wires), and post-actuator noise $N_D$ (e.g., electromagnetic noise caused by the electronics in the magnetic field actuators 28), and will do so with reasonable control effort, thereby providing the best possible overall performance of the signal acquisition unit 18.

The pre-magnetometer noise $N_A$ combines with a total residual magnetic field $B^C_{TOT}$ at the coarse magnetometers 26a to create a noisy total residual magnetic field $B'^C_{TOT}$ with pre-magnetometer noise $N_A$ at the coarse magnetometers 26a. Each of the coarse magnetometers 26a measures a respective spatial component of the noisy total residual magnetic field $B'^C_{TOT}$ and outputs a total residual magnetic field measurement $B^C_{TOT\text{-}MEAS}$ corresponding to the spatial component of that noisy total residual magnetic field $B'^C_{TOT}$. The post-magnetometer noise $N_B$ combines with the total residual magnetic field measurements $B^C_{TOT\text{-}MEAS}$ output by the coarse magnetometers 26a to create noisy total residual magnetic field measurements $B'^C_{TOT\text{-}MEAS}$ with post-magnetometer noise $N_B$ at the processor 30.

Similarly, the pre-magnetometer noise $N_A$ combines with a total residual magnetic field $B^F_{TOT}$ at the fine magnetometers 26b to create a noisy total residual magnetic field $B'^F_{TOT}$ with pre-magnetometer noise $N_A$ at the fine magnetometers 26b. Each of the fine magnetometers 26b measures a spatial component of the noisy total residual magnetic field $B'^F_{TOT}$ and outputs a total residual magnetic field measurement $B^F_{TOT\text{-}MEAS}$ corresponding to the spatial component of that noisy total residual magnetic field $B'^F_{TOT}$. The post-magnetometer noise $N_B$ combines with the total residual magnetic field measurements $B^F_{TOT-MEAS}$ output by the fine magnetometers 26b to create noisy total residual magnetic field measurements $B'^F_{TOT-MEAS}$ with post-magnetometer noise nb at the processor 30.

In response to noisy total residual magnetic field measurements $B'^C_{TOT-MEAS}$ from the coarse magnetometers 26a and the noisy total residual magnetic field measurements $B'^F_{TOT-MEAS}$ from the fine magnetometers 26b, the processor 30 generates and outputs actuation control signals C to the magnetic field actuators 28. The pre-actuator noise $N_C$ combines with the actuation control signal C to create a noisy actuation control signal C' with pre-actuator noise $N_C$ at the magnetic field actuators 28. Each of the magnetic field actuators 28 responds to a respective noisy actuation control signal C' with an actuation strength $S_{ACT}$. The post-actuator noise $N_D$ combines with the actuation strengths $S_{ACT}$ of the magnetic field actuators 28 to create a noisy actuated magnetic field $B'_{ACT}$ with post-actuator noise $N_D$ at the magnetometers 26, which combines with the outside magnetic field $B_{OUT}$, along with the MEG magnetic field $B_{MEG}$, to create the total residual magnetic field $B_{TOT}$ at the magnetometers 26.

It should be appreciated that, in the illustrated embodiment, the coarse magnetometers 26a and fine magnetometers 26b are capable of detecting the total residual magnetic field $B_{TOT}$ in three dimensions (x, y, and z), and the set of magnetic field actuators 28 includes three magnetic field actuators 28a-28c (shown in FIG. 2) capable of generating the noisy actuated magnetic field $B'_{ACT}$ in three dimensions (x, y, and z). As such, each of the total residual magnetic field measurement $B^C_{TOT-MEAS}$ and total residual magnetic field measurement $B^F_{TOT-MEAS}$ respectively output by the coarse magnetometers 26a and fine magnetometers 26b, and by extension the noisy total residual magnetic field measurements $B'^C_{TOT-MEAS}$, output to the processor 30, and noisy total residual magnetic field measurements $B'^C_{TOT-MEAS}$, and the actuation control signals C output by the processor 30, and by extension the noisy actuation control signals C', output to the respective magnetic field actuators 28a-28c, is a vector (i.e., comprises an x-component, y-component, and z-component), such that the outside magnetic field $B_{OUT}$ can be cancelled, and thus the total residual magnetic field measurement $B^F_{TOT-MEAS}$ suppressed at the fine magnetometers 26b, in three dimensions.

For purposes that will be described in further detail below, the processor 30, in the illustrated embodiment, comprises a magnetic field estimator 54 configured for estimating the spatial components of the total residual magnetic field $B^F_{TOT}$ respectively at each fine magnetometer 26b based on the noisy total residual magnetic field measurements $B'^C_{TOT-MEAS}$ from the coarse magnetometers 26a and noisy total residual magnetic field measurements $B'^C_{TOT-MEAS}$ from fine magnetometers 26b (that are in-range), as well as on the actuation control signals C output by the processor 30, and outputting estimates $B^F_{TOT-EST}$ of the spatial components of the total residual magnetic field $B^F_{TOT}$ at the fine magnetometers 26b. The magnetic field estimator 54 may perform this estimation function using, e.g., the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", which is expressly incorporated herein by reference.

Significantly, the processor 30 comprises a plurality of optimal linear controllers 56 (e.g., a linear quadratic regulator (LQR) controller, an H2 controller, or an Hinfinity controller) configured for generating the actuation control signals C (one for each magnetic field actuator 28) in response to the noisy total residual magnetic field measurements $B'^C_{TOT-MEAS}$ from the coarse magnetometers 26a and noisy total residual magnetic field measurements $B'^C_{TOT-MEAS}$ from fine magnetometers 26b (that are in-range), and in the illustrated embodiment, in response to the total residual magnetic field estimates $B^F_{TOT-EST}$ output by the magnetic field estimator 54. In accordance with the actuation control signals C respectively output by the optimal linear controllers 56 with the pre-actuator noise $N_C$ (i.e., the noisy actuation control signals C, the magnetic field actuators 28 generate the noisy actuated magnetic field $B'_{ACT}$, which combines with the outside magnetic field $B_{OUT}$ (along with weak MEG magnetic field $B_{MEG}$ from the brain 14) to yield the total residual magnetic field $B_{TOT}$ at the magnetometers 26.

The optimal linear controllers 56 compute the actuation control signals C, such that the outside magnetic field $B_{OUT}$ is canceled by the subsequently generated noisy actuated magnetic field $B'_{ACT}$ in a manner that minimizes a performance metric, and in this case, a performance metric of magnitudes of the spatial components of the total residual magnetic field $B^F_{TOT}$ (and optionally an time-integration of the spatial components of the total residual magnetic field $B^F_{TOT}$) at the fine magnetometers 26b and a magnitude of the control effort of the optimal linear controllers 56. The performance metric may be properly weighted relative to each other to achieve a desired tradeoff between the overall desired performance of the signal acquisition unit 18 in suppressing the fine total residual magnetic field $B^F_{TOT}$ at the fine magnetometers 26b and the control effort of the signal acquisition unit 18 required to do so, as will be described in further detail below.

Although the processor 30 is illustrated as receiving input from two coarse magnetometers 26a and three fine magnetometers 26b, it should be appreciated that the processor 30 can receive input from more or less coarse magnetometers 26a, including only one coarse magnetometer 26a, and can receive input from more or less fine magnetometers 26b, including only one fine magnetometer 26b. Furthermore, although the processor 30 is illustrated as receiving input from an unequal number of coarse magnetometers 26a and fine magnetometers 26b, the processor 30 may receive input from an equal number of coarse magnetometers 26a and fine magnetometers 26b, including a number of coarse magnetometers 26a that is greater or less the number of fine magnetometers 26b.

In alternative embodiment, multiple optimal linear feedback control loops 50 may be employed to cancel the outside magnetic field $B_{OUT}$ at distinct frequencies, e.g., at 0 Hz (to cancel the Earth's magnetic field (which is largely constant in time)), and at 60 Hz harmonics (e.g., 60 Hz, 120 Hz, 180 Hz, 240 Hz, etc.) to cancel peaks at these harmonics caused by electrical power in the United States, or at 50 Hz harmonics (e.g., 50 Hz, 100 Hz, 150 Hz, 200 Hz, etc.) to cancel peaks at these harmonics caused by electrical power in the Europe. Further details discussing canceling the outside magnetic field $B_{OUT}$ at distinct frequencies are set forth in disclosed in U.S. Provisional Application Ser. No. 62/975,693, entitled "Nested and Parallel Feedback Control Loops For Ultra-Fine Measurements of Magnetic Fields From the Brain Using a Wearable MEG System".

In the illustrated embodiment, the signal acquisition unit 18 takes advantage of the high dynamic range of the coarse magnetometers 26a to compensate for the relatively low dynamic range of the fine magnetometers 26b to cancel the large outside magnetic field $B_{OUT}$, while also taking advantage of high sensitivity of the fine magnetometers 26b to compensate for the low sensitivity of the coarse magnetometers 26a to measure the MEG signal $S_{MEG}$.

In particular, the optimal linear feedback control loop 50 includes a coarse feedback control loop 50a and a fine feedback control loop 50b. The signal acquisition unit 18 initially employs the coarse feedback control loop 50a having a relatively low sensitivity, but relatively high dynamic range, for coarsely cancelling the outside magnetic field $B_{OUT}$ (e.g., low-frequency cancellation of the outside magnetic field $B_{OUT}$ contributed by the Earth's magnetic field (e.g., any of the techniques described in U.S. patent application Ser. No. 16/752,393, entitled "Neural Feedback Loop Filters for Enhanced Dynamic Range Magnetoencephalography (MEG) Systems and Methods," which is expressly incorporated herein by reference, a broadband cancellation technique, and/or the harmonic frequency band cancellation techniques described below), such that the spatial components of the total residual magnetic field measurement $B^F_{TOT}$ at the fine magnetometers 26b drop to a baseline level within the operating range of the fine magnetometers 26b.

The signal acquisition unit 18 subsequently employs the fine feedback control loop 50b, which has a relatively high sensitivity, but a low dynamic range that encompasses this baseline level for finely cancelling the outside magnetic field $B_{OUT}$ (e.g., low-frequency cancellation of the outside magnetic field $B_{OUT}$ contributed by the Earth's magnetic field, broadband cancellation, and/or the harmonic frequency band cancellation techniques described below), such that the spatial components of the total residual magnetic field $B^F_{TOT}$ at the fine magnetometers 26b further drop from the baseline level to an even lower level, which can make operation of the magnetometers 26 more reliable.

In particular, the coarse feedback control loop 50a and fine feedback control loop 50b are implemented by the processor 30, with the coarse feedback control loop 50a coarsely controlling the set of magnetic field actuators 28 via the noisy actuation control signals C' in response to input from the coarse magnetometers 26a in the form of noisy total residual magnetic field measurements $B'^C_{TOT-MEAS}$ and the fine feedback control loop 50b finely controlling the set of magnetic field actuators 28 via the noisy actuation control signals C' in response to input from the fine magnetometers 26b in the form of noisy total residual magnetic field measurements $B'^F_{TOT-MEAS}$.

Initially, due to the relatively low dynamic range of the fine magnetometers 26b, the magnitude of the total residual magnetic field measurement $B^F_{TOT}$ at the fine magnetometers 26b is too great for the fine magnetometers 26b to measure the total residual magnetic field $B^F_{TOT}$, and thus, will output total residual magnetic field measurements $B^F_{TOT-MEAS}$ that are out-of-range. However, due to the relatively high dynamic range of the coarse magnetometers 26a, the spatial components of the total residual magnetic field measurement $B^C_{TOT}$ can be respectively measured by the coarse magnetometers 26a, which outputs total residual magnetic field measurements $B^C_{TOT-MEAS}$ that are in-range.

When the magnitude of the total residual magnetic field measurement $B^F_{TOT}$ is above the dynamic range of the fine magnetometers 26b, the processor 30 acquires the noisy total residual magnetic field measurements $B'^C_{TOT-MEAS}$ from the coarse magnetometers 26a, computes the characteristics (namely, the amplitude and phase) of the noisy actuated magnetic field $B'_{ACT}$ estimated to minimize the noisy total residual magnetic field measurements $B'^C_{TOT-MEAS}$, and generates the actuation control signals C for output to the magnetic field actuators 28 for at least partially cancelling the outside magnetic field $B_{OUT}$ at the fine magnetometers 26b, and ultimately suppressing the total residual magnetic field measurement $B^F_{TOT}$ at the fine magnetometers 26b.

Notably, in the embodiment illustrated in FIG. 3, the set of magnetic field actuators 28 are spatially much closer to the fine magnetometers 26b (and, in fact, may be integrated with the fine magnetometers 26b as a single unit) than the coarse magnetometers 26a. Despite the fact that the coarse magnetometers 26a and fine magnetometers 26b may essentially experience the same outside magnetic field $B_{OUT}$, due to the spatial differences between coarse magnetometers 26a and fine magnetometers 26b relative to the proximate magnetic field actuators 28, the coarse magnetometers 26a will be affected by the noisy actuated magnetic field $B'_{ACT}$ generated by the magnetic field actuators 28 much less than the fine magnetometers 26b will be affected by the same noisy actuated magnetic field $B'_{ACT}$ (e.g., 20%).

Hence, in this example, ignoring the minute contribution of the MEG magnetic field $B_{MEG}$ for purposes of simplicity, the coarse magnetometers 26a and fine magnetometers 26b will measure a different total residual magnetic field $B_{TOT}=B_{OUT}+B'_{ACT}$, because even though the outside magnetic field $B_{OUT}$ may be the same at both coarse magnetometers 26a and fine magnetometers 26b, the noisy actuated magnetic field $B'_{ACT}$ will differ between the coarse magnetometers 26a and fine magnetometers 26b based on their different proximities to the magnetic field actuators 28. Thus, absent estimation of the spatial components of the total residual magnetic field measurements $B^F_{TOT}$ respectively at each fine magnetometer 26b, cancellation of the outside magnetic field $B_{OUT}$, and the resulting suppression of the total residual magnetic field measurements $B^F_{TOT}$ at the fine magnetometers 26b based directly (i.e., without correction) on the noisy total residual magnetic field measurements $B'^C_{TOT-MEAS}$ from the coarse magnetometers 26a may be insufficient.

Thus, in the illustrated embodiment, when only the coarse feedback control loop 50a is active, the magnetic field estimator 56 may initially estimate the spatial components of the total residual magnetic field $B^F_{TOT}$ respectively at each fine magnetometer 26b based on the noisy total residual magnetic field measurements $B'^C_{TOT-MEAS}$ from the coarse magnetometers 26a, as well as based on the actuation control signals C output by the processor 30, and outputting total residual magnetic field estimates $B^F_{TOT-EST}$ of the spatial components of the total residual magnetic field $B^F_{TOT}$ at the fine magnetometers 26b.

The plurality of optimal linear controllers 56 may then generate the actuation control signals C in response to the estimated total residual magnetic field measurements $B^F_{TOT-EST}$ at the fine magnetometers 26b. In accordance with the actuation control signals C respectively output by the optimal linear controllers 56, the magnetic field actuators 28 generate the noisy actuated magnetic field $B'_{ACT}$, which combines with the outside magnetic field $B_{OUT}$ (along with weak MEG magnetic field $B_{MEG}$ from the brain 14), yielding a total residual magnetic field $B^F_{TOT}$ at the fine magnetometers 26b having spatial components that are at a baseline level within the operating range of the fine magnetometers 26b.

Once the spatial components of the total residual magnetic field $B^F{}_{TOT}$ at the fine magnetometers 26b are at the baseline level, the noisy total residual magnetic field $B'^F{}_{TOT}$ can be respectively measured by the fine magnetometers 26b, which output the total residual magnetic field measurements $B^F{}_{TOT\text{-}MEAS}$ that combine with the post-magnetometer noise $N_B$ to create the noisy total residual magnetic field measurements $B'^F{}_{TOT\text{-}MEAS}$. The optimal linear controllers 56 may then generate the actuation control signals C in response to the noisy fine total residual magnetic field measurements $B'^F{}_{TOT\text{-}MEAS}$ of the fine magnetometers 26b.

In one embodiment, even when the spatial components of the total residual magnetic field measurements $B^F{}_{TOT}$ at the fine magnetometers 26b are at the baseline level, such that all of the fine total residual magnetic field measurements $B^F{}_{TOT\text{-}MEAS}$ of the fine magnetometers 26b are in-range, the processor 30 may be further configured for correcting or refining the total residual magnetic field measurements $B^F{}_{TOT\text{-}MEAS}$ from the fine magnetometers 26b using the estimation techniques described in U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", and/or U.S. Provisional Application Ser. No. 62/975,723, entitled "Algorithms that Exploit Maxwell's Equations and Geometry to Reduce Noise for Ultra-Fine Measurements of Magnetic Fields from the Brain Using a Wearable MEG System", which are expressly incorporated herein by reference.

Thus, when the coarse feedback control loop 50a is active and the fine feedback control loop 50b is at least partially active, the magnetic field estimator 56 may estimate the spatial components of the total residual magnetic field measurement $B^F{}_{TOT}$ respectively at each fine magnetometer 26b based on the noisy total residual magnetic field measurements $B'^C{}_{TOT\text{-}MEAS}$ from the coarse magnetometers 26a and the noisy total residual magnetic field measurements $B'^F{}_{TOT\text{-}MEAS}$ from the fine magnetometers 26b that are in-range, as well as based on the actuation control signals C output by the processor 30, and outputting the total residual magnetic field estimates $B^F{}_{TOT\text{-}EST}$ of the spatial components of the total residual magnetic field $B^F{}_{TOT}$ at the fine magnetometers 26b.

The plurality of optimal linear controllers 56 may then again generate the actuation control signals C in response to the estimated total residual magnetic field measurements $B^F{}_{TOT\text{-}EST}$ at the fine magnetometers 26b, and in accordance with the actuation control signals C respectively output by the optimal linear controllers 56, the magnetic field actuators 28 may again generate the noisy actuated magnetic field $B'_{ACT}$, which combines with the outside magnetic field $B_{OUT}$ (along with weak MEG magnetic field $B_{MEG}$ from the brain 14), yielding a total residual magnetic field $B^F{}_{TOT}$ at the fine magnetometers 26b having spatial components that are at a lower level, increasing the measurement accuracy of the fine magnetometers 26b. At this point, the noisy total residual magnetic field measurements $B'^F{}_{TOT\text{-}MEAS}$ from the fine magnetometers 26b can serve to collect MEG signals $S_{MEG}$ representative of the spatial components of the MEG magnetic field $B_{MEG}$ for further processing by the signal processing unit 20 to identify and localize neural activity in the brain 14 of the user 12.

In an alternative embodiment, the signal acquisition unit 18 (shown in FIG. 4) only employs the coarse feedback control loop 50a for at least partially cancelling the outside magnetic field $B_{OUT}$, such that the spatial components of the total residual magnetic field $B^F{}_{TOT}$ at the fine magnetometers 26b drop to a baseline level within the operating range of the fine magnetometers 26b. In this case, the signal acquisition unit 18 does not have a fine feedback control loop 50b, and the processor 30 only uses the noisy total residual magnetic field measurements $B'^C{}_{TOT\text{-}MEAS}$ from the coarse magnetometers 26a to compute the characteristics of the noisy actuated magnetic field $B'_{ACT}$ estimated to suppress the total residual magnetic field measurement $B^F{}_{TOT}$ at the fine magnetometers 26b to near-zero, even after the spatial components of the total residual magnetic field $B^F{}_{TOT}$ at the fine magnetometers 26b are already at the baseline level, such that the fine magnetometers 26b remain in an operating range.

Whether the signal acquisition unit 18 employs both the coarse feedback control loop 50a and the fine feedback control loop 50b to cancel the outside magnetic field $B_{OUT}$, or employs only the coarse feedback control loop 50a to cancel the outside magnetic field $B_{OUT}$, it can be appreciated that the signal acquisition unit 18 is capable of coarsely canceling a large portion of the outside magnetic field $B_{OUT}$, while still collecting signals from the fine magnetometers 26b sensitive enough to measure the weaker MEG magnetic field $B_{MEG}$ generated by the neural activity in the brain 14 of the user 12.

Further details discussing the employment of a coarse feedback control loop and a fine feedback control loop to coarsely and finely cancel an outside magnetic field $B_{OUT}$ are disclosed in U.S. Provisional Application Ser. No. 62/975,693, entitled "Nested and Parallel Feedback Control Loops For Ultra-Fine Measurements of Magnetic Fields From the Brain Using a Wearable MEG System".

The processor 30 is configured for managing the coarse feedback control loop 50a and fine feedback control loop 50b by employing a management control loop 52, which manages the coarse feedback control loop 50a and fine feedback control loop 50b (e.g., how the noisy total residual magnetic field measurements $B'^C{}_{TOT\text{-}MEAS}$ from the coarse magnetometers 26a and the noisy total residual magnetic field measurements $B'^F{}_{TOT\text{-}MEAS}$ from the fine magnetometers 26b are to be used) for optimal cancellation of the outside magnetic field $B_{OUT}$, and thus optimal suppression of the total residual magnetic field $B^F{}_{TOT}$ at the fine magnetometers 26b, and corrects additional factors that can change more slowly over time, such as, e.g., calibrating the magnetometers 26 (e.g., using calibration techniques described in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", which is expressly incorporated herein by reference), and optimizing performance metrics in the signal acquisition unit 18, as will be described in further detail below.

The management control loop 52 manages the coarse feedback control loop 50a and fine feedback control loop 50b based on whether the fine magnetometers 26b are in-range or out-of-range, e.g., by considering noisy total residual magnetic field measurements $B'^C{}_{TOT\text{-}MEAS}$ from the coarse magnetometers 26a and ignoring noisy total residual magnetic field measurements $B'^F{}_{TOT\text{-}MEAS}$ from fine magnetometers 26b that are out-of-range, and in the case where estimation of the total residual magnetic field $B^F{}_{TOT}$ at the fine magnetometers 26b after the fine magnetometers 26b re in-range, ignoring noisy total residual magnetic field measurements $B'^C{}_{TOT\text{-}MEAS}$ from the coarse magnetometers 26a, and considering only the noisy total residual magnetic field measurements $B'^F{}_{TOT\text{-}MEAS}$ from fine magnetometers 26b. The management control loop 52 may monitor the overall behavior and history of the spatial components of the total residual magnetic field $B^F_{TOT}$ at the fine magnetometers 26b to determine whether or not a fine magnetometer 26b is in-range or out-of-range. It is noted that the spatial components of the total residual magnetic field $B^F_{TOT}$ at the fine magnetometers 26b may be substantially different from each other, and thus, some of the fine magnetometers 26b may be in-range, while other fine magnetometers 26b may be out-of-range.

With knowledge of whether each of the fine magnetometers 26b are in-range or out-of-range, the management control loop 52 may generally activate the fine feedback control loop 50b after initiating activation of the coarse feedback control loop 50a. In this manner, as discussed above, the coarse feedback control loop 50a may coarsely control the noisy actuated magnetic field $B'_{ACT}$ in a manner that at least partially cancels the outside magnetic field $B_{OUT}$, and thus suppresses the total residual magnetic field $B^F_{TOT}$ at the fine magnetometers 26b to a baseline level, such that the at least one of magnetometers 26b comes in-range. The management control loop 52 may then activate the fine feedback control loop 50b to finely control the noisy actuated magnetic field $B'_{ACT}$ in a manner that further suppresses the total residual magnetic field $B^F_{TOT}$ at the fine magnetometer(s) 26b that just came in-range to a lower level.

In one embodiment, the management control loop 52 strictly activates only the coarse feedback control loop 50a (e.g., if one of the fine magnetometers 26b is out-of-range) or only the fine feedback control loop (e.g., if all of the fine magnetometers 26 are in-range), but not both the coarse feedback control loop 50a and the fine feedback control loop 50b at the same time. In this case, the management control loop 52 will only consider noisy total residual magnetic field measurements $B'^F_{TOT-MEAS}$ from fine magnetometers 26b when the coarse feedback control loop 50a is active, and will only consider noisy total residual magnetic field measurements $B'^F_{TOT-MEAS}$ when the fine feedback control loop 50b is active.

In another particularly preferred embodiment, however, the management control loop 52, at any given time, may not strictly activate only the coarse feedback control loop 50a or strictly activate only the fine feedback control loop 50b, and thus, both of the coarse feedback control loop 50a and fine feedback control loop 50b may be at least partially activated. The management control loop 52 may choose to consider only the noisy total residual magnetic field measurements $B'^F_{TOT-MEAS}$ that are in-range. In this case, the management control loop 52 may determine whether or not the fine magnetometer 26b is in-range, and performs a "sensor hand-off" procedure, and in particular, switches back and forth between consideration of a noisy total residual magnetic field measurement $B'^C_{TOT-MEAS}$ from any given coarse magnetometer 26a and consideration of a noisy total residual magnetic field measurement $B'^F_{TOT-MEAS}$ from any given fine magnetometer 26b. It is understood that only some of the fine magnetometers 26b may be out-of-range at any given moment, so the sensor hand-off procedure can be from one, some, or all coarse magnetometers 26a to one, some, or all of the fine magnetometers 26b.

For example, if the management control loop 52 is currently considering a noisy total residual magnetic field measurement $B'^C_{TOT-MEAS}$ from a coarse magnetometer 26, and a previously unavailable fine magnetometer 26b is deemed to be in-range, the processor 30 may then ignore a noisy total residual magnetic field measurement $B'^C_{TOT-MEAS}$ from at least one coarse magnetometer 26a that is in proximity to the previously unavailable fine magnetometer 26b, and instead consider the more accurate total residual magnetic field measurement $B'^F_{TOT-MEAS}$ from this previously unavailable fine magnetometer 26b (in essence, passing or handing off measurement of the total residual magnetic field $B_{TOT}$ from the coarse magnetometer(s) 26b to the fine magnetometer 26b).

On the contrary, if the management control loop 52 is currently considering a total residual magnetic field measurement $B'^F_{TOT-MEAS}$ from a fine magnetometer 26b, and the fine magnetometer 26b is subsequently deemed to fall out-of-range for any one of a variety of reasons (e.g., if the user 12, and thus the fine magnetometer 26b, gets too close to a power outlet, a fridge magnet, a cell phone, or perhaps if the user 12 turns their head so suddenly that the total residual magnetic field $B^F_{TOT}$ at the fine magnetometer 26b varies too quickly), the management control loop 52 may then ignore the total residual magnetic field measurement $B'^F_{TOT-MEAS}$ from that fine magnetometer 26b, and instead consider the noisy total residual magnetic field measurement $B'^C_{TOT-MEAS}$ from at least one coarse magnetometer 26a in proximity to the now unavailable fine magnetometer 26b (in essence, passing or handing off detection of the total residual magnetic field $B_{TOT}$ from the fine magnetometer 26b to the coarse magnetometer 26a).

Thus, in this manner, the management control loop 52 may operate the fine feedback control loop 50b to control the noisy actuated magnetic field $B'_{ACT}$ based on the total residual magnetic field measurement $B'^F_{TOT-MEAS}$ from the fine magnetometers 26b as they come in-range. The management control loop 52 may operate the fine feedback control loop 50b to prevent control of the noisy actuated magnetic field $B'_{ACT}$ based on the total residual magnetic field measurement $B'^F_{TOT-MEAS}$ from the fine magnetometers 26b as they go out-of-range.

In an optional embodiment, the management control loop 52 may weight the fine magnetometers 26b, in which case, the management control loop 52 may not perform a "sensor hand-off" procedure, per se, but may assign a weight a to any given fine magnetometer 26b between a value 0 (no weight) and 1 (full weight). For example, the management control loop 52 may monitor different operating parameters of a fine magnetometer 26b to determine whether the fine magnetometer 26b is in a linear operating range, or outside of the linear operating range, but not saturated (non-linear operating range), or is saturated. If the fine magnetometer 26b is found to be in the linear operating range, the weighting a assigned to the fine magnetometer 26b can be 1 (i.e., full weight); if the fine magnetometer 26b is found to be saturated, the weighting a assigned to the fine magnetometer 26b can be 0 (i.e., no weight); and if the fine magnetometer 26b is found to be in the non-linear operating range, the weighting a assigned to the fine magnetometer 26b can be between 0 and 1 (i.e., partial weight), depending on how close the fine magnetometer 26b is to saturation.

As discussed above, the management control loop 52 is configured for correcting factors that can change more slowly over time to optimize the cancellation of the outside magnetic field $B_{OUT}$. For example, the management control loop 52 may be configured for implementing adaptions to slow changes of the coarse feedback control loop 50a and fine feedback control loop 50b over time. The management control loop 52 is configured for identifying and determining parameters and coefficients of the signal acquisition unit 18 and the outside magnetic field $B_{OUT}$. The management control loop 52 is configured for employing computational algorithms to determine unknown parameters from the noisy total residual magnetic field measurements $B'^C_{TOT-MEAS}$ and the noisy total residual magnetic field measurements $B'^F_{TOT-MEAS}$ from the coarse magnetometers 26a and fine magnetometers 26b, such as fitting of physical and calibrated mathematical and numerical models to the total residual magnetic field measurements $B'^C_{TOT-MEAS}$ and the total residual magnetic field measurements $B'^F_{TOT-MEAS}$ to identify missing or insufficiently known coefficients and parameters. Such parameters and coefficients can include offset and gain coefficients for the coarse magnetometers 26a, gain constants for the fine magnetometers 26b, actuator gains and offsets for the set of magnetic field actuators 28, electronics time delay latency coefficients in the coarse feedback control loop 50a and fine feedback control loop 50b (i.e., the amount of time between generating the total residual magnetic field measurements $B'^C_{TOT-MEAS}$ or the total residual magnetic field measurements $B'^F_{TOT-MEAS}$ and activating the set of magnetic field actuators 28), and other parameters of the signal acquisition unit 18. The management control loop 52 may determine coefficients and parameters for different temporal and spatial ranges. Likewise, the gain that the set of magnetic field actuators 28 may have on the coarse magnetometers 26a and fine magnetometers 26b may differ with the placement and location offset of magnetic field actuators 28 (e.g., as the head of the user 12 moves or the support structure 24 deforms). The management control loop 52 may identify at least one, some, or all of the coefficients or parameters over these changing conditions.

In one exemplary instance, a mathematical and numerical model of the signal acquisition unit 18, or a portion thereof, has some coefficients or parameters that are considered poorly or insufficiently known. In another exemplary instance, a mathematical and numerical model of the signal acquisition unit 18 does not have a predetermined structure, and the coefficients or parameters consist of transfer functions or linear mappings from one set of signals to another. The management control loop 52 may compare the response of a structured or unstructured model of the signal acquisition unit 18 to the measurements from the coarse magnetometers 26a and fine magnetometers 26b, and the coefficients or parameters may be varied until any disagreement between the mathematical model of the signal acquisition unit 18 and the actual measured signals is decreased. The coefficients or parameters of the mathematical model that achieve such a decrease in disagreement are the estimated parameters of the signal acquisition unit 18 (meaning, if the mathematical model with selected parameter values x, y, and z best matches the actual measured behavior of the system, then the values x, y, and z are a system identification estimate of the poorly or insufficiently known coefficients or parameters of the system). In determining the coefficients or parameters of the signal acquisition unit 18, the management control loop 52 may employ weighted least squares, observer filters, Kalman filters, Wiener filters, or other filters. The management control loop 52 may employ time domain, frequency domain, recursive techniques, parametric and non-parametric methods, linear and nonlinear optimization techniques including gradient descent, matrix methods, convex methods, non-convex methods, neural networks, genetic algorithms, fuzzy logic, and machine learning methods.

The management control loop 52 may perform calibration techniques prior to operating the neural activity measurement system 10, or calibration techniques may be performed in real-time as the neural activity measurement system 10 operates. For example, prior to usage, the signal acquisition unit 18 may be calibrated by applying a known magnetic field in a controlled shielded setting (e.g., to characterize the coarse magnetometers 26a for their offsets and gain measurements). However, the properties of coarse magnetometers 26a, fine magnetometers 26b, or set of magnetic field actuators 28 may vary due to environmental variations, such as, e.g., variations in temperature, laser power (for magnetometers that utilize lasers), motion or deformation of the support structure 24, or other deformations, such as bending of the coarse magnetometers 26a, fine magnetometers 26b, or offset of magnetic field actuators 28 due to temperature or mechanical stresses. Thus, in addition to performing calibrations ahead of time, the management control loop 52 may perform calibrations techniques during system operation. For example, if the offsets and gains of the coarse magnetometers 26a change during usage of the neural activity measurement system 10, the management control loop 52 may estimate the offsets and gains of the coarse magnetometers 26a in real time (i.e., as the neural activity measurement system 10 is running), e.g., by estimating and comparing the offset of one coarse magnetometer against the measurements of other coarse or fine magnetometers. Further details discussing the calibration of coarse magnetometers are disclosed in U.S. Provisional Application Ser. No. 62/975,709, entitled "Self-Calibration of Flux Gate Offset and Gain Drift To Improve Measurement Accuracy Of Magnetic Fields From the Brain Using a Wearable MEG System", which is expressly incorporated herein by reference.

It should be appreciated that, in the case where the signal acquisition unit 18 comprises multiple sets of magnetic field actuators 28 and processors 30, the components, along with the coarse feedback control loop 50a, fine feedback control loop 50b, and management control loop 52, illustrated in FIG. 4 may be duplicated. In this case, a subset of the coarse magnetometers 26a will be associated with each coarse feedback control loop 50a, and a subset of the fine magnetometers 26b will be associated with each fine feedback control loop 50b. Because the noisy actuated magnetic field $B'_{ACT}$ generated by each set of the magnetic field actuators 28 will affect all of the coarse magnetometers 26a and all of the fine magnetometers 26b, the processors 30 may communicate with each other to generate the proper actuation control signals C that will result in a composite cancelling magnetic field $B_{ACT}$ to be generated by the combination of sets of magnetic field actuators 28 to cancel the outside magnetic field $B_{OUT}$. Alternatively, a single processor 30 may be used to control all sets of the magnetic field actuators 26.

Further details discussing the functioning of the management control loop 52 are disclosed in U.S. Provisional Application Ser. No. 62/975,693, entitled "Nested and Parallel Feedback Control Loops For Ultra-Fine Measurements of Magnetic Fields From the Brain Using a Wearable MEG System".

Figure 5:
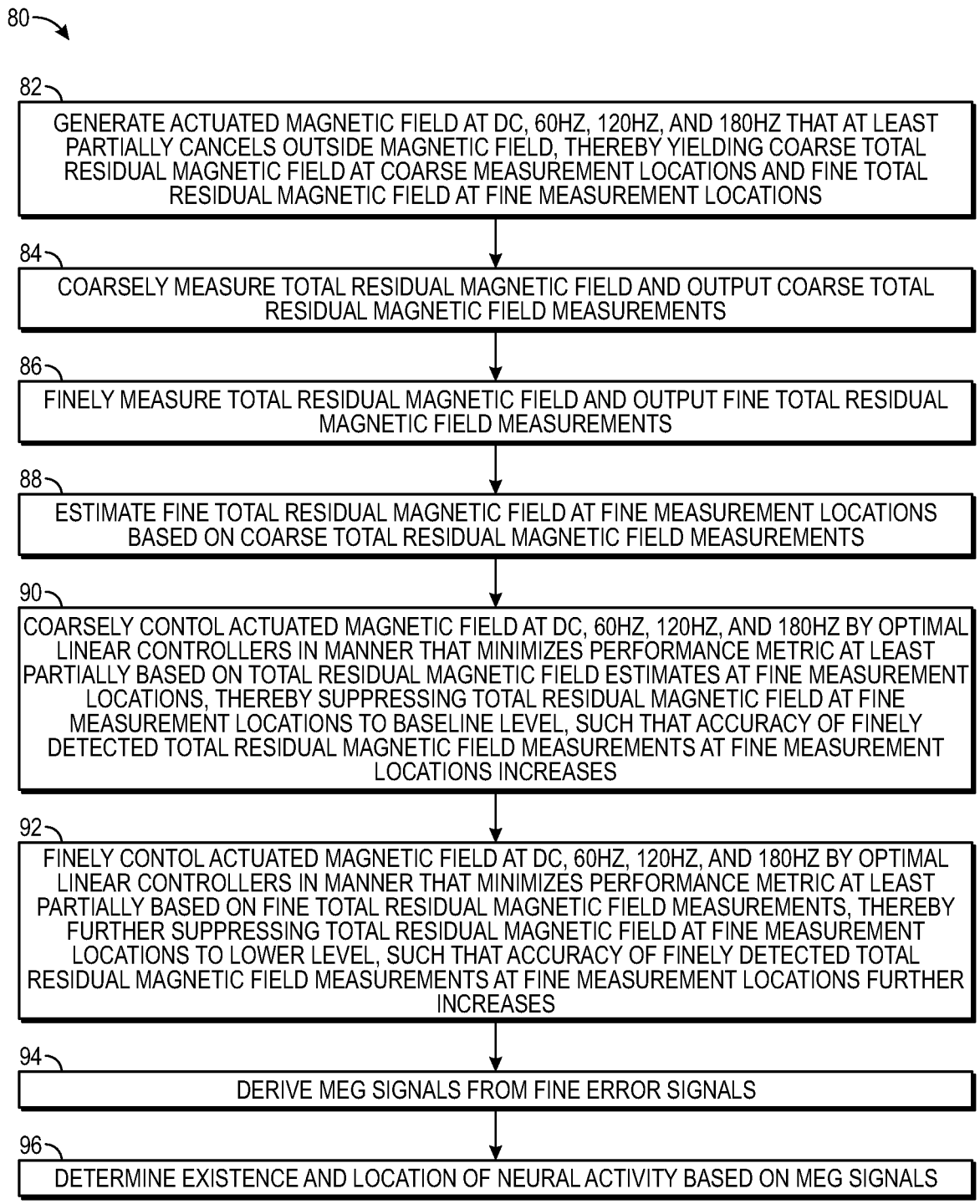
FIG. 5 is a flow diagram of one exemplary method of identifying and localizing neural activity in the brain of a user.

Referring now to FIG. 5, one exemplary method 80 of identifying and localizing neural activity in the brain 14 of a user 12 will be described.

The method 80 comprises generating the actuated magnetic field $B_{ACT}$ at a plurality of distinct frequencies (e.g., DC, 60 Hz, 120 Hz, and 180 Hz) that at least partially cancels an outside magnetic field $B_{OUT}$ at the distinct frequencies (e.g., via the set of magnetic field actuators 28 of the signal acquisition unit 18), thereby yielding a total residual magnetic field $B_{TOT}$ at a plurality of measurement locations (e.g., at the magnetometers 26 of the signal acquisition unit 18), and in particular, a coarse total residual magnetic field $B^C_{TOT}$ at a plurality of coarse measurement locations (e.g., at the coarse magnetometers 26a of the signal acquisition unit 18) and a fine total residual magnetic field $B^F_{TOT}$ at a plurality of fine measurement locations (e.g., at the fine magnetometers 26b of the signal acquisition unit 18) (step 82).

Due to pre-magnetometer noise $N_A$ at the magnetometers 26, a noisy coarse total residual magnetic field $B'_{TOT}$ may be yielded at the measurement locations, and in particular, a noisy coarse total residual magnetic field $B'^C_{TOT}$ at the coarse measurement locations and a noisy fine total residual magnetic field $B'^F_{TOT}$ at the fine measurement locations. In the preferred embodiment, the actuated magnetic field $B_{ACT}$ is generated in all three dimensions and is uniform, although in alternative embodiments, the actuated magnetic field $B_{ACT}$ may be generated in less three dimensions and may be non-uniform (e.g., a gradient).

The method 80 further comprises measuring the total residual magnetic field $B_{TOT}$ at the measurement locations and outputting total residual magnetic field measurements $B_{TOT-MEAS}$ (e.g., via the magnetometers 26 of the signal acquisition unit 18), and in particular, coarsely measuring the total residual magnetic field $B^C_{TOT}$ at coarse measurement location and outputting coarse total residual magnetic field measurements $B^C_{TOT-MEAS}$ (e.g., via the coarse magnetometers 26a of the signal acquisition unit 18) (step 84), and finely measuring the total residual magnetic field $B^F_{TOT}$ at fine measurement locations and outputting fine total residual magnetic field measurements $B^F_{TOT-MEAS}$ (e.g. via the fine magnetometers 26b of the signal acquisition unit 18) (step 86). Due to post-magnetometer noise $N_B$ at the magnetometers 26, the coarse total residual magnetic field measurements $B^C_{TOT-MEAS}$ and the fine total residual magnetic field measurements $B^F_{TOT-MEAS}$ may be noisy coarse total residual magnetic field measurements $B'^C_{TOT-MEAS}$ and noisy fine total residual magnetic field measurements $B'^F_{TOT-MEAS}$.

Next, the method 80 comprises controlling the actuated magnetic field $B_{ACT}$ with the optimal linear controllers 56 (e.g., one of a linear quadratic regulator (LQR) controller, an H2 controller, and an Hinfinity controller) at DC, 60 Hz, 120 Hz, and 180 Hz based on the total residual magnetic field measurements $B_{TOT-MEAS}$ in a manner that minimizes a performance metric that includes magnitude of the suppressed fine total residual magnetic field $B^F_{TOT}$ at the fine measurement locations (e.g., at the fine magnetometers 26b of the signal acquisition unit 18), a magnitude of the control effort of the optimal linear controllers 56, and a time-integral of the suppressed fine total residual magnetic field $B^F_{TOT}$ at the fine measurement locations (e.g., at the fine magnetometers 26b of the signal acquisition unit 18).

In one embodiment, because the fine total residual magnetic field measurements $B^F_{TOT-MEAS}$ may be initially inaccurate or even non-existent (e.g., if the fine magnetometers 26b are out-of-range), the method 80 comprises estimating the fine total residual magnetic field $B^F_{TOT}$ (e.g., via the magnetic field estimator 54) at the fine measurement locations (e.g., at the fine magnetometers 26b of the signal acquisition unit 18) based on the coarse total residual magnetic field measurements $B^C_{TOT-MEAS}$ at the coarse measurement locations (e.g. at the coarse magnetometers 26a of the signal acquisition unit 18) (step 88).

The method 80 further comprises coarsely controlling the actuated magnetic field $B_{ACT}$ at DC, 60 Hz, 120 Hz, and 180 Hz by the optimal linear controllers 56 in a manner that minimizes the performance metric (e.g., by sending actuation control signals C to the set of magnetic field actuators 28 of the signal acquisition unit 18) at least partially based on the estimated total residual magnetic field measurements $B^F_{TOT-EST}$ at the fine measurement locations, thereby cancelling the outside magnetic field $B_{OUT}$, such that the fine total residual magnetic field $B^F_{TOT}$ at DC, 60 Hz, 120 Hz, and 180 Hz is suppressed at the fine measurement locations to a baseline level with reasonable control effort (step 90). As a result, the accuracy of the fine total residual magnetic field measurements $B^F_{TOT-MEAS}$ at the fine measurement locations increases (e.g., the fine magnetometers 26b of the signal acquisition unit 18 come in-range).

The method 80 further comprises finely controlling the actuated magnetic field $B_{ACT}$ at DC, 60 Hz, 120 Hz, and 180 Hz by the optimal linear controllers 56 in a manner that minimizes the performance metric (e.g., by sending actuation control signals C to the set of magnetic field actuators 28 of the signal acquisition unit 18) at least partially based on the fine total residual magnetic field measurements $B^F_{TOT-MEAS}$ at the fine measurement locations, thereby cancelling the outside magnetic field $B_{OUT}$, such that the fine total residual magnetic field $B^F_{TOT}$ at DC, 60 Hz, 120 Hz, and 180 Hz is further suppressed at the fine measurement locations to a lower level with reasonable control effort (step 92). As a result, the accuracy of the fine total residual magnetic field measurements $B^F_{TOT-MEAS}$ at the fine measurement locations further increases (e.g., the fine magnetometers 26b of the signal acquisition unit 18 are further in-range).

Due to pre-actuator noise $N_C$ at the magnetic field actuators 28, actuation control signals C at the actuation locations may be noisy actuation control signals C', and due to the post-actuator noise $N_D$ at the magnetic field actuators 28, the actuated magnetic field $B_{ACT}$ may be a noisy actuated magnetic field $B'_{ACT}$.

The method 80 further comprises deriving a plurality MEG signals $S_{MEG}$ from the fine total residual magnetic field measurements $B^F_{TOT-MEAS}$ (e.g., via the signal acquisition unit 18) (step 94). That is, because the fine total residual magnetic field $B^F_{TOT}$ contains the MEG magnetic field $B_{MEG}$ from the brain 14 of the user 12, the fine total residual magnetic field measurements $B^F_{TOT-MEAS}$ will likewise contain the MEG signals $S_{MEG}$, which can be extracted from the fine total residual magnetic field measurements $B^F_{TOT-MEAS}$. The existence and location of neural activity in the brain 14 of the user 12 may then be determined based on the MEG signals $S_{MEG}$ (e.g., via the signal processing unit 20) (step 96).

Figure 6:
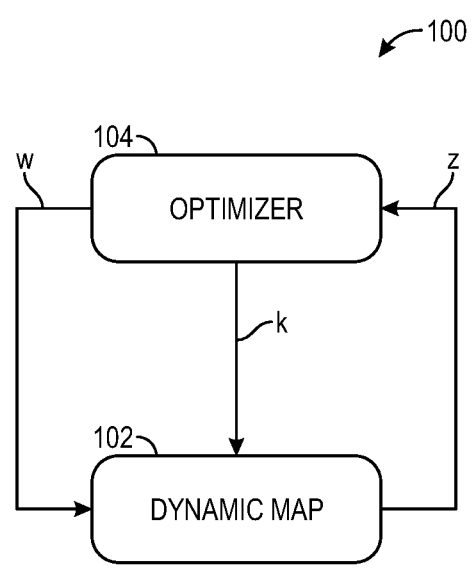
FIG. 6 is a block diagram of an exemplary embodiment of an optimal linear controller design system for optimizing linear optimal controllers used in the signal acquisition unit of FIG. 4.

With reference now to FIG. 6, an optimal linear controller design system 100 constructed in accordance with one embodiment of the present inventions will be described. The optimal linear controller design system 100 is configured for designing one or more optimal linear controllers for use in an optimal linear feedback control loop of an active shield magnetometry system, e.g., the optimal linear controllers 56 in the optimal linear feedback control loop 50 of the signal acquisition unit 18 illustrated in FIG. 4 for cancelling the outside magnetic field $B_{TOT}$ in a manner that suppresses the total residual magnetic field measurement $B^F_{TOT}$ at the fine magnetometers 26b. The optimal linear controller design system 100 designs the optimal linear controllers 56 in a manner that achieves a desired tradeoff between the overall desired performance of the signal acquisition unit 18 in suppressing the total residual magnetic field measurement $B^F_{TOT}$ at the fine magnetometers 26b and the control effort of the signal acquisition unit 18.

As discussed above, the goal of the signal acquisition unit 18 is to detect the small MEG magnetic field $B_{MEG}$ from the brain 14 of the user 12, while rejecting unwanted noise signals, such as the outside magnetic field $B_{OUT}$, as well as rejecting unwanted noise generated by the magnetometers 26 and magnetic field actuators 28. There are limits to how well such unwanted noise can be rejected, and the optimal linear feedback control loop 50 will achieve those limits in order to provide the best possible overall performance of the signal acquisition unit 18.

The optimal linear controller design system 100 generally comprises a dynamic map 102 and an optimizer 104.

The dynamic map 102 represents the relevant complex physics of the optimal linear feedback control loop 50 from the external noise sources W (e.g., the outside magnetic field $B_{OUT}$, pre-magnetometer noise $N_A$, post-magnetometer noise $N_B$, pre-actuator noise $N_C$, and post-actuator noise $N_D$) to a total weighted performance metric z, which indicates how accurately the signal acquisition unit 18 measures the MEG magnetic field $B_{MEG}$ from the brain 14 of the user 12 as compared to the magnitude of external unwanted noise (i.e., the performance of the optimal linear feedback control loop 50 in suppressing the total residual magnetic field measurement $B^F_{TOT}$ at the fine magnetometers 26b), as compared to the amount of energy or power expended by the signal acquisition unit 18 to measure that MEG magnetic field $B_{MEG}$ (i.e., the control effort of the optimal linear feedback control loop 50 in suppressing the total residual magnetic field measurement $B^F_{TOT}$ at the fine magnetometers 26).

It should be appreciated that, although the dynamic map 102 is described herein in relation to a singular optimal linear feedback control loop 50, the coarse feedback control loop 50a and fine feedback control loop 50b are subsumed in the optimal linear feedback control loop 50, as discussed above with respect to FIG. 4. Thus, the dynamic map 50 characterizes the coarse feedback control loop 50a and fine feedback control loop 50b within the optimal linear feedback control loop 50, although alternative embodiments of the dynamic map may characterize optimal linear feedback control loops that include coarse feedback control loops or fine feedback control loops. Furthermore, although the dynamic map 102 is described herein as characterizing an optimal linear feedback control loop 50 for both coarse magnetometers 26a and fine magnetometers 26b, it should be appreciated that the dynamic map 102 may be modified to characterize an optimal linear feedback control loop 50 for only fine magnetometers 26b.

The optimizer 104 comprises a processor on which an optimizer software program (e.g., Simulink® or Control System Toolbox™ from Mathworks®) for inputting noise w representing the external noise sources into the dynamic map 102, receiving the total weighted performance metric z from the dynamic map 102, and modifying optimal linear control gain coefficients k in the dynamic map 102 in a manner that provides the best total weighted performance metric z. In the illustrated embodiment, the total weighted performance metric z is a cost function, and therefore, the optimizer 108 operates to minimize the total weighted performance metric z, such that the error in measuring the MEG magnetic field $B_{MEG}$ (i.e., the total residual magnetic field measurement $B^F_{TOT}$ at the fine magnetometers 26b) is low, even when the unwanted noise from the external noise sources W is high, and with low or acceptable power usage (i.e., the control effort of the optimal linear feedback control loop 50 is reasonable). For the purposes of this specification, the term "optimal" means that the performance of the optimal linear controller 56 is maximized as measured by a well-defined quantitative performance metric, and in this case, the total weighted performance metric z.

Figure 7:
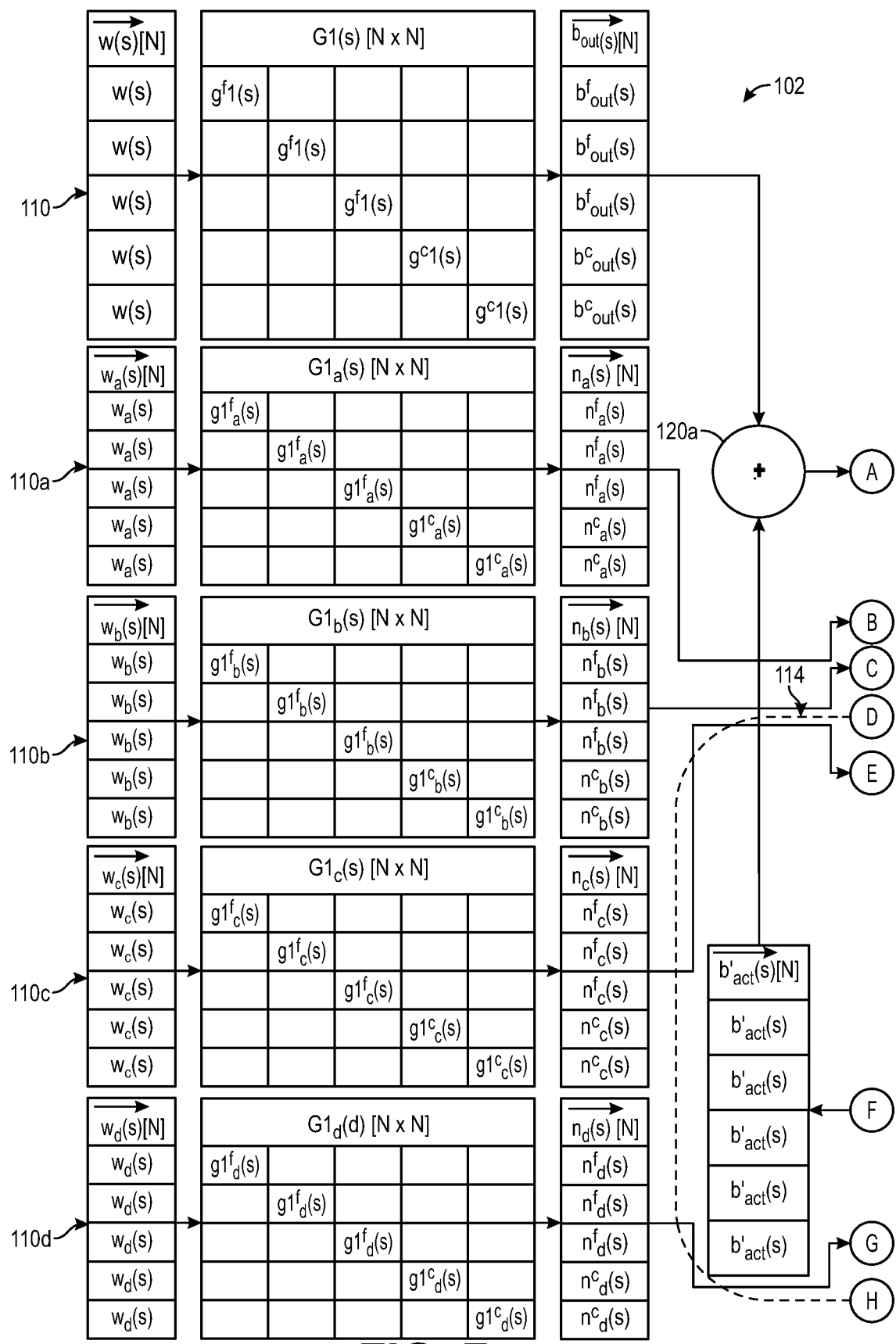
FIG. 7 is a block diagram of a dynamic map of the optimal linear controller design system of FIG. 6.
Figure 7:
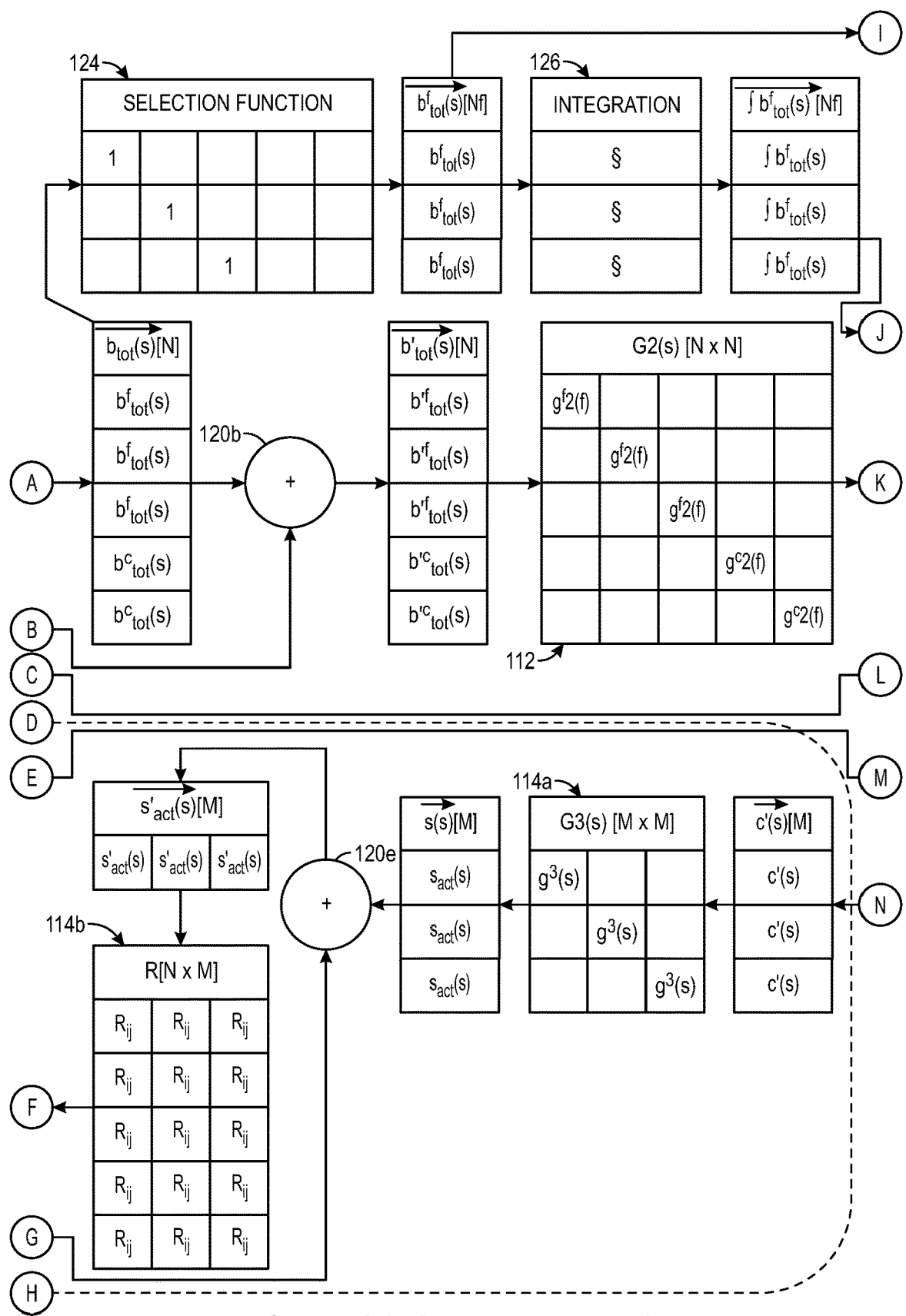
Figure 7:
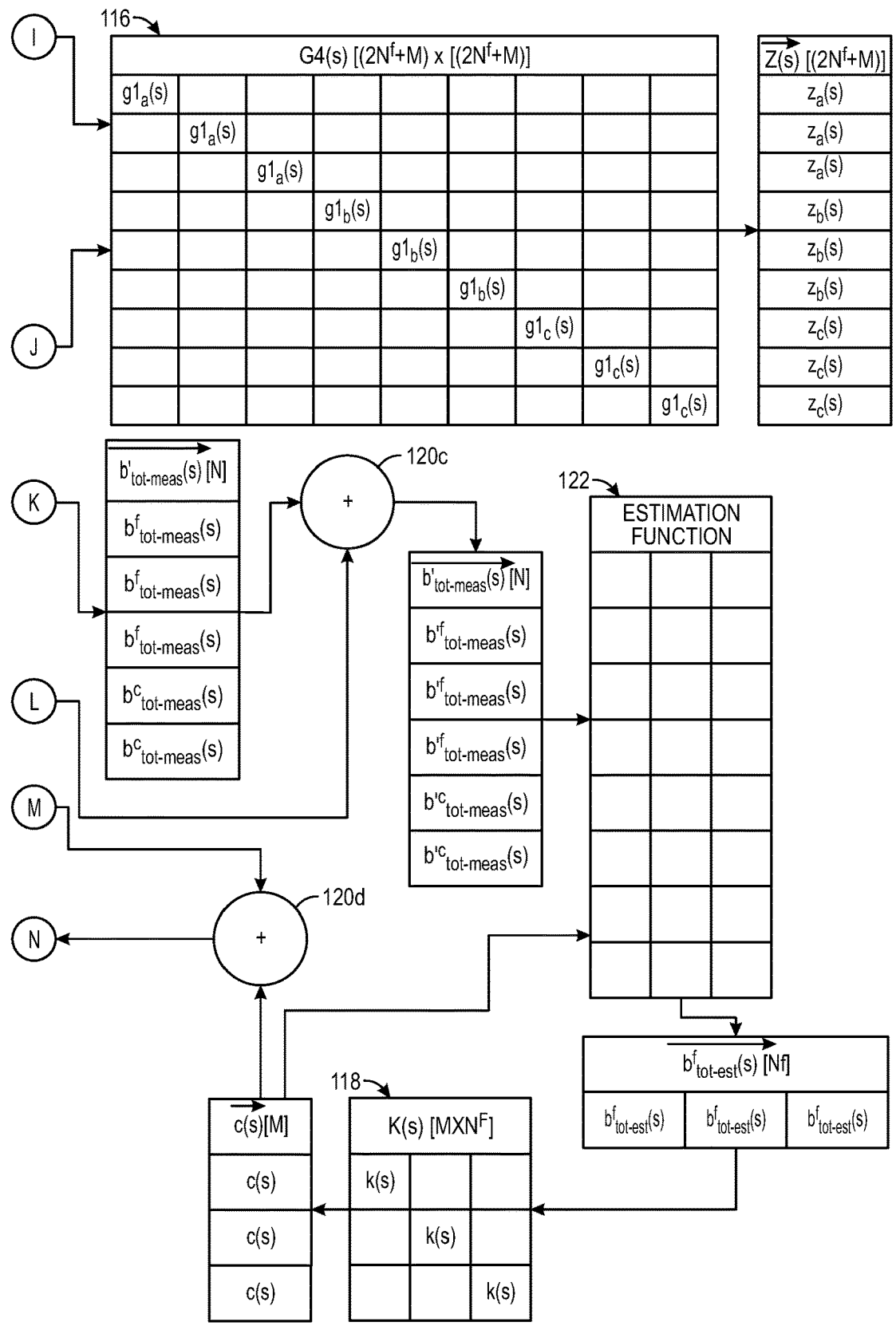

Referring now to FIG. 7, the dynamic map 102 generally comprises a variety of different real-world noise models 110, a magnetometer model 112, an actuated magnetic field model 114, a weighted metric model 116, an optimal linear control model 118, a plurality of magnetic field summation functions 120a-120e, a magnetic field estimation function 122, a magnetic field selection function 124, and a magnetic field integration function 126. Each of the models 110-118 may comprise a matrix of functions that are configured for, in response to an input vector, generating an output vector.

Because physical laws are most often described in terms of differential equations, the matrix functions of each of the models 110-118 may take a state-space form as a matrix of first-order differential or difference equations with no nth-order differential or difference equations. The state variables of the models 110-118 can be reconstructed from measured data, but not themselves measured during operation of the optimal linear feedback control loop 100.

In particular, each entry in the state-space matrix function can comprise a set of continuous time linear equations with a p number of inputs, a q number of outputs, and an n number of state variables, and in the illustrated embodiment, as the following linear equations:

$$\dot{x}(t)=A\cdot x(t)+B\cdot u(t); \text{ and} \quad [1a]$$

$$y(t)=C\cdot x(t)+D\cdot u(t), \quad [1b]$$

where x(t) is a time-varying state vector; y(t) is a time-varying output vector; u(t) is a time-varying input (or control); A is a constant state matrix having a dimension n×n; B is a constant input matrix having a dimension n×p; C is a constant output matrix having a dimension q×n; D is a constant feedthrough (or feedforward) matrix having a dimension q×p; and $\dot{x}(t)$ is a time-varying derivative of the state vector x(t).

Due to the simplicity of matrix transfer function notation, the models 110-118 are illustrated in FIG. 7 as matrix transfer functions (or filter functions). Equations [1a]-[1b] can be equivalently written in frequency-form using the following Laplace domain equations:

$$s\cdot x(s)-x(0)=A\cdot x(s)+B\cdot u(s); \text{ and} \quad [2a]$$

$$y(s)-y(0)=C\cdot x(s)+D\cdot u(s), \quad [2b]$$

where s is the Laplace frequency domain variable, x(s) is the Laplace transform of the time-varying state vector x(t); u(s) is the Laplace transform of the time-varying input vector; y(s) is the Laplace transform of the time-varying output vector; and A, B, C, and D are defined above. A transfer matrix function g(s) can be derived from:

$$y(s)=g(s)\cdot u(s). \quad [3]$$

Equating coefficients from equations [2a]-[2b] yields:

$$g(s)=C(sI-A)^{-1}B+D, \quad [4]$$

where g(s) is the transfer matrix with dimension q×p, and I is the identify matrix. Substituting equation [4] into equation [3] yields:

$$y(s)=g(s)\cdot u(s)=(C(sI-A)^{-1}B+D)\cdot u(s). \quad [5]$$

To enable optimal noise rejections, the noise models 110 are configured for quantifying the physical properties of the noise in the optimal linear feedback control loop 100 using noise transfer functions. In the exemplary embodiment, the input to the noise models 110 is physical white noise (noise that has equal power across all frequencies), and the output from the noise models 110 mimics real-world colored noise (noise that has variable power across frequencies, and that reflects the spectra of noise in the physical world for magnetic, electric, thermal and other relevant physical effects) in time and space, and thus, has spatial and temporal statistics that are an accurate representation of noise. In the exemplary embodiment, the white noise may be generated by a magnetic noise generator (which may be contained in the optimizer 108), and the outputs from one or more of the noise models 110 are vectors, each of which contains elements respectively representing spatial variations of the physical noise assigned to different locations of the magnetometers 26 and magnetic field actuators 28.

In the illustrated embodiment, the noise models 110 comprise an outside magnetic field model 110, a pre-magnetometer noise model 110a, a post-magnetometer noise model 110b, a pre-actuator noise model 110c, and a post-actuator noise model 110d.

The outside magnetic field model 110 is configured for, in response to an input of a unit white noise vector $\vec{w}$ containing white noise strengths w, outputting an outside magnetic field vector $\vec{b_{out}(s)}$ containing outside magnetic field strengths $b_{out}$ representing the strength of the outside magnetic field $B_{OUT}$ respectively at the magnetometers 26 (both coarse magnetometers 26a and fine magnetometers 26b) of the signal acquisition unit 18.

The outside magnetic field model 110 associated with a particular magnetometer 26 of the signal acquisition unit 18 may be characterized with the following state-space linear equations:

$$\dot{x}1(t)=A1\cdot x1(t)+B1\cdot w(t); \text{ and} \quad [6a]$$

$$b_{OUT}(t)=C1\cdot x1(t)+D1\cdot w(t), \quad [6b]$$

where x1(t) is a defined time-varying state vector of the outside magnetic field $B_{OUT}$; w(t) is a defined time-varying white noise strength; $b_{OUT}(t)$ is a strength of the time-varying outside magnetic field representing the strength of the outside magnetic field $B_{OUT}$ at the magnetometer 26; A1 is a defined constant state matrix of the outside magnetic field $B_{OUT}$; B1 is a defined constant input matrix of the outside magnetic field $B_{OUT}$; C1 is a defined constant output matrix of the outside magnetic field $B_{OUT}$; D1 is a defined constant feedthrough (or feedforward) matrix of the outside magnetic field $B_{OUT}$; and $\dot{x}1(t)$ is a time-varying derivative of the state vector x1(t).

Equations [6a]-[6b] can be equivalently written in frequency-form in accordance with equation [3], as follows:

$$b_{out}(s)=g1(s)\cdot w(s), \quad [7]$$

where s is the Laplace frequency domain variable; $b_{out}(s)$ is the Laplace transform of the time-varying outside magnetic field strength $b_{out}(t)$ at the magnetometer 26; w(s) is the Laplace transform of the time-varying white noise strength w(t); and g1(s) is an outside magnetic field transfer function expressed as $(C1(sI-A1)^{-1}B1+D1)$ in accordance with equation [5].

Thus, the outside magnetic field $B_{OUT}$ may use an outside magnetic field matrix transfer function G1(s) configured for, in response to an input of a unit white noise vector $\vec{w(s)}$ containing white noise strengths w(s), outputting an outside magnetic field vector $\vec{b_{out}(s)}$ containing outside magnetic field strengths $b_{out}(s)$ representing the strength of the outside magnetic field $B_{OUT}$ respectively at the magnetometers 26 of the signal acquisition unit 18. In the exemplary embodiment, equation [7] is used as a building block for generating the outside magnetic field matrix transfer function G1(s) from the outside magnetic field transfer functions g1(s), generating the unit white noise vector $\vec{w(s)}$ from the unit white noise strengths w(s), and generating the outside magnetic field vector $\vec{b_{out}(s)}$ from the outside magnetic field strengths $b_{out}(s)$, for all of the magnetometers 26 (both the coarse magnetometers 26a and fine magnetometers 26b) of the signal acquisition unit 18.

In particular, the outside magnetic field matrix transfer function G1(s) has a dimension N×N, where N is the total number of magnetometers 26. The diagonal entries of the outside magnetic field matrix transfer function G1(s) are populated with the outside magnetic field transfer functions g1(s):1 ... N(s), and the remaining entries of the outside magnetic field matrix transfer function G1(s) are unknown, but presumed to be null entries. The outside magnetic field transfer functions g1(s):1 ... N(s) may be divided between outside magnetic field transfer functions $g1^c(s)$:1 ... $N^c(s)$ corresponding to coarse magnetometers 26a, and outside magnetic field transfer functions $g1^f(s)$:1 ... $N^f(s)$ corresponding to fine magnetometers 26b (where $N^c$ is the number of coarse magnetometers 26a, $N^f$ is the number of fine magnetometers 26b, and where the superscripts c and f are indexes for the respective coarse magnetometers 26a and fine magnetometers 26b).

It follows that each of the unit white noise vector w(s) and the outside magnetic field vector $\vec{b_{out}(s)}$ has a dimension N, such that the unit white noise vector w(s) contains white noise strengths w(s):1 ... N, and the outside magnetic field vector $\vec{b_{out}(s)}$ contains outside magnetic field strengths $b_{out}(s)$:1 ... N(s). It should be noted that because the coarse magnetometers 26a may be more exposed to the outside magnetic field $B_{OUT}$ than the fine magnetometers 26, the outside magnetic field vector $\vec{b_{out}(s)}$ may contain strengths $b^c_{out}(s)$:1 ... $N^c(s)$ corresponding to the coarse magnetometers 26a that are generally much greater than the strengths $b^f_{out}(s)$:1 ... $N^f(s)$ corresponding to the fine magnetometers 26b.

Each of the outside magnetic field transfer functions g1(s) of the outside magnetic field matrix transfer G1(s) has a peak substantially at 0 Hz to represent the Earth's magnetic field (which is largely constant in time), and may also have peaks at 60 Hz, 120 Hz, 180 Hz, 240 Hz, etc., to represent noise peaks at 60 Hz and its harmonics. 60 Hz corresponds to the frequency of electrical power in the United States, and its harmonics (120 Hz, 180 Hz, 240 Hz, etc.) are generated when electromagnetic fields interact with real-world objects (chairs, tables, posts, etc.) and generate harmonics. In Europe, power comes in at 50 Hz, in which case, each of the outside magnetic field transfer functions g1(s) may have peaks at 0 Hz 50 Hz, 100 Hz, 150 Hz, etc.).

The pre-magnetometer noise model 110a is configured for, in response to an input of a unit white noise vector $\vec{w_a}$ containing white noise strengths $w_a$, outputting a pre-magnetometer noise vector $\vec{n_a}$ containing strengths $\vec{n_a}$ representing the strength of the pre-magnetometer noise $N_A$ respectively at the magnetometers 26 (both coarse magnetometers 26a and fine magnetometers 26b) of the signal acquisition unit 18.

The pre-magnetometer noise model 110a associated with a particular magnetometer 26 of the signal acquisition unit 18 may be characterized with the following state-space linear equations:

$$\dot{x}1_a(t) = A1_a \cdot x1_a + B1_a \cdot w_a(t); \text{ and} \qquad [8a]$$

$$n_a(t) = C1_a x1_a(t) + D1_a \cdot w_a(t), \qquad [12a]$$

where $x1_a(t)$ is a defined time-varying state vector of the pre-magnetometer noise at the magnetometer 26; $w_a(t)$ is a defined time-varying white noise strength; $n_a(t)$ is a strength of the time-varying pre-magnetometer noise representing the strength of the pre-magnetometer noise $N_A$ at the magnetometer 26; $A1_a$ is a defined constant state matrix of the pre-magnetometer noise $N_A$ at the magnetometer 26; $B1_a$ is a defined constant input matrix of the pre-magnetometer noise $N_A$ at the magnetometer 26; $C1_a$ is a defined constant output matrix of the pre-magnetometer noise $N_A$ at the magnetometer 26; $D1_a$ is a defined constant feedthrough (or feedforward) matrix of the pre-magnetometer noise $N_A$ at the magnetometer 26; and $\dot{x}1_a(t)$ is a time-varying derivative of the state vector $x1_a(t)$.

Equations [8a]-[8b] can be equivalently written in frequency-form in accordance with equation [3], as follows: [9] $n_a(s) = g1_a(s) \cdot w_a(s)$, where s is the Laplace frequency domain variable; $n_a(s)$ is the Laplace transform of the time-varying pre-magnetometer noise strength $n_a(t)$ at the magnetometer 26; $w_a(s)$ is the Laplace transform of the time-varying white noise strength $w_a(t)$; and $g1_a(s)$ is a pre-magnetometer noise transfer function expressed as $(C1_a(sI-A1_a)^{-1}B1_a+D1_a)$ in accordance with equation [5].

Thus, the pre-magnetometer noise model 110a uses a pre-magnetometer noise matrix transfer function $G1_a(s)$ configured for, in response to an input of a unit white noise vector $\overrightarrow{w_a(s)}$ containing white noise strengths $w_a(s)$, outputting a pre-magnetometer noise vector $\overrightarrow{n_a(s)}$ containing pre-magnetometer noise strengths $n_a(s)$ representing the strength of the pre-magnetometer noise $N_A$ respectively at the magnetometers 26 of the signal acquisition unit 18. In the exemplary embodiment, equation [9] is used as a building block for generating the pre-magnetometer noise matrix transfer function $G1_a(s)$ from the pre-magnetometer noise transfer functions $g1_a(s)$, generating the unit white noise vector $\overrightarrow{w_a(s)}$ from the unit white noise strengths $w_a(s)$, and generating the pre-magnetometer noise vector $\overrightarrow{n_a(s)}$ from the pre-magnetometer noise strengths $n_a(s)$, for all of the magnetometers 26 (both the coarse magnetometers 26a and fine magnetometers 26b) of the signal acquisition unit 18.

In particular, the pre-magnetometer noise matrix transfer function $G1_a(s)$ has a dimension N×N, where N is the total number of magnetometers 26. The diagonal entries of the pre-magnetometer noise matrix transfer function $G1_a(s)$ are populated with pre-magnetometer noise transfer functions $g1_a(s):1 \ldots N(s)$, and the remaining entries of the pre-magnetometer noise matrix transfer function $G1_a(s)$ are unknown, but presumed to be null entries. The pre-magnetometer noise transfer functions $g1_a(s):1 \ldots N(s)$ may be divided between pre-magnetometer noise transfer functions $g1^c_a(s):1 \ldots N^c(s)$ corresponding to coarse magnetometers 26a, and pre-magnetometer noise transfer functions $g1^f_a(s):1 \ldots N^c(s)$ corresponding to fine magnetometers 26b.

It follows that each of the unit white noise vector $\overrightarrow{w_a(s)}$ and the pre-magnetometer noise vector $\overrightarrow{n_a(s)}$ has a dimension N, such that the unit white noise vector $\overrightarrow{w_a(s)}$ contains white noise strengths $w_a:1 \ldots N$, and the pre-magnetometer noise vector $\overrightarrow{n_a(s)}$ contains pre-magnetometer strengths $n_a:1 \ldots N(s)$. It should be noted that the fine magnetometers 26a may have less noise than the coarse magnetometers 26b, and thus, the pre-magnetometer noise vector $\overrightarrow{n_a(s)}$ may contain strengths $n^c_a(s):1 \ldots N^c(s)$ corresponding to the coarse magnetometers 26a that are generally much greater than the strengths $n^f_a(s):1 \ldots N(s)$ corresponding to the fine magnetometers 26b.

The post-magnetometer noise model 110b is configured for, in response to an input of a unit white noise vector $\overrightarrow{wb}$ containing white noise strengths $w_b$, outputting a post-magnetometer noise vector $\overrightarrow{n_b}$ containing strengths $n_b$ representing the strength of the post-magnetometer noise $N_B$ respectively at the magnetometers 26 (both coarse magnetometers 26a and fine magnetometers 26b) of the signal acquisition unit 18.

The post-magnetometer noise model 110b associated with a particular magnetometer 26 of the signal acquisition unit 18 may be characterized with the following state-space linear equations:

$$\dot{x}1_b(t) = A1_b \cdot x1_b + B1_b \cdot w_b(t); \text{ and} \qquad [10a]$$

$$n_b(t) = C1_b x1_b(t) + D1_b \cdot w_b(t), \qquad [10a]$$

where $x1_b(t)$ is a defined time-varying state vector of the post-magnetometer noise at the magnetometer 26; $w_b(t)$ is a defined time-varying white noise strength; $n_b(t)$ is a strength of the time-varying post-magnetometer noise representing the strength of the post-magnetometer noise $N_B$ at the magnetometer 26; $A1_b$ is a defined constant state matrix of the post-magnetometer noise $N_B$ at the magnetometer 26; $B1_b$ is a defined constant input matrix of the post-magnetometer noise $N_B$ at the magnetometer 26; $C1_b$ is a defined constant output matrix of the post-magnetometer noise $N_B$ at the magnetometer 26; $D1_b$ is a defined constant feedthrough (or feedforward) matrix of the post-magnetometer noise $N_B$ at the magnetometer 26; and $\bar{x}1_b(t)$ is a time-varying derivative of the state vector $x1_b(t)$.

Equations [10a]-[10b] can be equivalently written in frequency-form in accordance with equation [3], as follows: [11]$n_b(s) = g1_b(s) \cdot w_b(s)$, where s is the Laplace frequency domain variable; $n_b(s)$ is the Laplace transform of the time-varying post-magnetometer noise strength $n_b(t)$ at the magnetometer 26; $w_b(s)$ is the Laplace transform of the time-varying white noise strength $w_b(t)$; and $g1_b(s)$ is a post-magnetometer noise transfer function expressed as $(C1_b(sI-A1_b)^{-1}B1_b+D1_b)$ in accordance with equation [5].

Thus, the post-magnetometer noise model 110b uses a post-magnetometer noise matrix transfer function $G1_b(s)$ configured for, in response to an input of a unit white noise vector $\overrightarrow{w_b(s)}$ containing white noise strengths $w_b(s)$, outputting a post-magnetometer noise vector $\overrightarrow{n_b(s)}$ containing post-magnetometer noise strengths $n_b(s)$ representing the strength of the post-magnetometer noise $N_B$ respectively at the magnetometers 26 of the signal acquisition unit 18. In the exemplary embodiment, equation [11] is used as a building block for generating the post-magnetometer noise matrix transfer function $G1_b(s)$ from the post-magnetometer noise transfer functions $g1_b(s)$, generating the unit white noise vector $\overrightarrow{w_b(s)}$ from the unit white noise strengths $w_b(s)$, and generating the post-magnetometer noise vector $\overrightarrow{n_b(s)}$ from the post-magnetometer noise strengths $n_b(s)$, for all of the magnetometers 26 (both the coarse magnetometers 26a and fine magnetometers 26b) of the signal acquisition unit 18.

In particular, the post-magnetometer noise matrix transfer function $G1_b(s)$ has a dimension N×N, where N is the total number of magnetometers 26. The diagonal entries of the post-magnetometer noise matrix transfer function $G1_b(s)$ are populated with post-magnetometer noise transfer functions $g1_b(s):1 \ldots N(s)$, and the remaining entries of the post-magnetometer noise matrix transfer function $G1_b(s)$ are unknown, but presumed to be null entries. The post-magnetometer noise transfer functions $g1_b(s):1 \ldots N(s)$ may be divided between post-magnetometer noise transfer functions $g1^c_b(s):1 \ldots N^c(s)$ corresponding to coarse magnetometers 26a, and post-magnetometer noise transfer functions $g1^f_b(s):1 \ldots N^c(s)$ corresponding to fine magnetometers 26b.

It follows that each of the unit white noise vector $\overrightarrow{w_b(s)}$ and the post-magnetometer noise vector $\overrightarrow{n_b(s)}$ has a dimension N, such that the unit white noise vector $\overrightarrow{w_b(s)}$ contains white noise strengths $w_b:1 \ldots N$, and the post-magnetometer noise vector $\overrightarrow{n_b(s)}$ contains post-magnetometer strengths $n_b:1 \ldots N(s)$. It should be noted that the fine magnetometers 26a may have less noise than the coarse magnetometers 26b, and thus, the post-magnetometer noise vector $\overrightarrow{n_b(s)}$ may contain strengths $n^c_b(s):1 \ldots N^c(s)$ corresponding to the coarse magnetometers 26a that are generally much greater than the strengths $n^f_b(s):1 \ldots N(s)$ corresponding to the fine magnetometers 26b.

The pre-actuator noise model 110c is configured for, in response to an input of a unit white noise vector $\overrightarrow{w_c}$ containing white noise strengths $w_c$, outputting a pre-actuator noise vector $\overrightarrow{n_c}$ containing pre-actuator noise strengths $n_c$ representing the strength of the pre-actuator noise $N_C$ respectively at the magnetic field actuators 28 of the signal acquisition unit 18.

The pre-actuator noise model 110c for a particular magnetometer 26 of the signal acquisition unit 18 may be characterized with the following state-space linear equations:

$$\dot{x1}_c(t) = A1_c \cdot x1_c + B1_c \cdot w_c(t); \text{ and} \quad [12a]$$

$$n_c(t) = C1_c \cdot x1_c(t) + D1_c \cdot w_c(t), \quad [12a]$$

where $x1_c(t)$ is a defined time-varying state vector of pre-actuator noise at the magnetometer 26; $w_c(t)$ is a defined time-varying white noise strength; $n_c(t)$ is a time-varying pre-actuator noise strength representing the strength of the pre-actuator noise $N_C$ at the magnetic field actuator 28; $A1_c$ is a defined constant state matrix of the pre-actuator noise $N_C$ at the magnetometer 26; $B1_c$ is a defined constant input matrix of the pre-actuator noise $N_C$ at the magnetometer 26; $C1_c$ is a defined constant output matrix of the pre-actuator noise $N_C$ at the magnetometer 26; $D1_c$ is a defined constant feedthrough (or feedforward) matrix of the pre-actuator noise $N_C$ at the magnetometer 26; and $\bar{x}1_c(t)$ is a time-varying derivative of the state vector $x1_c(t)$.

Equations [12a]-[12b] can be equivalently written in frequency-form in accordance with equation [3], as follows: [13] $n_c(s) = g1_c(s) \cdot w_c(s)$, where s is the Laplace frequency domain variable; $n_c(s)$ is the Laplace transform of the time-varying pre-actuator noise strength $n_c(t)$; $w_c(s)$ is the Laplace transform of the time-varying white noise strength $w_c(t)$; and $g1_c(s)$ is a pre-actuator noise transfer function expressed as $(C1_c(sI-A1_c)^{-1}B1_c + D1_c)$ in accordance with equation [5].

Thus, the pre-actuator noise model 110c may use a pre-actuator noise matrix transfer function $G1_c(s)$ configured for, in response to an input of a unit white noise vector $\overrightarrow{w_c(s)}$ containing white noise strengths $w_c(s)$, outputting a pre-actuator noise vector $\overrightarrow{n_c(s)}$ containing pre-actuator noise strengths $n_c(s)$ representing the strength of the pre-actuator noise $N_C$ respectively at the magnetic field actuators 28 of the signal acquisition unit 18. In the exemplary embodiment, equation [13] is used as a building block for generating the pre-actuator noise matrix transfer function $G1_c(s)$ from the pre-actuator noise transfer functions $g1_c(s)$, generating the unit white noise vector $\overrightarrow{w_c(s)}$ from the unit white noise strengths $w_c(s)$, and generating the pre-actuator noise vector $\overrightarrow{n_c(s)}$ from the pre-actuator noise strengths $n_c(s)$, for all of the magnetic field actuators 28 of the signal acquisition unit 18.

In particular, the pre-actuator noise matrix transfer function $G1_c(s)$ has a dimension M×M, where M is the total number of magnetic field actuators 28. The diagonal entries of the pre-actuator noise matrix transfer function $G1_c(s)$ are populated with pre-actuator noise transfer functions $g1_c(s):1 \ldots M(s)$, and the remaining entries of the pre-actuator noise matrix transfer function $G1_c(s)$ are unknown, but presumed to be null entries. It follows that each of the unit white noise vector $\overrightarrow{w_c(s)}$ and the post-actuator noise vector $\overrightarrow{n_c(s)}$ has a dimension M, such that the unit white noise vector $\overrightarrow{w_c(s)}$ contains white noise strengths $w_c:1 \ldots M$, and the pre-actuator noise vector $ne(s)$ contains pre-actuator noise strengths $n_c(s):1 \ldots M(s)$.

The post-actuator noise model 110d is configured for, in response to an input of a unit white noise vector $\overrightarrow{w_d}$ containing white noise strengths $w_d$, outputting a post-actuator noise vector $\overrightarrow{n_d}$ containing post-actuator noise strengths $n_d$ representing the strength of the post-actuator noise $N_D$ respectively at the magnetic field actuators 28 of the signal acquisition unit 18.

The post-actuator noise model 110d for a particular magnetometer 26 of the signal acquisition unit 18 may be characterized with the following state-space linear equations:

$$\dot{x1}_d(t) = A1_d \cdot x1_d + B1_d \cdot w_d(t); \text{ and} \quad [14a]$$

$$n_d(t) = C1_d \cdot x1_d(t) + D1_d \cdot w_d(t), \quad [14a]$$

where $x1_d(t)$ is a defined time-varying state vector of post-actuator noise at the magnetometer 26; $w_d(t)$ is a defined time-varying white noise strength; $n_d(t)$ is a time-varying post-actuator noise strength representing the strength of the post-actuator noise $N_D$ at the magnetic field actuator 28; $A1_d$ is a defined constant state matrix of the post-actuator noise $N_D$ at the magnetometer 26; $B1_d$ is a defined constant input matrix of the post-actuator noise $N_D$ at the magnetometer 26; $C1_d$ is a defined constant output matrix of the post-actuator noise $N_D$ at the magnetometer 26; $D1_d$ is a defined constant feedthrough (or feedforward) matrix of the post-actuator noise $N_D$ at the magnetometer 26; and $\bar{x}1_d(t)$ is a time-varying derivative of the state vector $x1_d(t)$.

Equations [14a]-[14b] can be equivalently written in frequency-form in accordance with equation [3], as follows: [15] $n_d(s) = g1_d(s) \cdot w_d(s)$, where s is the Laplace frequency domain variable; $n_d(s)$ is the Laplace transform of the time-varying post-actuator noise strength $n_d(t)$; $w_d(s)$ is the Laplace transform of the time-varying white noise strength $w_d(t)$; and $g1_d(s)$ is a post-actuator noise transfer function expressed as $(C1_d(sI-A1_d)^{-1}B1_d+D1_d)$ in accordance with equation [5].

Thus, the post-actuator noise model 110*d* may use a post-actuator noise matrix transfer function $G1_d(s)$ configured for, in response to an input of a unit white noise vector $\overrightarrow{w_d(s)}$ containing white noise strengths $w_d(s)$, outputting a post-actuator noise vector $\overrightarrow{n_d(s)}$ containing post-actuator noise strengths $n_d(s)$ representing the strength of the post-actuator noise $N_D$ respectively at the magnetic field actuators 28 of the signal acquisition unit 18. In the exemplary embodiment, equation [15] is used as a building block for generating the post-actuator noise matrix transfer function $G1_d(s)$ from the post-actuator noise transfer functions $g1_d(s)$, generating the unit white noise vector $\overrightarrow{w_d(s)}$ from the unit white noise strengths $w_d(s)$, and generating the post-actuator noise vector $\overrightarrow{n_d(s)}$ from the post-actuator noise strengths $n_d(s)$, for all of the magnetic field actuators 28 of the signal acquisition unit 18.

In particular, the post-actuator noise matrix transfer function $G1_d(s)$ has a dimension M×M, where M is the total number of magnetic field actuators 28. The diagonal entries of the post-actuator noise matrix transfer function $G1_d(s)$ are populated with post-actuator noise transfer functions $g1_d(s):1 \ldots M(s)$, and the remaining entries of the post-actuator noise matrix transfer function $G1_d(s)$ are unknown, but presumed to be null entries. It follows that each of the unit white noise vector $\overrightarrow{w_d(s)}$ and the post-actuator noise vector $\overrightarrow{n_d(s)}$ has a dimension M, such that the unit white noise vector $\overrightarrow{w_d(s)}$ contains white noise strengths $w_c:1 \ldots M$, and the post-actuator noise vector $\overrightarrow{n_d(s)}$ contains post-actuator noise strengths $n_d(s):1 \ldots M(s)$.

Thus, it can be appreciated from the foregoing that all of the real-world noise sources are encapsulated in the noise models 110, and in particular, the noise matrix transfer functions $G1(s)$, $G1_a(s)$, $G1_b(s)$, $G1_c(s)$, and $G1_d(s)$. The parameters of the noise matrix transfer functions $G1(s)$, $G1_a(s)$, $G1_b(s)$, $G1_c(s)$, and $G1_d(s)$, and in particular the matrices A, B, C, and D, may be defined to reflect the characteristics of real-world noise sources based on collected experimental data (e.g., by fitting filtering functions to experimental spectra measurements from the magnetometers 26 or measurements taken at the magnetic field actuators 28). For example, with respect to the outside magnetic field matrix transfer function $G1(s)$, the amplitude and width of each peak can be selected to reflect knowledge about the environment, and this knowledge can be attained by experimental measurements, by simulations, by calculations, or by estimates. For example, the width of the peak can represent the actual spread in frequencies around each peak measured in experimental data.

In an optional embodiment, any of the noise matrix transfer functions $G1(s)$, $G1_a(s)$, $G1_b(s)$, $Gc(s)$, and $G1_d(s)$ may be configured for separating the noise into common-mode noise (noise that appears the same or substantially similar at two or more magnetometers 26 or two or more magnetic field actuators 28, such as from the outside magnetic field $B_{OUT}$ for the magnetometers 26), and independent noise (noise that is not common between magnetometers 26 or between magnetic field actuators 28, such as thermal noise that is statistically independent from one magnetometer 26 to another or from one magnetic field actuators 28 to another).

Common mode noise may be represented by setting two or more entries in a particular noise matrix transfer function $G1(s)$, $G1_a(s)$, $G1_b(s)$, $Gc(s)$, and $G1_d(s)$ corresponding to two or more magnetometers 26 or two or more magnetic field actuators 28 to have the same noise strengths (i.e., same A, B, C, and D matrices), while independent noise may be represented by having two or more entries in the particular noise matrix transfer function $G1(s)$, $G1_a(s)$, $G1_b(s)$, $Gc(s)$, and $G1_d(s)$ corresponding to two or more magnetometers 26 or two or more magnetic field actuators 28 independent of each other. Each noise transfer function $g1(s)$, $g1_a(s)$, $g1_b(s)$, $gc(s)$, and $g1_d(s)$ in a particular noise matrix transfer function $G1(s)$, $G1_a(s)$, $G1_b(s)$, $Gc(s)$, and $G1_d(s)$ can have common-mode components, can have independent noise components, or can have the sum of both, the latter of which may be implemented by combining common and independent entries within the particular noise matrix transfer function $G1(s)$, $G1_a(s)$, $G1_b(s)$, $Gc(s)$, and $G1_d(s)$. For example, the diagonal entries of a noise matrix transfer function 110 may be populated with independent noise strengths, while an additional column (not shown) in the particular noise matrix transfer function $G1(s)$, $G1_a(s)$, $G1_b(s)$, $Gc(s)$, and $G1_d(s)$ may be populated with the same noise strengths.

The magnetic field summation function 120*a* is configured for, in response to an input of the outside magnetic field vector $\overrightarrow{b_{out}(s)}$ and a noisy actuated magnetic field vector $\overrightarrow{b'_{act}(s)}$ (containing noisy actuated magnetic field strengths $\overrightarrow{b'_{act}(s)}$ representing the strength of the noisy actuated magnetic field $B'_{ACT}$ at the magnetometers 26 of the signal acquisition unit 18) received from the actuated magnetic field model 114 (in this case, an actuated magnetic field matrix transfer function $G3(s)$ described in further detail below), outputting a total residual magnetic field vector $\overrightarrow{b_{tot}(s)}$ containing total residual magnetic field strengths $b_{tot}(s)$ representing the strength of the total residual magnetic field $B_{TOT}$ respectively at the magnetometers 26 (both the coarse magnetometers 26*a* and the fine magnetometers 26*b*) of the signal acquisition unit 18.

The total residual magnetic field vector $\overrightarrow{b_{tot}(s)}$ has a dimension of N, such that the total residual magnetic field vector $\overrightarrow{b_{tot}(s)}$ contains total residual magnetic field strengths $b_{tot}(s):1 \ldots N(s)$. It should be noted that because the outside magnetic field $B_{OUT}$ will be directly cancelled by the noisy actuated magnetic field $B'_{ACT}$ at the fine magnetometers 26*b*, with residual cancellation of the outside magnetic field $B_{OUT}$ at the coarse magnetometers 26*a*, the total residual magnetic field vector $\overrightarrow{b_{tot}(s)}$ may contain total residual magnetic field strengths $b^c_{tot}(s):1 \ldots N^c(s)$ corresponding to coarse magnetometers 26*a* that generally become much greater than the total residual magnetic field strengths $b^f_{tot}(s):1 \ldots N^f(s)$ corresponding to the fine magnetometers 26*b*.

The magnetic field summation function 120*b* is configured for, in response to an input of the total residual magnetic field vector $\overrightarrow{b_{tot}(s)}$ and an input of the pre-magnetometer noise vector $\overrightarrow{n_a(s)}$, outputting a noisy total residual magnetic field vector $\overrightarrow{b'_{tot}(s)}$ containing noisy total residual magnetic field strengths $\overrightarrow{b'_{tot}(s)}$ representing the strength of the total residual magnetic field $B_{TOT}$ with pre-magnetometer noise respectively at the magnetometers 26 (both the coarse magnetometers 26a and the fine magnetometers 26b) of the signal acquisition unit 18. The noisy total residual magnetic field vector $\vec{b'}_{tot}(s)$ has a dimension of N, such that the noisy total residual magnetic field vector $\vec{b'}_{tot}(s)$ contains noisy total residual magnetic field strengths $b'_{tot}(s):1 \ldots N(s)$, which may be further divided between noisy total residual magnetic field strengths $b'^c_{tot}(s):1 \ldots N^c(s)$ corresponding to the coarse magnetometers 26a and noisy total residual magnetic field strengths $b'^f_{tot}(s):1 \ldots N^f(s)$ corresponding to the fine magnetometers 26b.

The magnetometer model 112 is configured for quantifying the physical properties of the magnetometers 26 (both the coarse magnetometers 26a and the fine magnetometers 26b). In particular, the magnetometer model 112 is configured for, in response to an input of a noisy total residual magnetic field vector $\vec{b'}_{tot}$ containing noisy total residual magnetic field strengths $b'_{tot}$ representing the strength of the total residual magnetic field $B_{TOT}$ with pre-magnetometer noise $N_A$ respectively at the magnetometers 26 of the signal acquisition unit 18, outputting a measured total residual magnetic field vector $\vec{b}_{tot\text{-}meas}$ containing measured total residual magnetic field strengths $b_{tot\text{-}meas}$ representing the strength of the measured total residual magnetic field $B_{TOT\text{-}MEAS}$ respectively from the magnetometers 26 (both coarse magnetometers 26a and fine magnetometers 26b) of the signal acquisition unit 18.

The magnetometer model 112 for a particular magnetometer 26 may be characterized with the following state-space linear equations:

$$\dot{x}2(t) = A2 \cdot x2(t) + B2 \cdot b'_{tot}(t); \text{ and} \quad [16a]$$

$$b_{tot\text{-}meas}(t) = C2 \cdot x2(t) + D2 \cdot b'_{tot}(t), \quad [16b]$$

where $x2(t)$ is a defined time-varying state vector of a magnetometer 26; $b'_{tot}(t)$ is a time-varying noisy total residual magnetic field strength output by the summation function 120b; $b_{tot\text{-}meas}(t)$ is a time-varying measured total residual magnetic field strength representing the strength of the measured total residual magnetic field $B_{TOT\text{-}MEAS}$ respectively from the magnetometer 26; A2 is a defined constant state matrix of the magnetometer 26; B2 is a defined constant input matrix of the magnetometer 26; C2 is a defined constant output matrix of the magnetometer 26; D2 is a defined constant feedthrough (or feedforward) matrix of the magnetometer 26; and $\dot{x}2(t)$ is a time-varying derivative of the state vector $x2(t)$.

Equations [16a]-[16b] can be equivalently written in frequency-form in accordance with equation [3], as follows: [17]$b_{tot\text{-}meas}(s) = g2(s) \cdot b'_{tot}(s)$, where s is the Laplace frequency domain variable; $b_{tot\text{-}meas}(s)$ is the Laplace transform of the time-varying measured total residual magnetic field strength $b_{tot\text{-}meas}(t)$; $b'_{tot}(s)$ is the Laplace transform of the time-varying noisy total residual magnetic field strength $b'_{tot}(t)$; and $g2(s)$ is a measured total residual magnetic field transfer function expressed as $(C2(sI-A2)^{-1}B2+D2)$ in accordance with equation [5].

Thus, the magnetometer model 112 may use a magnetometer matrix transfer function G2(s) configured for, in response to an input of the noisy total residual magnetic field vector $\vec{b'}_{tot}(s)$, outputting a measured total residual magnetic field vector $\vec{b}_{tot\text{-}meas}(s)$ containing measured total residual magnetic field strengths $b_{tot\text{-}meas}(s)$ representing the strength of the measured total residual magnetic field $B_{TOT\text{-}MEAS}$ respectively from the magnetometers 26 (both coarse magnetometers 26a and fine magnetometers 26b) of the signal acquisition unit 18. In the exemplary embodiment, equation [15] is used as a building block for generating the magnetometer matrix transfer function G2(s) from the magnetometer transfer functions g2(s), generating the noisy total residual magnetic field vector $\vec{b'}_{tot}(s)$ from the noisy total residual magnetic field strengths $b'_{tot}(s)$, and generating the measured total residual magnetic field vector $\vec{b}_{tot\text{-}meas}(s)$ from the measured total residual magnetic field strengths $b_{tot\text{-}meas}(s)$, for all of the magnetometers 26.

In particular, the magnetometer matrix transfer function G2(s) has a dimension N×N, where N is the total number of magnetometers 26. The diagonal entries of the magnetometer matrix transfer function G2(s) are populated with magnetometer transfer functions $g2(s):1 \ldots N(s)$, and the remaining entries of the magnetometer matrix transfer function G2(s) are unknown, but presumed to be null entries. The magnetometer transfer functions $g2(s):1 \ldots N(s)$ may be divided between coarse magnetometer transfer functions $g2^c(s):1 \ldots N^c(s)$ corresponding to the coarse magnetometers 26a, and fine magnetometer transfer functions $g2^f(s):1 \ldots N^f(s)$ corresponding to the fine magnetometers 26b.

It follows that each of the noisy total residual magnetic field vector $\vec{b'}_{tot}(s)$ and the measured total residual magnetic field vector $\vec{b}_{tot\text{-}meas}(s)$ has a dimension N, such that the noisy total residual magnetic field vector $\vec{b'}_{tot}(s)$ contains noisy total residual magnetic field strengths $b'_{tot}(s):1 \ldots N$, and the measured total residual magnetic field vector $\vec{b}_{tot\text{-}meas}(s)$ contains measured total residual magnetic field strengths $b_{tot\text{-}meas}(s):1 \ldots N(s)$, which may be further divided between measured total residual magnetic field strengths $b^c_{tot\text{-}meas}(s):1 \ldots N^c(s)$ corresponding to the coarse magnetometers 26a and measured total residual magnetic field strengths $b^f_{tot\text{-}meas}(s):1 \ldots N^f(s)$ corresponding to the fine magnetometers 26b.

The parameters of the noise matrix transfer function G2(s), and in particular the matrices A, B, C, and D, may be defined to reflect the physical properties of each type of magnetometer 26, and can be derived from experiments, from simulations, calculations, or estimates, or in the case of off-the-shelf magnetometers 26, from specification sheets for those magnetometers 26 from the manufacturer.

The magnetic field summation function 120c is configured for, in response to an input of the measured total residual magnetic field vector $\vec{b}_{tot\text{-}meas}(s)$ and an input of the post-magnetometer noise vector $\vec{n}_b(s)$, outputting a noisy measured total residual magnetic field vector $\vec{b'}_{tot\text{-}meas}(s)$ containing noisy measured total residual magnetic field strengths $b'_{tot\text{-}meas}(s)$ representing the strength of the measured total residual magnetic field $B_{TOT\text{-}MEAS}$ with post-magnetometer noise $N_B$ respectively from the magnetometers 26 (both the coarse magnetometers 26a and the fine magnetometers 26b) of the signal acquisition unit 18. The noisy measured total residual magnetic field vector $\vec{b'}_{tot\text{-}meas}(s)$ has a dimension of N, such that the noisy measured total residual magnetic field vector $\vec{b'}_{tot\text{-}meas}(s)$ contains noisy measured total residual magnetic field strengths $b'_{tot\text{-}meas}(s):1 \ldots N(s)$, which may be further divided between noisy measured total residual magnetic field $b'^c_{tot\text{-}meas}(s):1 \ldots N^c(s)$ corresponding to the coarse magnetometers 26a and noisy measured total residual magnetic field $b'^f_{tot\text{-}meas}(s):1 \ldots N^f(s)$ corresponding to the fine magnetometers 26b.

The magnetic field summation function 120d is configured for, in response to an input of an actuation control vector c(s) containing actuation control strengths c(s) representing the strengths of actuation control signals C generated by the optimal linear controllers 56 of the signal acquisition unit 18) from the optimal linear control model 118 (in this case, an optimal linear control matrix transfer function K(s) described in further detail below) and the pre-magnetometer noise vector $\vec{c}(s)$, outputting a noisy actuation control vector $\vec{c'}(s)$ containing noisy actuation control strengths c'(s) representing the strengths of actuation control signals C' with pre-actuator noise $N_C$ respectively generated by the optimal linear controllers 56 of the signal acquisition unit 18. The noisy actuation control vector $\vec{c'}(s)$ has a dimension of M, such that the noisy actuation control vector $\vec{c'}(s)$ contains noisy actuation control strengths c'(s):1 ... M(s).

The actuated magnetic field model 114 is configured for, in response to an input of a noisy actuation control vector $\vec{c'}$ containing actuation control strengths c' representing actuation control signals C' with pre-actuator noise $N_C$ respectively generated by the optimal linear controllers 56 of the signal acquisition unit 18, outputting a noisy actuated magnetic field vector $\vec{b'}_{act}$ containing noisy actuated magnetic field strengths $b'_{act}$ representing the strength of the noisy actuated magnetic field $B'_{ACT}$ respectively generated by the magnetic field actuators 28 respectively at the magnetometers 26 (both coarse magnetometers 26a and fine magnetometers 26b) of the signal acquisition unit 18.

The actuated magnetic field model 114 comprises a magnetic field actuator model 114a configured for quantifying the physical properties of the magnetic field actuators 28 and a matrix of influence 114b configured for linearly mapping the noisy actuated magnetic field $B'_{ACT}$ generated by the magnetic field actuators 28 to the magnetometers 26.

The magnetic field actuator model 114a is configured for quantifying the physical properties of the magnetic field actuators 28 using an actuator matrix transfer function G3(s). In particular, the magnetic field actuator model 114a is configured for, in response to an input of the noisy actuation control vector $\vec{c'}$, outputting an actuation vector $\vec{s}_{act}$ containing actuation strengths $s_{act}$ representing the actuation strengths $S_{ACT}$ respectively of the magnetic field actuators 28 of the signal acquisition unit 18.

The magnetic field actuator model 114a may be characterized for a particular magnetic field actuator 28 with the following state-space linear equations:

$$\dot{x}3(t) = A3 \cdot \dot{x}3(t) + B3 \cdot c'(t); \text{ and} \quad [18a]$$

$$s_{act}(t) = C3 \cdot \dot{x}3(t) + D3 \cdot c'(t), \quad [18b]$$

where x3(t) is a defined time-varying state vector of a magnetic field actuator; c'(t) is a time-varying noisy actuation control strength output by the summation function 120c; $s_{act}(t)$ is a time-varying actuation strength representing the actuation strength $S_{ACT}(t)$ of the magnetic field actuator 28; A2 is a defined constant state matrix of the magnetic field actuator 28; B2 is a defined constant input matrix of the magnetic field actuator 28; C2 is a defined constant output matrix of the magnetic field actuator 28; D2 is a defined constant feedthrough (or feedforward) matrix of the magnetic field actuator 28; and $\dot{x}2(t)$ is a time-varying derivative of the state vector x2(t).

Equations [18a]-[18b] can be equivalently written in frequency-form in accordance with equation [3], as follows: $[19] s_{act}(s) = g3(s) \cdot c'(s)$, where s is the Laplace frequency domain variable; $s_{act}(s)$ is the Laplace transform of the time-varying actuation strength $s_{act}(t)$; c'(s) is the Laplace transform of the time-varying noisy actuation control strength c'(t); and g3(s) is an actuator strength transfer function expressed as $(C3(sI-A3)^{-1}B3+D3)$ in accordance with equation [5].

Thus, the magnetic field actuator model 114a may use an actuator matrix transfer function G3(s) configured for, in response to an input of the noisy actuation control vector $\vec{c'}(s)$, outputting an actuation vector $\vec{s}_{act}(s)$ containing strengths $s_{act}(s)$ reflecting actuation strengths $S_{ACT}$ of the magnetic field actuators 28 of the signal acquisition unit 18. In the exemplary embodiment, equation [17] is used as a building block for generating the actuator matrix transfer function G3(s) from the actuator transfer functions g3(s), generating the noisy actuation control vector $\vec{u'}(s)$ from the noisy actuation control strengths c'(s), and generating the actuation vector $\vec{s}_{act}(s)$ from the actuation strengths $s_{act}(s)$, for all of the magnetic field actuators 28.

In particular, the actuator matrix transfer function G3(s) has a dimension M×M, where M is the total number of magnetic field actuators 28. The diagonal entries of the actuator matrix transfer function G3(s) are populated with actuator transfer functions g3(s):1 ... M(s), and the remaining entries of the actuator matrix transfer function G3(s) are unknown, but presumed to be null entries. It follows that each of the noisy actuation control vector $\vec{c'}(s)$ and the actuation vector $\vec{s}_{act}(s)$ has a dimension M, such that the noisy actuation control vector $\vec{c'}(s)$ contains actuation control strengths c'(s):1 ... M, and the actuation vector $\vec{s}_{act}(s)$ contains actuation strengths $s_{act}(s):1 \ldots M(s)$.

The parameters of the noise matrix transfer function G3(s), and in particular the matrices A, B, C, and D, may be defined to reflect the physical properties of each of the magnetic field actuators 28, and can be derived from experiments, from simulations, calculations, or estimates, or in the case of off-the-shelf magnetic field actuators 28, from specification sheets for those magnetic field actuators 28 from the manufacturer.

The magnetic field summation function 120d is configured for, in response to an input of the actuation vector $\vec{s}_{act}(s)$ and an input of the post-actuator noise vector d(s), outputting a noisy actuation vector $\vec{s'}_{act}(s)$ containing noisy actuation strengths $s'_{act}(s)$ representing noisy actuation strengths with post-actuator noise $N_B$ respectively at the magnetic field actuators 28 of the signal acquisition unit 18. The noisy actuation vector $\vec{s'}_{act}(s)$ has a dimension of M, such that the noisy actuation vector $\vec{s'}_{act}(s)$ contains noisy actuation strengths $s'_{act}(s):1 \ldots M(s)$.

The matrix of influence 114b represents how each actuator 28 affects each magnetometer 26. The matrix of influence 114b is configured for, in response to an input of the noisy actuation vector $\vec{s'}_{act}(s)$, outputting a noisy actuated magnetic field vector $\vec{b'}_{act}(s)$ containing noisy actuated magnetic field strengths $b'_{act}(s)$ representing the strength of the noisy actuated magnetic field $B'_{ACT}$ respectively generated by the magnetic field actuators 28 respectively at the magnetometers 26 (both coarse magnetometers 26a and fine magnetometers 26b) of the signal acquisition unit 18.

The matrix of influence 114b has a dimension N×M, where N is the total number of magnetometers 26 and M is the total number of magnetic field actuators 28. The entries of the matrix of influence 114b are populated with linear transfer functions Rjk that spatially couple a location j of each magnetic field actuator 28 with a location k of each magnetometer 26. For example, if the location k of a particular magnetometer 26 is immediately adjacent a location j of a particular, magnetic field actuator 28, the linear transfer function Rjk that spatially couples the location j of that magnetic field actuator 28 with the location k of that magnetometer 26 will be relatively large. Conversely, if the location k of a particular magnetometer 26 is far from a location j of a particular magnetic field actuator 28, the linear transfer function Rjk that spatially couples the location j of that magnetic field actuator 28 with the location k of that magnetometer 26 will be relatively small.

It follows that the noisy actuated magnetic field vector $\vec{b'}_{act}(s)$ output by the matrix influence 114b has a dimension N, such that the noisy actuated magnetic field vector $\vec{b'}_{act}(s)$ contains noisy actuated magnetic field strengths $b'_{act}(s):1 \ldots N$. It should be noted that because the magnetic field actuators 28 are located closer to the fine magnetometers 26b than the coarse magnetometers 26a, such that the outside magnetic field $B_{OUT}$ can be more effectively cancelled by the noisy actuated magnetic field $B'_{ACT}$ at the fine magnetometers 26b, with residual cancellation of the outside magnetic field $B_{OUT}$ at the coarse magnetometers 26a, the noisy actuated magnetic field vector $\vec{b'}_{act}(s)$ may contain noisy outside magnetic field strengths $b'^{C}_{out}(s):1 \ldots N^{C}(s)$ corresponding to coarse magnetometers 26a that generally become much greater than the outside magnetic field strengths $b^{f}_{out}(s):1 \ldots N^{f}(s)$ corresponding to the fine magnetometers 26b.

The linear transfer functions Rjk of the matrix of influence 114b may be determined by experimental means (its coefficients can be measured), or it can be calculated from simulations (e.g. from Maxwell's equations), or it can be determined by a combination of experiments, simulations, calculations and estimates.

The magnetic field estimation function 122, in response to an input of the noisy measured total residual magnetic field vector $\vec{b'}_{tot-meas}(s)$ and an input of a control vector $\vec{c}(s)$ (containing strengths c(s) representing control signals C respectively generated by the plurality of optimal linear controllers 56 used in the optimal linear feedback control loop 100 of the signal acquisition unit 18) from the optimal linear control model 118 (in this case, an optimal linear control matrix transfer function (described in further detail below), outputting an estimated total residual magnetic field vector $\vec{b^{f}}_{tot-est}(s)$ containing strengths $b^{f}_{tot-est}(s)$ representing an estimated total residual magnetic field $B^{f}_{TOT-EST}$ respectively at the fine magnetometers 26b. In an exemplary embodiment, the strengths $b'^{c}_{tot-meas}(s)$ of the noisy measured total residual magnetic field vector $\vec{b'^{c}}_{tot-meas}(s)$ associated with the coarse magnetometers 26a and the strengths $b^{tf}_{tot-meas}(s)$ of the noisy measured total residual magnetic field vector $\vec{b^{tf}}_{tot-meas}(s)$ associated with only the fine magnetometers 26b that are in-range are input into the magnetic field estimation function 122.

The magnetic field estimation function 122 utilizes an input matrix of dimension $N^{F}\times(N+M)$. As set forth above, $N^{F}$ is the number of fine magnetometers 26b, N is the total number of magnetometers 26 (both coarse magnetometers 26 and fine magnetometers 26b), and M is the number of magnetic field actuators 28. The entries of each row vector in the input matrix are populated with the available strengths $b'_{tot-meas}(s)$ of the noisy measured total residual magnetic field vector $\vec{b'}_{tot-meas}(s)$ (up to an N number) (i.e., the noisy measured total residual magnetic field strengths $b^{c}_{tot-est}(s)$ associated with the coarse magnetometers 26a and the noisy measured total residual magnetic field strengths $b^{f}_{tot-est}(s)$ associated with the fine magnetometers 26b that are in-range) and the M number of strengths c(s) of the control vector $\vec{c}(s)$. The estimated total residual magnetic field vector $\vec{b^{f}}_{tot-est}(s)$ has a dimension of $N^{F}$ such that the estimated total residual magnetic field vector $\vec{b^{f}}_{tot-est}(s)$ contains strengths $b^{f}_{tot-est}(s):1 \ldots N^{F}(s)$.

In an alternative embodiment, an estimated total residual magnetic field vector $\vec{b}_{tot-est}(s)$ output by the magnetic field estimation function 122 represents an estimated total residual magnetic field $B_{TOT-EST}$ respectively at all of the magnetometers 26 (both the coarse magnetometers 26a and the fine magnetometers 26b). In this case, the estimated total residual magnetic field vector $\vec{b}_{tot-est}(s)$ may have a dimension of N, such that the estimated total residual magnetic field vector $\vec{b}_{tot-est}(s)$ contains strengths $b_{tot-est}(s):1 \ldots N(s)$.

In one embodiment, the strengths $b'_{tot-meas}(s)$ of the noisy measured total residual magnetic field vector $\vec{b'}_{tot-meas}(s)$ input into the magnetic field estimation function 122 are weighted based on the operational state of the magnetometer transfer functions g2(s) associated with the fine magnetometers 26b. The magnetic field estimation function 122 or another function (not shown) may define variables that track the operational state of magnetometer transfer functions g2(s) (e.g., when they are in the linear operating range, are in an unsaturated non-linear operating range, or are saturated) and modifying these variables as the states of the magnetometer transfer functions g2(s) during optimization of the optimal linear control model 118. The weightings of the strengths $b'_{tot-meas}(s)$ of the noisy measured total residual magnetic field vector $\vec{b'}_{tot-meas}(s)$ input into the magnetic field estimation function 122 may then be set accordingly (e.g., a weight of 1 for noisy measured total residual magnetic field $b^{tf}_{tot-meas}(s)$ associated with fine magnetometers 26b that are in the linear operating range, a weight between 0 and 1 for noisy measured total residual magnetic field $b^{tf}_{tot-meas}(s)$ associated with fine magnetometers 26b that are in the non-linear operating range, and 0 for noisy measured total residual magnetic field $b^{tf}_{tot-meas}(s)$ associated with fine magnetometers 26b that are saturated).

This weighting technique allows the nonlinear physics of fine magnetometers 26b to be captured by the optimal linear feedback control loop 100, as compared to "linearizing" the optimal linear feedback control loop 100, which would not allow it to cover the range of operational states of the fine magnetometers 26b that is necessary for a practical implementation of the signal acquisition unit 18. Conversely, if the optimal linear feedback control loop 100 were left in its base nonlinear form, it would require the use of nonoptimal linear control design techniques, which are not practical (would require so much computation time that neither the control design nor its practical implementation would be possible).

Further details of various techniques for estimating a total residual magnetic field at fine magnetometers based on total residual magnetic field measurements acquired from magnetometers, and the weighting of fine magnetometers based on their operational state are described in U.S. Provisional Application Ser. No. 62/975,693, entitled "Nested and Parallel Feedback Control Loops For Ultra-Fine Measurements of Magnetic Fields From the Brain Using a Wearable MEG System", U.S. Provisional Application Ser. No. 62/975,719, entitled "Estimating the Magnetic Field at Distances From Direct Measurements to Enable Fine Sensors to Measure the Magnetic Field from the Brain by Using a Wearable MEG System", and/or U.S. Provisional Application Ser. No. 62/975,723, entitled "Algorithms that Exploit Maxwell's Equations and Geometry to Reduce Noise for Ultra-Fine Measurements of Magnetic Fields from the Brain Using a Wearable MEG System", which are expressly incorporated herein by reference.

The magnetic field selection function 124 is configured for, in response to an input of the total residual magnetic field vector $\overrightarrow{b_{tot}(s)}$ output by the summation function 120a, outputting a fine total residual magnetic field vector $\overrightarrow{b^f_{tot}(s)}$ containing total residual magnetic field strengths $b^f_{tot}(s)$ representing the total residual magnetic field $B^F_{TOT}$ respectively at the fine magnetometers 26b of the signal acquisition unit 18. The magnetic field selection function 124 comprises a matrix transfer function of dimension $N^F \times N$, where $N^F$ is the total number of fine magnetometers 26b and N is the total number of magnetometers 26 (both coarse magnetometers 26a and fine magnetometers 26b). The matrix transfer function is populated with linear weighting functions (preferably 1 for the total residual magnetic field strengths $b^f_{tot}(s)$ representing the total residual magnetic field $B^f_{TOT}$ respectively at the fine magnetometers 26b, and 0 for the total residual magnetic field strengths $b^c_{tot}(s)$ representing the total residual magnetic field $B^C_{TOT}$ respectively at the coarse magnetometers 26a), such that the total residual magnetic field vector $\overrightarrow{b^f_{tot}(s)}$ output by the matrix transfer function contains only total residual magnetic field strengths $b^f_{tot}(s)$ representing the total residual magnetic field $B^f_{TOT}$ only at the fine magnetometers 26b. In the illustrated embodiment, this is accomplished by populating the diagonal entries of the matrix transfer function with weightings of 1, and arranging the entries 1 to $N^F$ of the total residual magnetic field vector $\overrightarrow{b_{tot}(s)}$ with total residual magnetic field strengths $b^f_{tot}(s)$ representing the total residual magnetic field $B^f_{TOT}$ respectively at the fine magnetometers 26b.

The magnetic field integration function 126 is configured for, in response to an input of the fine total residual magnetic field vector $\overrightarrow{b^f_{tot}(s)}$, outputting a time-integrated total residual magnetic field vector $\overrightarrow{\int b^f_{tot}(s)}$ containing time-integrated total residual magnetic field strengths $\int b^f_{tot}(s)$ representing the strengths of the time-integration of the total residual magnetic field $B^f_{TOT}$ at the fine magnetometers 26b of the signal acquisition unit 18. The magnetic field integration function 126 may compute an exact time-integral of the fine total residual magnetic field vector $\overrightarrow{\int b^f_{tot}(s)}$ by a variable transformation (not shown) or may compute an approximate time-integral of the fine total residual magnetic field vector $\overrightarrow{\int b^f_{tot}(s)}$ with an approximation parameter E, which as will be described in further detail below allows the magnetic field integration function 126 to be more simply implemented.

The weighted metric model 116 is configured for quantifying and optimizing a total performance metric of the optimal linear control model 118 using an optimal linear control matrix transfer function G4. In particular, the weighted metric model 116 is configured, in response an input of a fine total residual magnetic field vector $\overrightarrow{b^f_{tot}}$ containing fine total residual magnetic field strengths $b^f_{tot}$ representing the strengths of the total residual magnetic field $B^F_{TOT}$ at the fine magnetometers 26b of the signal acquisition unit 18, an input of time-integrated total residual magnetic field vector $\overrightarrow{\int b^f_{tot}}$ containing time-integrated total residual magnetic field strengths $\int b^f_{tot}$ representing the strengths of the time-integration of the total residual magnetic field $B^F_{TOT}$ at the fine magnetometers 26b of the signal acquisition unit 18, and an input of an actuation control vector $\overrightarrow{c}$ containing actuation control strengths c representing the strength of the actuation control signals C respectively output by the optimal linear controllers 56 of the signal acquisition unit 18, and outputting a total performance metric vector $\overrightarrow{z}$ containing weighted performance metric strengths z of the fine total residual magnetic field strengths $b^f_{tot}$, time-integrated total residual magnetic field strengths $\int b^f_{tot}$, and actuation control strengths c. The weighted performance metric strengths z may be divided into a first component $z_a$, a second component $z_b$, and a third component $z_c$.

The weighted metric model 116 comprises a frequency weighting, which reflects the frequency components of the three inputs (i.e., fine total residual magnetic field vector $\overrightarrow{b^f_{tot}}$, the time-integrated total residual magnetic field vector $\overrightarrow{\int b^f_{tot}}$, and the actuation control vector $\overrightarrow{c}$) that are important or not important. For example, a high weight may be assigned to the more important frequencies of each of the three inputs (e.g., to the frequencies of the MEG magnetic field $B_{MEG}$ to be measured by the fine magnetometers 26b or to the frequency bands of the total residual magnetic field $B^f_{TOT}$ (e.g., 0 Hz, 60 Hz, 120 Hz, 180 Hz, etc.) that must be minimized), and a smaller or near-zero weight may be assigned to the less important frequencies (e.g., to high frequencies beyond the bandwidth of the magnetometers 26 and magnetic field actuators 28).

In the illustrated embodiment, the metric vector $\overrightarrow{z}$ is a cost function that must be minimized (kept small), which is the goal of optimal linear feedback control loop 100, the desired system performance is good, which means that the total residual magnetic field $B^f_{TOT}$ at the fine magnetometers 26b, the time-integration of the total residual magnetic field $B^f_{TOT}$ at the fine magnetometers 26b, and the control effort of the optimal linear controllers 56 of the signal acquisition unit 18 are all kept small (in proportion to the weightings effectively assigned to them by the weighted space-state model 116). Selecting the weightings of the weighted metric model 116 allows selection of the desired tradeoffs between performance and efficiency of the signal acquisition unit 18.

The first two components $z_a$ and $z_b$ of the total performance metric vector $\vec{z}$ (i.e., keeping the total residual magnetic field $B^f_{TOT}$ at the fine magnetometers 26b and the time-integration of the total residual magnetic field $B^f_{TOT}$ at the fine magnetometers 26b small) ensures that that the signal acquisition unit 18 is operated with a high performance. The third component $z_c$ of the total performance metric vector $\vec{z}$ (i.e., keeping the control effort of the optimal linear controllers 56 small) ensures that the signal acquisition unit 18 is operated efficiently. Control effort corresponds to how hard the magnetic field actuators 28 are working. A signal acquisition unit 18 that generates a reasonable control effort will require less power (less energy is consumed and less heat is dissipated), size, and weight and will work more efficiently.

Notably, using the time-integrated total residual magnetic field vector $\overrightarrow{\int b^f_{tot}}$ as the second input to the weighted metric model 116 to generate the total performance metric vector $\vec{z}$ is advantageous for the following reason. The biggest source of noise to the signal acquisition unit 18 is the outside magnetic field $B_{OUT}$, and in particular, the Earth's magnetic field, which does not change much with time. Thus, the signal acquisition unit 18 experiences a large DC (0 Hz) noise component.

Without a time-integral term in the total performance metric vector z, finite gains will be assigned to the optimal linear control model 118. Even without any noise in the magnetometers 26 and actuators 28, the finite gains will decrease the DC effect due to the Earth's magnetic field by some factor, but will not drive it to zero. By including a time-integral, any persistent small remaining DC magnetic field at the fine magnetometers 26b is integrated in time, its time-integral grows ever larger, and the corresponding part of the cost metric becomes infinite. To combat such an infinite metric (worst possible control performance), poles at the origin (integrators) are provided in the optimal linear control model 118. Essentially, the time-integrated total residual magnetic field vector $\overrightarrow{\int b^f_{tot}}$ implements an "infinite" gain at DC in a practical and achievable manner in the optimal linear control model 118.

Assuming for purpose of illustration that the pre-magnetometer noise vector $\vec{a}$, the post-magnetometer noise vector $\vec{b}$, the pre-actuator noise vector $\vec{c}$, and the post-actuator noise vector $\vec{d}$ are zero, the poles at the origin provided in the optimal linear control model 118 have the effect of driving the steady-state (DC) errors of the fine total residual magnetic field vector $\vec{b^f_{tot}}$ to zero. However, the pre-magnetometer noise vector $\vec{a}$, the post-magnetometer noise vector $\vec{b}$, the pre-actuator noise vector $\vec{c}$, and the post-actuator noise vector $\vec{d}$ will actually be non-zero, in which case, instead of being driven to zero, the steady-state (DC) errors of the fine total residual magnetic field vector $\vec{b^f_{tot}}$, the steady-state (DC) errors will be driven to an available noise floor provided by the pre-magnetometer noise vector $\vec{a}$, the post-magnetometer noise vector $\vec{b}$, the pre-actuator noise vector $\vec{c}$, and the post-actuator noise vector $\vec{d}$. Thus, the inclusion of the time-integrated total residual magnetic field strengths $\int b^f_{tot}$ in the total performance metric vector $\vec{z}$ facilitates maximal reduction of the slow components (e.g., DC) in the fine total residual magnetic field vector $\vec{b^f_{tot}}$.

As briefly discussed above, time-integrated total residual magnetic field vector $\overrightarrow{\int b^f_{tot}}$ may either be exact or approximate, the latter of which provides allows the magnetic field integration function 126 to be more simply implemented. In particular, when computing an exact time-integral of a fine total residual magnetic field strength $b^f_{tot}$, an additional transformation is required, so that there are no unstabilizable poles on the imaginary axis (uncontrollable neutrally stable poles that originate from the weighting function). As such, unstabilizable neutrally stable poles can violate the formal conditions for successful H2 and Hinfinity control design. Computing an approximate time-integral of a fine total residual magnetic field strength $b^f_{tot}$ achieves the same purposes as computing the exact time-integral to any desired accuracy (by making the approximation parameter ε), but it is simpler.

It should be appreciated that the first two components $z_a$ and $z_b$ of the total performance metric vector $\vec{z}$ can be minimized even when a direct measurement from one, many, or all the fine magnetometers 26b is not yet available (e.g. they are not yet in their operating range, or they dropped back out-of-range due to saturation or other factors and have not yet been brought back into an operational mode). As discussed above, the total residual magnetic field $B^F_{TOT-EST}$ may be estimated in real-time at each of the fine magnetometers 26b even when direct measurements of the total residual magnetic field $B_{TOT-MEAS}$ from the fine magnetometers 26b are not yet available. Thus, the magnetic field estimation function 122 may estimate the total residual magnetic field strengths $b^f_{tot-est}$ representing the estimated total residual magnetic field $B^F_{TOT-EST}$ at the fine magnetometers 26b, such that first two components $z_a$ and $z_b$ of the total performance metric vector $\vec{z}$ may be minimized even when some or all of the noisy measured total residual magnetic field strengths $b^f_{tot-meas}$ are not available because some or all of the fine magnetometer transfer functions $g2^f(s)$ are deemed to be out-of-range.

In an optional embodiment, an estimated total residual magnetic field vector $\vec{b^f_{tot-est}}$ output by the magnetic field estimation function 122, and a time-integral of the estimated total residual magnetic field vector $\overrightarrow{\int b^f_{tot-est}}$ may be input into the weighted metric model 116, such that the total performance metric vector $\vec{z}$ output by the weighted metric model 116 not only contains the weighted performance metric strengths z of the fine total residual magnetic field strengths $b^f_{tot}$, the time-integrated total residual magnetic field strengths $\int b^f_{tot}$, and the actuation control strengths c, but also contains the weighted performance metric strengths z of the estimated total residual magnetic field strengths $b^f_{tot-est}$ and the time-integrated total residual magnetic field strengths $\int b^f_{tot-est}$.

The weighted metric model 116 for a particular metric may be characterized with the following state-space linear equations:

$$\dot{x}4(t) = A4 \cdot x4(t) + B4a \cdot b^f_{tot}(t); \quad [18a]$$

$$z_a(t) = C4 \cdot x4(t) + D4a \cdot b^f_{tot}(t); \quad [18b]$$

$$\dot{x}4(t) = A4 \cdot x4(t) + B4b \cdot \int b^f_{tot}(t); \quad [19a]$$

$$z_b(t) = C4 \cdot x4(t) + D4b \cdot \int b^f_{tot}(t); \quad [19b]$$

$$\dot{x}4(t) = A4 \cdot x4(t) + B4c \cdot c(t); \text{ and} \quad [20a]$$

$$z_c(t) = C4 \cdot x4(t) + D4c \cdot c(t), \quad [20b]$$

where x3(t) is a defined time-varying state vector; $b^f_{tot}(t)$ is a time-varying fine total residual magnetic field strength representing the strength of the total residual magnetic field $B^F_{TOT}$ at the fine magnetometer 26b; $z_a(t)$ is a time-varying weighted performance metric strength of the time-varying fine total residual magnetic field strength $b^f_{tot}(t)$; $\int b^f_{tot}(t)$ is a time-integrated total residual magnetic field strength representing the strength of the time-integration of the total residual magnetic field $B^F_{TOT}$ at the fine magnetometer 26b; $z_b(t)$ is a time-varying weighted performance metric strength of the time-integrated total residual magnetic field strength $\int b^f_{tot}(t)$; c(t) is a time-varying actuation control strength representing the strength of the actuation control signal C output by the linear optimal controller 56; $z_c(t)$ is a time-varying weighted performance metric strength of the time-varying actuation control strength c(t); A4 is a defined constant state matrix for the performance of the optimal linear control model 118; B4a is a defined constant input matrix for the total residual magnetic field suppression performance of the optimal linear control model 118; B4b is a defined constant input matrix for the time-integrated total residual magnetic field suppression performance of the optimal linear control model 118; B4c is a defined constant input matrix for the control effort performance of the optimal linear control model 118; C4 is a defined constant output matrix for the performance of the optimal linear control model 118; D4a is a defined constant feedthrough (or feedforward) matrix for the total residual magnetic field suppression performance of the optimal linear control model 118; D4b is a defined constant feedthrough (or feedforward) matrix for the time-integrated total residual magnetic field suppression performance of the optimal linear control model 118; D4c is a defined constant feedthrough (or feedforward) matrix for the control effort performance of the optimal linear control model 118; $\dot{x}4a(t)$ is a time-varying derivative of the state vector x4a(t); $\dot{x}4b(t)$ is a time-varying derivative of the state vector x4b(t); and $\dot{x}4c(t)$ is a time-varying derivative of the state vector x4c(t).

Equations [18a]-[18b], [19a]-[19b], and [20a-20b] can be equivalently written in frequency-form in accordance with equation [3], as follows:

$$z_a(s) = g4a(s) \cdot b^f_{tot}(s); \qquad [21a]$$

$$z_b(s) = g4b(s) \cdot \int b^f_{tot}(s); \text{ and} \qquad [21b]$$

$$z_b(s) = g4c(s) \cdot c(t), \qquad [21c]$$

where s is the Laplace frequency domain variable; $z_a(s)$ is the Laplace transform of the time-varying weighted performance metric strength of the time-varying fine total residual magnetic field strength $b^f_{tot}(t)$; $b^f_{tot}(s)$ is the Laplace transform of the time-varying fine total residual magnetic field strength $b^f_{tot}(t)$; g4a(s) is a fine total residual magnetic field transfer function expressed as $(C4(sI-A4)^{-1}B4a+D4a)$ in accordance with equation [5]; $z_b(s)$ is the Laplace transform of the time-varying weighted performance metric strength of the time-integrated total residual magnetic field strength $\int b^f_{tot}(t)$; $\int b^f_{tot}(s)$ is the Laplace transform of the time-integrated total residual magnetic field strength $\int b^f_{tot}(t)$; g4b(s) is time-integrated total residual magnetic field transfer function expressed as $(C4(sI-A4)^{-1}B4b+D4b)$ in accordance with equation [5]; $z_c(s)$ is the Laplace transform of the time-varying weighted performance metric strength of the actuation control strength c(t); c(s) is the Laplace transform of the actuation control strength c(t); and g4c(s) is an actuation control transfer function expressed as $(C4(sI-A4)_{-1}B4c+D4c)$ in accordance with equation [5].

Thus, the weighted metric model 116 may use a weighted matrix transfer function G4(s) configured for, in response an input of a fine total residual magnetic field vector $\overrightarrow{b^f_{tot}}(s)$ containing fine total residual magnetic field strengths $b^f_{tot}(s)$ representing the strength of the total residual magnetic field $B^F_{TOT}$ at the fine magnetometers 26b of the signal acquisition unit 18, an input of time-integrated total residual magnetic field vector $\overrightarrow{\int b^f_{tot}}(s)$ containing time-integrated total residual magnetic field strengths $\int b^f_{tot}(s)$ representing the strengths of the time-integration of the total residual magnetic field $B^F_{TOT}$ at the fine magnetometers 26b of the signal acquisition unit 18, and an input of an actuation control vector $\overrightarrow{c}(s)$ containing actuation control strengths c(s) representing the strengths of the actuation control signals C respectively output by the optimal linear controllers 56 of the signal acquisition unit 18, and outputting a total performance metric vector $\overrightarrow{z}(s)$ containing weighted performance metric strengths z(s) of the fine total residual magnetic field strengths $b^f_{tot}(s)$, time-integrated total residual magnetic field strengths $\int b^f_{tot}(s)$, and the actuation control strengths c(s).

In particular, the weighted matrix transfer function G4(s) has a dimension $(2N^f+M) \times (2N^f+M)$, where $N^f$ is the total number of fine magnetometers 26b and M is the total number of magnetic field actuators 28. The diagonal entries of the magnetometer matrix transfer function G4(s) are populated with fine total residual magnetic field transfer functions g4a(s): 1 . . . $N^f(s)$, integrated total residual magnetic field transfer functions g4b(s): 1 . . . $N^f(s)$, and actuation control transfer functions g4c(s):1 . . . M(s), and the remaining entries of the magnetometer matrix transfer function G2(s) are unknown, but presumed to be null entries.

It follows that the fine total residual magnetic field vector $\overrightarrow{b^f_{tot}}(s)$ has a dimension $N^f$, the time-integrated total residual magnetic field vector $\overrightarrow{\int b^f_{tot}}(s)$ has a dimension $N^f$, and the actuation control vector $\overrightarrow{c}(s)$ has a dimension M, such that the fine total residual magnetic field vector $\overrightarrow{b^f_{tot}}(s)$ contains fine total residual magnetic field strengths $b^f_{tot}(s)$: 1 . . . $N^f$, the time-integrated total residual magnetic field vector $\overrightarrow{\int b^f_{tot}}(s)$ contains time-integrated total residual magnetic field strengths $\int b^f_{tot}(s)$: 1 . . . N, and the actuation control vector $\overrightarrow{c}(s)$ contains actuation control strengths c(s): 1 . . . M.

The optimal linear control model 118 is configured for quantifying the control properties of the optimal linear controllers 56. In particular, the optimal linear control model 118 is configured, in response to an input of the estimated total residual magnetic field vector $\overrightarrow{b^f_{tot-est}}$, outputting the actuation control vector $\overrightarrow{c}$ representing the actuation control signals C respectively output by the optimal linear controllers 56 to the magnetic field actuators 28.

The optimal linear control model 118 for a particular optimal linear controller 102 may be characterized with the following state-space linear equations:

$$\dot{x}k(t) = Ak \cdot xk(t) + Bk \cdot b_{tot-est}(t); \text{ and} \qquad [22a]$$

$$c(t) = Ck \cdot x2(t) + D2 \cdot xk(t), \qquad [22b]$$

where xk(t) is a defined time-varying state vector of the optimal linear controller 102; $b^f_{tot-est}(t)$ is a time-varying estimated total residual magnetic field strength representing the total residual magnetic field estimate $B^F_{TOT-EST}(t)$ at a fine magnetometer 26b; c(t) is a time-varying actuation control strength representing the actuation control signal C output by the optimal linear controller 102; Ak is a defined constant state matrix of the optimal linear controller 102; Bk is a defined constant input matrix of the optimal linear controller 102; Ck is a defined constant output matrix of the optimal linear controller 102; Dk is a defined constant feedthrough (or feedforward) matrix of the magnetometer 26; and $\dot{x}k(t)$ is a time-varying derivative of the state vector xk(t).

Equations [22a]-[22b] can be equivalently written in frequency-form in accordance with equation [3], as follows: [23]c(s)=k(s)·$b_{tot\text{-}est}$(s), where s is the Laplace frequency domain variable; c(s) is the Laplace transform of the time-varying actuation control strength c(t); $b^f_{tot\text{-}est}$(s) is the Laplace transform of the time-varying estimated total residual magnetic field strength $b^f_{tot\text{-}est}$(t); and k(s) is an optimal linear control transfer function expressed as (Ck(sI−Ak)$^{-1}$Bk+Dk) in accordance with equation [5].

Thus, the optimal linear control model 118 may use an optimal linear control matrix transfer function K(s) configured for, in response to an input of the estimated total residual magnetic field vector $\vec{b}_{tot\text{-}est}$(s), outputting an actuation control vector $\vec{c}(s)$ containing actuation control strengths c(s) representing the strengths of the actuation control signals C output by the optimal linear controllers 56. In the exemplary embodiment, equation [23] is used as a building block for generating the optimal linear control matrix transfer function K(s) from the optimal linear control transfer functions k(s), generating the estimated total residual magnetic field vector $\vec{b}_{tot\text{-}est}$(s) from the estimated total residual magnetic field strengths $b_{tot\text{-}est}$(s), and generating the actuation control vector $\vec{c}(s)$ from the actuation control strengths c(s), for all of the optimal linear controllers 56.

In particular, the optimal linear control matrix transfer function K(s) has a dimension M×$N^f$, where M is the total number of optimal linear controllers 56 (i.e., the total number of magnetic field actuators 28), and $N^f$ is the total number of fine magnetometers 26b. The diagonal entries of the magnetometer matrix transfer function K(s) are populated with optimal linear control transfer functions k(s):1 . . . M(s), and the remaining entries of the magnetometer matrix transfer function K(s) are unknown, but presumed to be null entries.

It follows that the estimated total residual magnetic field vector $\vec{b}_{tot\text{-}est}$(s) has a dimension $N^f$, and the actuation control vector $\vec{c}(s)$ has a dimension M, such that the estimated total residual magnetic field vector $\vec{b}_{tot\text{-}est}$(s) contains estimated total residual magnetic field strengths $b_{tot\text{-}est}$(s): 1 . . . $N^f$, and the actuation control vector $\vec{c}(s)$ contains actuation control strength strengths c(s): 1 . . . M(s).

Once the dynamic map 102 is defined, the optimizer 108 may determine an optimal linear control matrix transfer function K*(s) (i.e., by selecting the matrices A, B, C, and D for each optimal linear control transfer functions k*(s)) using appropriate linear optimization techniques (e.g., linear quadratic regulator (LQR), H2, Hinfinity, etc.) in a manner that yields the lowest total performance metric vector $\vec{z}$ even in the presence of unavoidable noise sources, where "*" is used to denote the optimal case.

In one embodiment, determination of the optimal linear control matrix transfer function K*(s) can be broken into two components: 1) selection of an optimal estimator (e.g., a Kalman matrix transfer function F*(s)) that estimates a full internal state x of the dynamic map 102 based on the estimated total residual magnetic field vector $\vec{b}_{tot\text{-}est}$(s) (see equation [2a]); and 2) selection of an optimal full-state matrix transfer function Q*(s) (e.g., using LQR techniques) that acts on the estimated full internal state x of the dynamic map 102 to generate the actuation control vector $\vec{c}(s)$ (see equation [2b]). The Kalman matrix transfer function F*(s) and optimal full-state matrix transfer function Q*(s) may be appropriately connected, such that each optimal linear control matrix transfer function K(s) equals [F*(s), Q*(s)].

In another embodiment, the optimal linear control matrix transfer function K*(s) may be determined by employing H2 or Hinfinity techniques (which are partial-state controllers) that act directly on the estimated total residual magnetic field vector $\vec{b}_{tot\text{-}est}$(s) to generate the actuation control vector $\vec{c}(s)$.

In still another embodiment, the Hinfinity partial-state controller may be split into an optimal full-state estimator that estimates a full internal state x of the dynamic map 102 based on the estimated total residual magnetic field vector $\vec{b}_{tot\text{-}est}$(s), and an optimal controller that acts on the estimated full internal state x of the dynamic map 102 to generate the actuation control vector $\vec{c}(s)$.

Nevertheless, all of these approaches (design an optimal feedback controller that acts on the estimated total residual magnetic field vector $\vec{b}_{tot\text{-}est}$(s); or design a full-state estimator based on the estimated total residual magnetic field vector $\vec{b}_{tot\text{-}est}$(s) and a controller that then acts on the estimated full internal state x) are substantially equivalent.

At the end of this optimization process, the resulting optimal linear control model 118 will comprise an optimal linear control matrix transfer function K*(s) containing optimal linear control transfer functions k*(s), which can be incorporated into the optimal linear controllers 56 that will optimize the performance of the signal acquisition unit 18. That is, the optimal linear controllers 56 will be optimized in that they will control the magnetic field actuators 28 to cancel the outside magnetic field $B_{TOT}$ in a manner that suppresses the most important frequencies of the total residual magnetic field $B_{TOT}$ at the fine magnetometers 26b to the lowest level, and will do so with reasonable control effort.

The optimal linear controllers 56 of the signal acquisition unit 18 operate, in real-time, by receiving the total residual magnetic field estimates $B_{TOT\text{-}EST}$ at the fine magnetometers 26b from the magnetic field estimator 54, performing computations on the total residual magnetic field estimates $B_{TOT\text{-}EST}$ in accordance with equation [23], and outputting actuation control signals C to the magnetic field actuators 28.

Equivalently, the optimal linear controllers 56 of the signal acquisition unit 18 may operate, in real-time, by receiving the total residual magnetic field estimates $B_{TOT\text{-}EST}$ at the fine magnetometers 26b from the magnetic field estimator 54, performing computations in state-space on the total residual magnetic field estimates $B_{TOT\text{-}EST}$ in accordance with equations [22a-22b], and outputting actuation control signals C to the magnetic field actuators 28. Feeding the total residual magnetic field estimates $B_{TOT\text{-}EST}$ back to the actuation control signals C via the optimal linear controllers 56 closes the optimal linear feedback control loop 50 in an optimal way.

Figure 8:
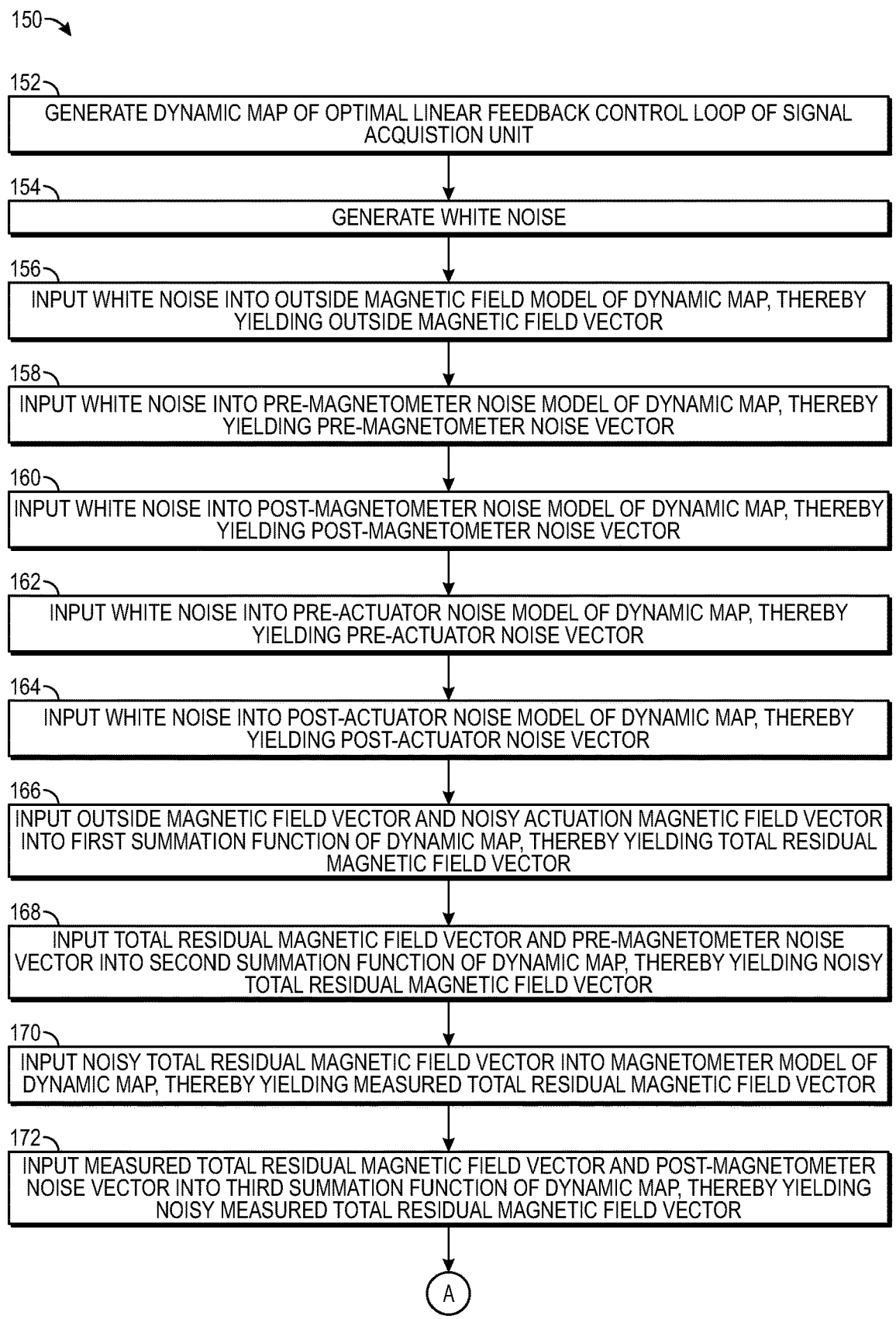
FIG. 8 is a flow diagram of one exemplary method of operating the optimal linear controller design system of FIG. 6.
Figure 8:
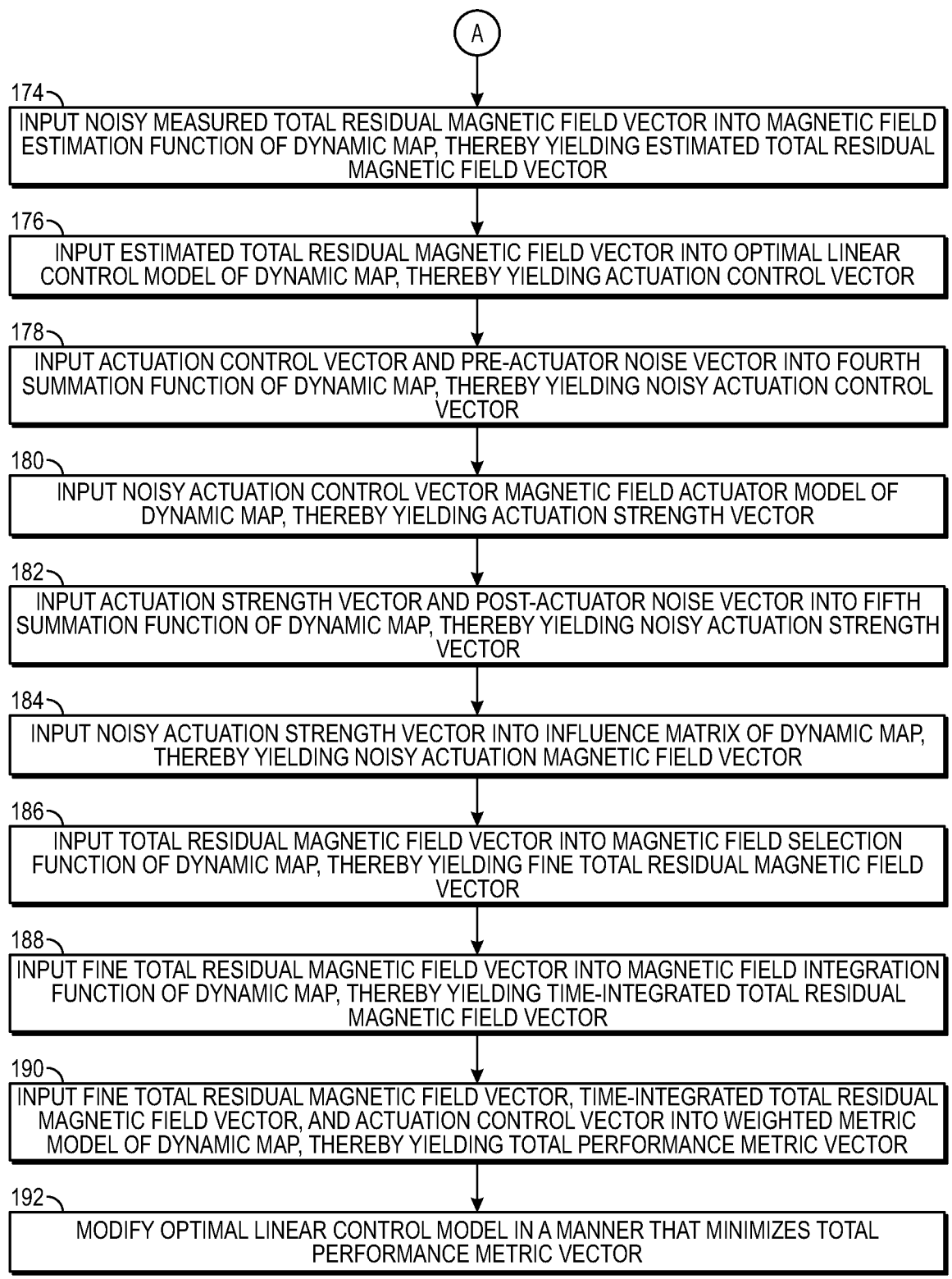

Referring now to FIG. 8, one exemplary method 150 of designing one or more optimal linear controllers for use in an optimal linear feedback control loop of an active shield magnetometry system, e.g., the optimal linear controllers 56 in the optimal linear feedback control loop 50 of the signal acquisition unit 18 illustrated in FIG. 4, will not described.

The method 150 comprises generating a dynamic map 102 of the optimal linear feedback control loop 50 of the signal acquisition unit 18, which includes the outside magnetic field model 110, pre-magnetometer noise model 110a, post-magnetometer model 110b, pre-actuator noise model 110c, post-actuator noise model 110d, magnetometer model 112, actuating magnetic field model 114, which includes the magnetic field actuator model 114a and influence matrix 114b, metric weighting model 116, optimal linear controller model 118, summation functions 120a-120e, magnetic field estimation function 122, magnetic field selection function 124, and magnetic field integration function 126 (step 152). Each of the outside magnetic field model 110, pre-magnetometer noise model 110a, post-magnetometer model 110b, pre-actuator noise model 110c, post-actuator noise model 110d, magnetometer model 112, magnetic field actuator model 114a, metric weighting model 116, and optimal linear controller model 118 may comprise a matrix of functions, e.g., matrix transfer functions matrices of state-space differential equations.

The method 150 further comprises generating noise (e.g., white noise w, $w_a$, $w_b$, $w_c$, and $W_d$) (step 154) and inputting the white noise w into the outside magnetic field model 110, thereby yielding an outside magnetic field vector $\vec{b}_{out}$ containing outside magnetic field strengths $b_{out}$ representing strengths of the outside magnetic field $B_{OUT}$ respectively at the magnetometers 26 (step 156). The outside magnetic field model 110 may be weighted at a plurality of distinct frequencies (e.g., a frequency in the range of 0 Hz-5 Hz, and any harmonic frequencies, e.g., 60 Hz harmonic frequencies).

The method 150 further comprises inputting the white noise $w_a$ into the pre-magnetometer noise model 110a, thereby yielding a pre-magnetometer noise vector a containing pre-magnetometer noise strengths $n_a$ representing strengths of the pre-magnetometer noise $N_A$ at the magnetometers 26 (step 158); inputting the white noise $w_b$ into the post-magnetometer noise model 110b, thereby yielding a post-magnetometer noise vector $\vec{n}_b$ containing post-magnetometer noise strengths $n_b$ representing strengths of the post-magnetometer noise $N_B$ at the magnetometers 26 (step 160); inputting the white noise $w_c$ into the pre-actuator noise model 110c, thereby yielding a pre-actuator noise vector $\vec{n}_c$ containing pre-actuator noise strengths $n_c$ representing strengths of the pre-actuator noise $N_C$ at the magnetic field actuators 28 (step 162); and inputting the white noise $w_d$ into the post-actuator noise model 110d, thereby yielding a post-actuator noise vector $\vec{n}_d$ containing post-actuator noise strengths $n_d$ representing strengths of the post-actuator noise $N_D$ at the magnetic field actuators 28 (step 164).

The method 150 further comprises inputting the outside magnetic field vector $\vec{b}_{out}$ and a noisy actuated magnetic field vector $\vec{b'}_{act}$ into the first magnetic field summation function 120a, thereby yielding a total residual magnetic field vector $\vec{b}_{tot}$ representing strengths of a total residual magnetic field $B_{TOT}$ respectively at the magnetometers 26, and in particular, a coarse total residual magnetic field vector $\vec{b^c}_{tot}$ representing strengths of a coarse total residual magnetic field $B^C_{TOT}$ respectively at the coarse magnetometers 26a, and a fine total residual magnetic field vector $\vec{b^c}_{tot}$ representing strengths of a fine total residual magnetic field $B^F_{TOT}$ respectively at the fine magnetometers 26b (step 166).

The method 150 further comprises inputting the total residual magnetic field vector $\vec{b}_{tot}$ and the pre-magnetometer noise vector $\vec{n}_a$ into the second summation function 120b, thereby yielding a noisy total residual magnetic field vector b containing noisy total residual magnetic field strengths $b'_{tot}$ representing strengths of a noisy total residual magnetic field $B'_{TOT}$ respectively at the magnetometers 26 with pre-magnetometer noise, and in particular, yielding a noisy coarse total residual magnetic field vector $\vec{b'^c}_{tot}$ containing noisy coarse total residual magnetic field strengths $b'^c_{tot}$ representing strengths of a noisy coarse total residual magnetic field $B'^C_{TOT}$ respectively at the coarse magnetometers 26a with pre-magnetometer noise, and a noisy fine total residual magnetic field vector $\vec{b'^f}_{tot}$ containing noisy fine total residual magnetic field strengths $b'^f_{tot}$ representing strengths of a noisy coarse total residual magnetic field $B'^F_{TOT}$ respectively at the fine magnetometers 26b with pre-magnetometer noise (step 168).

The method 150 further comprises inputting the total residual magnetic field vector $\vec{b'}_{tot}$ into the magnetometer model 112, thereby yielding a measured total residual magnetic field vector $\vec{b}_{tot\text{-}meas}$ containing measured total residual magnetic field strengths $b_{tot\text{-}meas}$ representing strengths of the total residual magnetic field $B_{TOT\text{-}MEAS}$ respectively measured by the magnetometers 26, and in particular, yielding a measured total residual magnetic field vector $\vec{b^c}_{tot\text{-}meas}$ containing measured total residual magnetic field strengths $b^c_{tot\text{-}meas}$ representing strengths of the total residual magnetic field $B^C_{TOT\text{-}MEAS}$ respectively measured by the coarse magnetometers 26a, and a measured total residual magnetic field vector $b^f_{tot\text{-}meas}$ containing measured total residual magnetic field strengths $b^f_{tot\text{-}meas}$ representing strengths of the total residual magnetic field $B^F_{TOT\text{-}MEAS}$ respectively measured by the fine magnetometers 26b (step 170).

The method 150 further comprises inputting the measured total residual magnetic field vector $\vec{b}_{tot\text{-}meas}$ and the post-magnetometer noise vector bi into the third summation function 120c, thereby yielding a noisy measured total residual magnetic field vector $\vec{b'}_{tot\text{-}meas}$ containing noisy total residual magnetic field strengths $b'_{tot\text{-}meas}$ representing strengths of a noisy measured total residual magnetic field $B'_{TOT\text{-}MEAS}$ respectively at the magnetometers 26 with post-magnetometer noise, and in particular, yielding a noisy measured total residual magnetic field vector $\vec{b'^c}_{tot\text{-}meas}$ containing noisy measured total residual magnetic field strengths $b'^c_{tot\text{-}meas}$ representing strengths of a noisy measured total residual magnetic field $B'^C_{TOT\text{-}MEAS}$ respectively at the coarse magnetometers 26a with post-magnetometer noise, a noisy measured total residual magnetic field vector $\vec{b'^f}_{tot\text{-}meas}$ containing noisy measured total residual magnetic field strengths $b'^f_{tot\text{-}meas}$ representing strengths of a noisy measured total residual magnetic field $B'^F_{TOT\text{-}MEAS}$ respectively at the fine magnetometers 26b with post-magnetometer noise (step 172).

The method 150 further comprising inputting the noisy measured total residual magnetic field vector $\vec{b'}_{tot\text{-}meas}$ into the magnetic field estimation function 122, thereby yielding an estimated total residual magnetic field vector $\vec{b}^f_{tot\text{-}est}$ containing estimated total residual magnetic field strengths $b^f_{tot\text{-}est}$ representing strengths of estimates of the total residual magnetic field $B^F_{TOT\text{-}EST}$ at the fine magnetometers 26b (step 174).

The method 150 further comprising inputting the estimated total residual magnetic field vector $b^f_{tot\text{-}est}$ into the optimal linear control model 118, thereby yielding an actuation control vector $\vec{c}$ containing actuation control strengths c representing the strengths of actuation control signals C respectively generated by the optimal linear controllers 56 (step 176).

The method 150 further comprises inputting the actuation control vector $\vec{c}$ and the pre-actuator noise vector $\vec{n}_c$ into the fourth summation function 120d, thereby yielding a noisy actuation control vector $\vec{c}'$ containing noisy actuation control strengths c' representing strengths of noisy actuation control signals C' respectively output by the plurality of optimal linear controllers 56 with pre-actuator noise (step 178).

The method 150 further comprises inputting the noisy actuation control vector $\vec{c}'$ into the actuated magnetic field model 114, thereby yielding a noisy actuated magnetic field vector $\vec{b}'_{act}$ containing noisy actuated magnetic field strengths $b'_{act}$ representing strengths of the noisy actuated magnetic field $B'_{ACT}$ generated by the magnetic field actuators 28 respectively at the magnetometers 26.

In particular, the method 150 further comprises inputting the noisy actuation control vector $\vec{c}'$ into the magnetic field actuator model 114a of the actuated magnetic field model 114, thereby yielding an actuation strength vector $\vec{s}$ containing actuation strengths s representing actuation strengths S of the magnetic field actuators 28 (step 180); inputting the actuation strength vector $\vec{s}$ and the post-actuator noise vector $\vec{n}_d$ into the fifth summation function 120e, thereby yielding a noisy actuation strength vector $\vec{s}'$ containing noisy actuation strengths s' representing noisy actuation strengths S' of the magnetic field actuators 28 with post-actuator noise (step 182); and inputting the noisy actuation vector $\vec{s}'$ into the matrix of influence 114b of the actuated magnetic field model 114, thereby yielding the noisy actuated magnetic field vector $\vec{b}'_{act}$ (step 184), which is input, along with the outside magnetic field vector $\vec{b}_{out}$, into the first summation function 120a, thereby yielding the total residual magnetic field vector $\vec{b}_{tot}$, as discussed above with respect to step 166.

The method 150 further comprises inputting the total residual magnetic field vector $\vec{b}_{tot}$ into the magnetic field selection function 124, thereby yielding a fine total residual magnetic field vector $\vec{b}^f_{tot}$ containing fine total residual magnetic field strengths $b^f_{tot}$ representing the total residual magnetic field $B^F_{TOT}$ respectively at the fine magnetometers 26b (step 186); and inputting the fine total residual magnetic field vector $\vec{b}^f_{tot}$ into the magnetic field integration function 126, thereby yielding a time-integrated total residual magnetic field vector $\overrightarrow{\int b^f_{tot}}$ containing time-integrated total residual magnetic field strengths $\int b^f_{tot}$ representing a time-integrated total residual magnetic field $\int B^F_{TOT}$ respectively at the fine magnetometers 26b (step 188).

The method 150 further comprising inputting the fine total residual magnetic field vector $\vec{b}^f_{tot}$, the time-integrated total residual magnetic field vector $\overrightarrow{\int b^f_{tot}}$, and the actuation control vector $\vec{c}$ into the weighted metric model 116, thereby yielding a total performance metric vector $\vec{z}$ containing weighted performance metric strengths z respectively defining performances of the optimal linear control model 118 (step 190). The weighted metric model 116 may comprise a frequency weighting, as discussed above.

The method 150 lastly comprises modifying the optimal linear control model 118 in a manner that minimizes the total performance metric vector $\vec{z}$ (step 192). For example, the optimal linear control model 118 may be modified in accordance with a linear optimization technique selected from one or more of a linear quadratic regulator (LQR) optimization technique, H2 optimization technique, and Hinfinity optimization technique.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An active shield magnetometry system, comprising:
   at least one magnetic field actuator configured for generating an actuated magnetic field that at least partially cancels an outside magnetic field, thereby yielding a total residual magnetic field;
   a plurality of magnetometers respectively configured for measuring the total residual magnetic field and outputting a plurality of total residual magnetic field measurements;
   at least one feedback control loop comprising at least one optimal linear controller configured for controlling the actuated magnetic field at least partially based on at least one of the plurality of total residual magnetic field measurements respectively output by at least one of the plurality of magnetometers.

2. The active shield magnetometry system of claim 1, wherein each of the at least one optimal linear controller comprises one of a linear quadratic regulator (LQR) controller, an H2 controller, and an Hinfinity controller.

3. The active shield magnetometry system of claim 1, wherein each of the at least one optimal linear controller is configured for controlling the actuated magnetic field in a manner that suppresses the total residual magnetic field at at least one of the plurality of magnetometers.

4. The active shield magnetometry system of claim 3, wherein each of the at least one optimal linear controller is configured for controlling the actuated magnetic field in a manner that minimizes a performance metric that includes a magnitude of the suppressed total residual magnetic field at the at least one magnetometer and a magnitude of the control effort of the at least one optimal linear controller.

5. The active shield magnetometry system of claim 4, wherein the total performance metric further includes a magnitude of a time-integral of the suppressed total residual magnetic field at the at least one magnetometer.

6. The active shield magnetometry system of claim 1,
wherein the plurality of magnetometers comprises a plurality of coarse magnetometers respectively configured for coarsely measuring the total residual magnetic field and outputting a plurality of coarse total residual magnetic field measurements, and a plurality of fine magnetometers respectively configured for finely measuring the total residual magnetic field and outputting a plurality of fine total residual magnetic field measurements;
wherein the at least one feedback control loop comprises a coarse feedback control loop, such that the at least one optimal linear controller is configured for coarsely controlling the actuated magnetic field at least partially based on at least one of the plurality of coarse total residual magnetic field measurements respectively output by at least one of the plurality of coarse magnetometers; and
wherein the at least one feedback control loop further comprises a fine feedback control loop, such that the optimal linear controller is configured for finely controlling the actuated magnetic field at least partially based on at least one of the plurality of fine total residual magnetic field measurements respectively output by at least one of the plurality of fine magnetometers.

7. The active shield magnetometry system of claim 6,
wherein the plurality of coarse feedback control loops are configured for coarsely controlling the actuated magnetic field respectively in a manner that suppresses the total residual magnetic field at the at least one fine magnetometer to a baseline level, such that the at least one fine magnetometer comes in-range; and
wherein the plurality of fine feedback control loops are configured finely controlling the actuated magnetic field in a manner that further suppresses the total residual magnetic field at the at least one fine magnetometer to a lower level.

8. The active shield magnetometry system of claim 6, wherein the coarse feedback control loop is configured for estimating the total residual magnetic field at at least one of the plurality of fine magnetometers based on the plurality of coarse total residual magnetic field measurements, and wherein the optimal linear controller of the coarse feedback control loop is configured for coarsely controlling the actuated magnetic field at least partially based on the estimated total residual magnetic field at the at least one fine magnetometer.

9. The active shield magnetometry system of claim 6, wherein each of the plurality of coarse magnetometers is a flux gate magnetometer, and each of the plurality of fine magnetometers is an optically pumped magnetometer (OPM).

10. The active shield magnetometry system of claim 1,
wherein the at least one magnetic field actuator is configured for generating an actuated magnetic field at a plurality of distinct frequencies that at least partially cancels an outside magnetic field at the plurality of distinct frequencies, thereby yielding the total residual magnetic field; and
wherein the at least one feedback control loop comprises a plurality of feedback control loops, and wherein the at least one optimal linear controller comprises a plurality of optimal linear controllers configured for controlling the actuated magnetic field respectively at the plurality of distinct frequencies at least partially based on at least one of the plurality of total residual magnetic field measurements respectively output by the at least one magnetometer.

11. The active shield magnetometry system of claim 10, wherein one of the plurality of distinct frequencies comprises a frequency in the range of 0 Hz-5 Hz.

12. The active shield magnetometry system of claim 10, wherein the plurality of distinct frequencies comprises a plurality of harmonic frequencies.

13. The active shield magnetometry system of claim 12, wherein the harmonic frequencies are 60 Hz harmonic frequencies.

14. The active shield magnetometry system of claim 1, further comprising a processor containing the at least one feedback control loop.

15. The active shield magnetometry system of claim 1, further comprising:
a signal acquisition unit configured for being worn on a head of a user, the signal acquisition unit comprising a support structure, the at least one magnetic field actuator affixed to the support structure, the plurality of magnetometers affixed to the support structure, the signal acquisition unit configured for deriving at least one magnetoencephalography (MEG) signal respectively from at least one of the plurality of total residual magnetic field measurements; and
a signal processing unit configured for determining an existence of neural activity in the brain of the user based on the at least one MEG signal.

16. An active shield magnetometry method, comprising:
generating an actuated magnetic field that at least partially cancels an outside magnetic field, thereby yielding a total residual magnetic field at a plurality of measurement locations;
measuring the total residual magnetic field at the plurality of measurement locations and outputting a plurality of total residual magnetic field measurements;
controlling the actuated magnetic field with at least one optimal linear controller at least partially based on at least one of the plurality of total residual magnetic field measurements.

17. The active shield magnetometry method of claim 16, wherein each of the at least one optimal linear controller comprises one of a linear quadratic regulator (LQR) controller, an H2 controller, and an Hinfinity controller.

18. The active shield magnetometry method of claim 16, wherein the actuated magnetic field is controlled by the at least one optimal linear controller in a manner that suppresses the total residual magnetic field at at least one of the plurality of measurement locations to a baseline level, such that the accuracy of at least of the plurality of total residual magnetic field measurements at the at least one measurement location increases.

19. The active shield magnetometry method of claim 18, wherein the actuated magnetic field is controlled with the at least one optimal linear controller in a manner that minimizes a performance metric that includes a magnitude of the suppressed total residual magnetic field at the at least one measurement location and a magnitude of the control effort of the at least one optimal linear controller.

20. The active shield magnetometry method of claim 19, wherein the total performance metric further includes a magnitude of the time-integral of the suppressed total residual magnetic field at the at least one measurement location.

21. The active shield magnetometry method of claim 16, wherein measuring the total residual magnetic field and outputting a plurality of total residual magnetic field measurements comprises:
coarsely measuring the total residual magnetic field at a plurality of coarse measurement locations and outputting a plurality of coarse total residual magnetic field measurements;
finely measuring the total residual magnetic field at a plurality of fine measurement locations and outputting a plurality of fine total residual magnetic field measurements; and
wherein controlling the actuated magnetic field with the at least one optimal linear controller at least partially based on at least one of the plurality of total residual magnetic field measurements comprises:
coarsely controlling the actuated magnetic field with the at least one optimal linear controller at least partially based on at least one of the plurality of coarse total residual magnetic field measurements; and
finely controlling the actuated magnetic field with the at least one optimal linear controller at least partially based on at least one of the plurality of fine total residual magnetic field measurements.

22. The active shield magnetometry method of claim 21, wherein the actuated magnetic field is coarsely controlled in a manner that suppresses the total residual magnetic field at at least one fine measurement location to a baseline level; and
wherein the actuated magnetic field is finely controlled in a manner that further suppresses the total residual magnetic field at the at least one fine measurement location to a lower level.

23. The active shield magnetometry method of claim 21, further comprising estimating the total residual magnetic field at at least one the plurality of fine measurement locations based on the plurality of coarse total residual magnetic field measurements, wherein the actuated magnetic field is coarsely controlled with the at least one optimal linear controller at least partially based on the estimated total residual magnetic field at the at least one fine measurement location.

24. The active shield magnetometry method of claim 16, wherein the actuated magnetic field is generated at a plurality of distinct frequencies that at least partially cancels an outside magnetic field at the plurality of distinct frequencies, thereby yielding the total residual magnetic field;
wherein the at least one optimal linear controller comprises a plurality of optimal linear controllers; and
wherein the actuated magnetic field is controlled with the plurality of optimal linear controllers respectively at the plurality of distinct frequencies at least partially based on at least one of the plurality of total residual magnetic field measurements.

25. The active shield magnetometry method of claim 24, wherein one of the plurality of distinct frequencies comprises a frequency in the range of 0 Hz-5 Hz.

26. The active shield magnetometry method of claim 24, wherein the plurality of distinct frequencies comprises a plurality of harmonic frequencies.

27. The active shield magnetometry method of claim 26, wherein the harmonic frequencies are 60 Hz harmonic frequencies.

28. The active shield magnetometry method of claim 16, further comprising:
deriving a plurality of magnetoencephalography (MEG) signals respectively from the plurality of total residual magnetic field measurements; and
determining an existence of neural activity in the brain of a user based on the plurality of MEG signals.

* * * * *